(12) United States Patent
Sugiki et al.

(10) Patent No.: US 9,253,997 B2
(45) Date of Patent: Feb. 9, 2016

(54) ALKYLAMINE DERIVATIVE

(75) Inventors: Masayuki Sugiki, Kawasaki (JP); Toru Okamatsu, Kawasaki (JP); Tetsuo Yano, Kawasaki (JP); Shinya Taniguchi, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 183 days.

(21) Appl. No.: 13/600,977

(22) Filed: Aug. 31, 2012

(65) Prior Publication Data

US 2013/0237702 A1 Sep. 12, 2013

Related U.S. Application Data

(63) Continuation of application No. PCT/JP2011/055033, filed on Mar. 4, 2011.

(30) Foreign Application Priority Data

Mar. 4, 2010 (JP) ................................. 2010-048310

(51) Int. Cl.

| | |
|---|---|
| *C07C 275/42* | (2006.01) |
| *C07C 309/51* | (2006.01) |
| *C07C 311/32* | (2006.01) |
| *C07C 311/52* | (2006.01) |
| *C07C 333/08* | (2006.01) |
| *C07C 335/16* | (2006.01) |
| *C07D 209/14* | (2006.01) |
| *C07D 233/61* | (2006.01) |
| *C07D 271/10* | (2006.01) |
| *C07D 295/16* | (2006.01) |
| *C07D 413/04* | (2006.01) |
| *C07D 213/75* | (2006.01) |
| *C07D 295/192* | (2006.01) |
| *A23L 1/226* | (2006.01) |
| *C07C 311/51* | (2006.01) |
| *C07D 213/74* | (2006.01) |

(52) U.S. Cl.
CPC ......... *A23L 1/22657* (2013.01); *A23L 1/22614* (2013.01); *C07C 275/42* (2013.01); *C07C 309/51* (2013.01); *C07C 311/32* (2013.01); *C07C 311/51* (2013.01); *C07C 333/08* (2013.01); *C07C 335/16* (2013.01); *C07D 209/14* (2013.01); *C07D 213/74* (2013.01); *C07D 213/75* (2013.01); *C07D 233/61* (2013.01); *C07D 271/10* (2013.01); *C07D 295/16* (2013.01); *C07D 295/192* (2013.01); *C07D 413/04* (2013.01); *C07C 2101/14* (2013.01); *C07C 2101/18* (2013.01)

(58) Field of Classification Search
CPC .. C07C 275/42; C07C 309/51; C07C 311/32; C07C 311/52; C07C 333/08; C07C 335/16; C07D 209/14; C07D 233/16; C07D 271/10;

C07D 295/16; C07D 413/04; C07D 213/75; C07D 295/192

See application file for complete search history.

(56) References Cited

U.S. PATENT DOCUMENTS

| | | | |
|---|---|---|---|
| 3,979,447 | A | 9/1976 | Bernt et al. |
| 4,065,446 | A | 12/1977 | Bien et al. |
| 4,147,802 | A | 4/1979 | Cook et al. |
| 4,292,429 | A | 9/1981 | Marxer |
| 4,837,225 | A | 6/1989 | Zoller et al. |
| 5,225,559 | A | 7/1993 | Kita et al. |
| 5,585,518 | A | 12/1996 | Marschner et al. |
| 5,962,502 | A | 10/1999 | Makovec et al. |
| 6,323,223 | B1 | 11/2001 | Gong et al. |
| 2009/0227624 | A1 | 9/2009 | Dasgupta et al. |
| 2011/0028394 | A1 | 2/2011 | Karim et al. |
| 2011/0251418 | A1 | 10/2011 | Sugiki et al. |
| 2012/0101039 | A1 | 4/2012 | Fenscholdt et al. |
| 2012/0122784 | A1 | 5/2012 | Norremark et al. |
| 2012/0129926 | A1 | 5/2012 | Norremark |
| 2013/0072491 | A1 | 3/2013 | Yasuda et al. |

FOREIGN PATENT DOCUMENTS

| | | |
|---|---|---|
| JP | 54-125668 | 9/1979 |
| JP | 54-34007 | 10/1979 |
| JP | 57-142977 | 3/1982 |
| JP | 62-33152 | 2/1987 |

(Continued)

OTHER PUBLICATIONS

International Search Report in PCT/JP2011/055033 issued May 24, 2011.
Edward M. Brown et al., "Nature", vol. 366 (1993) pp. 575-580.
Adi Cohen et al., "Current Opinion in Pharmacology", vol. 2 (2002) pp. 734-739.
Ethical drug package insert (5th ed., revised Jan. 2012) for REBAGRA™ tablet.
Minghua Wang et al., "Journal of Biological Chemistry", vol. 281, No. 13 (2006) pp. 8864-8870.
Clinical Chemistry, vol. 22, No. 12, (1976) pp. 2051-2055.

(Continued)

*Primary Examiner* — Samantha Shterengarts

(74) *Attorney, Agent, or Firm* — Oblon, McClelland, Maier & Neustadt, L.L.P.

(57) ABSTRACT

A composition containing a compound represented by General Formula (I) below (see the definition in the specification for the symbols in the formula) or a salt thereof has an excellent CaSR agonistic effect and provides a pharmaceutical agent, a CaSR agonistic agent, a prophylactic or therapeutic agent for a disease that can be ameliorated through CaSR activation as well as seasonings and an agent for imparting kokumi.

(I)

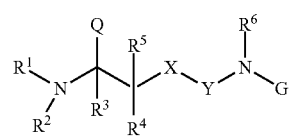

9 Claims, 5 Drawing Sheets

(56) References Cited

FOREIGN PATENT DOCUMENTS

| | | |
|---|---|---|
| JP | 4-182467 | 6/1992 |
| JP | 06-172287 | 6/1994 |
| JP | 7-291918 | 11/1995 |
| JP | 11-147872 | 6/1999 |
| WO | WO 95/07261 A1 | 3/1995 |
| WO | WO 98/27108 A2 | 6/1998 |
| WO | 2006/123725 | 11/2006 |
| WO | 2007/055393 | 5/2007 |
| WO | 2008/139947 | 11/2008 |
| WO | 2009/097113 | 8/2009 |
| WO | 2009/107660 | 9/2009 |
| WO | 2009/119554 | 10/2009 |
| WO | 2009/128523 | 10/2009 |
| WO | 2010/038895 | 4/2010 |
| WO | 2010/136035 | 12/2010 |
| WO | 2010/136036 | 12/2010 |
| WO | 2010/136037 | 12/2010 |
| WO | 2011/014707 | 2/2011 |

OTHER PUBLICATIONS

Rodney F. Lloyd et al., "Journal of Medicinal Chemistry", vol. 8, No. 3, (1965) pp. 398-400.
S. Bashir et al., Analytica Chimica Acta, vol. 519, No. 2, (2004) pp. 181-187.
I. Lalezari et al., "Journal of Medicinal Chemistry", vol. 14, No. 5; (1971) pp. 465-466.
Takeaki Ohsu et al., "Journal of Biological Chemistry", vol. 285, No. 2, (2010) pp. 1016-1022.
Thomas A. Kirkland et al., "Bioorganic & Medicinal Chemistry", vol. 16, (2008) pp. 4963-4983.
Ioan Cristea et al., Revue Roumaine de Chimie, vol. 39, No. 12, (1994) pp. 1435-1441.
Carol W. Mosher et al., "J. Org. Chem", vol. 23 (1958) pp. 1257-1259.
U.S. Appl. No. 13/624,254, filed Sep. 21, 2012, Sugiki, et al.
Extended European Search Report issued Apr. 1, 2014, in European Patent Application No. 11750799.6.

US 9,253,997 B2

ALKYLAMINE DERIVATIVE

TECHNICAL FIELD

The present invention relates to an alkylamine derivative or a salt thereof, and a pharmaceutical agent comprising the same. More particularly, the present invention relates to a CaSR agonistic agent, a prophylactic or therapeutic agent for a disease that can be ameliorated through CaSR activation, a prophylactic or therapeutic agent for hyperparathyroidism, diarrhea and peptic ulcer, and seasonings and an agent for imparting kokumi, which have an alkylamine derivative or a pharmaceutically acceptable salt thereof as an active ingredient.

BACKGROUND ART

The calcium receptor, also called the calcium sensing receptor (also referred to as "CaSR"), was cloned from bovine thyroid in 1993 as G-protein coupled seven-transmembrane receptor (G-protein coupled receptor; GPCR) that senses extracellular calcium (Ca2+) (Non-patent Document 1). The calcium receptor has a function of altering the intracellular Ca2+ concentration by sensing extracellular Ca2+, thereby regulating production of hormones or the like involved in Ca2+ metabolic regulation, as typified by parathyroid hormone.

Recently, cinacalcet (CCT), a calcium receptor agonist, was found to have an action of suppressing secretion of parathyroid hormone by acting on the calcium receptor of parathyroid to enhance Ca2+ sensitivity of the calcium receptor (Non-patent Document 2), and it has been marketed as a therapeutic drug for secondary hyperparathyroidism of dialysis patients (Non-patent Document 3).

In addition, the calcium receptor was also found to be expressed in kidney, brain, thyroid, bones and digestive tracts, and thus considered to be involved in various diseases.

As compounds having a CaSR activating effect, other than glutathione, for example, gamma-glutamyl peptide derivatives (Non-patent Documents 4 and 9), pyrrolidine derivatives (Patent Document 1) and the like are known. In addition, CaSR agonists such as a gamma-glutamyl peptide derivative have been reported to be useful as a prophylactic or therapeutic agent for diarrhea (Patent Document 2), a prophylactic or therapeutic agent for acid secretion-related diseases such as gastric ulcer, duodenal ulcer and reflux esophagitis (Patent Document 3), a therapeutic agent for diabetes or obesity (Patent Document 4), and further as an immunostimulator (Patent Document 5). Furthermore, Patent Document 6 and Non-patent Document 9 describe that compounds having CaSR agonistic activity are also useful as agent for imparting kokumi.

These compounds, however, are structurally different from the alkylamine derivatives of the present invention.

Meanwhile, a gamma-glutamyl anilide derivative, among the alkylamine derivatives, is known to be used as a substrate for enzymatic activity (Non-patent Document 5 and Patent Document 7) as well as for its application as an antimicrobial agent or an anti-allergic agent (Non-patent Document 6 and Patent Document 8) and its application as an analytical reagent (Non-patent Documents 7 and 11). Moreover, an L-2-amino-3-N'-substituted ureidopropanoic acid derivative is known for its application as a synthetic intermediate of an asparagine analog employed as an anticancer agent (Non-patent Document 8). The alkylamine derivative is known as a leukotriene A4 inhibitor for application against inflammatory diseases (Non-patent Document 10). The alkylamine derivative is also known for its application as an anticancer agent (Non-patent Document 12).

The above-mentioned compounds, however, have not been known for their applications as pharmaceutical agents with a CaSR agonistic effect or applications as seasonings.

PRIOR ART DOCUMENTS

Patent Documents
[Patent Document 1] International Patent Application Publication (pamphlet) No. WO2006/123725
[Patent Document 2] International Patent Application Publication (pamphlet) No. WO2008/139947
[Patent Document 3] International Patent Application Publication (pamphlet) No. WO2009/119554
[Patent Document 4] International Patent Application Publication (pamphlet) No. WO2009/107660
[Patent Document 5] International Patent Application Publication (pamphlet) No. WO2009/128523
[Patent Document 6] International Patent Application Publication (pamphlet) No. WO2007/055393
[Patent Document 7] International Patent Application Publication (pamphlet) No. WO2007/055393
[Patent Document 8] Japanese Unexamined Patent Application No. Heisei 06-172287
Non-Patent Documents
[Non-patent Document 1] Nature, 366: 575-580 (1993)
[Non-patent Document 2] Current Opinion in Pharmacology, 2: 734-739 (2002)
[Non-patent Document 3] Ethical drug package insert (5th ed., revised January 2010) for "REGPARA™ tablet 25 mg/REGPARA™ tablet 75 mg"
[Non-patent Document 4] Journal of Biological Chemistry, 281(13), 8864-70 (2006)
[Non-patent Document 5] Clinical Chemistry, 22, 2051 (1976)
[Non-patent Document 6] Journal of Medicinal Chemistry, 8(3), 398-400 (1965)
[Non-patent Document 7] Analytica Chimica Acta, 519(2), 181-187 (2004)
[Non-patent Document 8] Journal of Medicinal Chemistry, 14(5), 465-466 (1971)
[Non-patent Document 9] Journal of Biological Chemistry, 285 (2), 1016-22 (2010)
[Non-patent Document 10] Bioorganic & Medicinal Chemistry, 16, 4863-4983 (2008)
[Non-patent Document 11] Revue Roumaine de Chimie, 39(12), 1435-41 (1994)
[Non-patent Document 12] J. Org. Chem., 23, 1257-1259 (1958)

SUMMARY OF THE INVENTION

Problem to be Solved by the Invention

A pharmaceutical agent that has a superior CaSR agonistic effect and that is highly safe is desired to be provided. In addition, high-performance seasonings that imparts kokumi is also desired to be provided.

Means for Solving the Problem

As a result of search for a CaSR agonist, the present inventors found that an alkylamine derivative of the present invention has a superior CaSR agonistic effect and was effective for various disease models, thereby accomplishing the present invention.

Thus, the present invention is as follows.

[1] A compound represented by the following Formula (I) or a salt thereof:

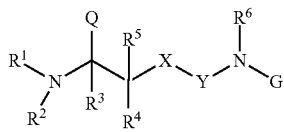

[wherein, $R^1$ and $R^2$, each independently, represent a hydrogen atom, substituted or unsubstituted $C_{1-6}$ alkyl, substituted or unsubstituted $C_{2-6}$ alkenyl or substituted or unsubstituted $C_{2-6}$ alkynyl, or $R^1$ and $R^2$ may integrally form a substituted or unsubstituted 5- or 6-membered hetero ring which may further include a heteroatom(s);

$R^3$ represents a hydrogen atom, halogeno or substituted or unsubstituted $C_{1-6}$ alkyl;

$R^4$ and $R^5$, each independently, represent a hydrogen atom, substituted or unsubstituted $C_{1-6}$ alkyl, substituted or unsubstituted $C_{2-6}$ alkenyl, substituted or unsubstituted $C_{2-6}$ alkynyl or halogeno;

X represents $CR^aR^b$, an oxygen atom, $NR^c$ or a sulfur atom (wherein, $R^a$ and $R^b$, each independently, represent a hydrogen atom, $C_{1-6}$ alkyl or halogeno, and $R^c$ represents a hydrogen atom or $C_{1-6}$ alkyl);

Y represents C=O, SO, $SO_2$, C=S or $C=NR^d$ (wherein $R^d$ represents a hydrogen atom or $C_{1-6}$ alkyl, and $R^d$ and $R^6$ may integrally form a substituted or unsubstituted 5- or 6-membered hetero ring);

$R^6$ represents a hydrogen atom, substituted or unsubstituted $C_{1-6}$ alkyl, substituted or unsubstituted $C_{2-6}$ alkenyl, substituted or unsubstituted $C_{2-6}$ alkynyl or hydroxy;

G represents $R^7$-substituted aryl or $R^7$-substituted heteroaryl, where the $R^7$-substituted aryl or the $R^7$-substituted heteroaryl may further be substituted with one or more $R^8$;

$R^7$ represents sulfo, carboxyl or phosphono;

$R^8$ represents substituted or unsubstituted $C_{1-6}$ alkyl, substituted or unsubstituted $C_{2-6}$ alkenyl, substituted or unsubstituted $C_{2-6}$ alkynyl, halogeno, hydroxy, substituted or unsubstituted $C_{1-6}$ alkoxy, nitro, amino, mono-$C_{1-6}$ alkylamino, di-$C_{1-6}$ alkylamino, sulfo, carboxyl, phosphono, $C_{1-3}$ alkylcarbonylamino or mono-$C_{1-6}$ alkylphosphono, where they may be different when more than one $R^8$ exist;

Q represents a hydrogen atom, substituted or unsubstituted $C_{1-6}$ alkyl, substituted or unsubstituted $C_{2-6}$ alkenyl, substituted or unsubstituted $C_{2-6}$ alkynyl, carboxyl, $CONR^eR^f$, $CONHNHR^g$, $COR^h$, substituted or unsubstituted aryl or substituted or unsubstituted heteroaryl;

$R^e$ and $R^f$, each independently, represent a hydrogen atom, substituted or unsubstituted $C_{1-6}$ alkyl, substituted or unsubstituted $C_{1-6}$ alkylsulfonyl, substituted or unsubstituted arylsulfonyl, substituted or unsubstituted $C_{3-8}$ cycloalkyl, hydroxy or $C_{1-6}$ alkoxy, or alternatively, $R^e$ and $R^f$ may integrally form a substituted or unsubstituted 5- or 6-membered hetero ring which may further have a heteroatom(s);

$R^g$ represents substituted or unsubstituted $C_{1-6}$ alkylcarbonyl, substituted or unsubstituted benzoyl, substituted or unsubstituted aryl or substituted or unsubstituted heteroaryl; and $R^h$ represents substituted or unsubstituted $C_{1-6}$ alkoxy, substituted or unsubstituted mercapto, or the following group:

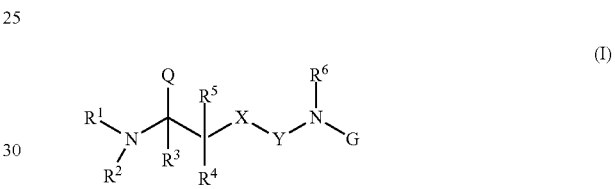

(wherein Z represents a bivalent group of substituted or unsubstituted $C_{1-6}$ hydrocarbon; $E^1$ represents substituted or unsubstituted $C_{1-6}$ acyloxy, substituted or unsubstituted $C_{1-6}$ alkoxycarbonyloxy, substituted or unsubstituted amino, carboxyl, substituted or unsubstituted $C_{1-6}$ alkoxycarbonyl, halogeno, aryl, heteroaryl, substituted or unsubstituted $C_{1-6}$ alkoxy or substituted or unsubstituted carbamoyl; $E^2$ represents a hydrogen atom or $C_{1-6}$ alkyl; and Z and $E^1$ may integrally form a ring), provided that when X is methylene or an oxygen atom, Y is C=O all of $R^1$-$R^5$ are hydrogen atoms and G is phenyl, Q is a group other than carboxyl or $COR^h$].

[2] The compound according to [1] above, represented by the following Formula (I), or a salt thereof:

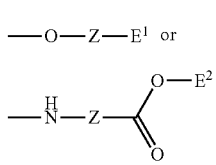

[wherein, $R^1$ and $R^2$, each independently, represent a hydrogen atom, substituted or unsubstituted $C_{1-6}$ alkyl, substituted or unsubstituted $C_{2-6}$ alkenyl or substituted or unsubstituted $C_{2-6}$ alkynyl, or $R^1$ and $R^2$ may integrally form a substituted or unsubstituted 5- or 6-membered hetero ring which may further include a heteroatom(s);

$R^3$ represents a hydrogen atom, halogeno or substituted or unsubstituted $C_{1-6}$ alkyl;

$R^4$ and $R^5$, each independently, represent a hydrogen atom, substituted or unsubstituted $C_{1-6}$ alkyl, substituted or unsubstituted $C_{2-6}$ alkenyl, substituted or unsubstituted $C_{2-6}$ alkynyl or halogeno;

X represents $CR^aR^b$, an oxygen atom, $NR^c$ or a sulfur atom (wherein, $R^a$ and $R^b$, each independently, represent a hydrogen atom, $C_{1-6}$ alkyl or halogeno, and $R^c$ represents a hydrogen atom or $C_{1-6}$ alkyl);

Y represents C=O, SO, $SO_2$, C=S or $C=NR^d$ (wherein $R^d$ represents a hydrogen atom or $C_{1-6}$ alkyl, and $R^d$ and $R^6$ may integrally form a substituted or unsubstituted 5- or 6-membered hetero ring);

$R^6$ represents a hydrogen atom, substituted or unsubstituted $C_{1-6}$ alkyl, substituted or unsubstituted $C_{2-6}$ alkenyl, substituted or unsubstituted $C_{2-6}$ alkynyl or hydroxy;

G represents $R^7$-substituted aryl or $R^7$-substituted heteroaryl, where the $R^7$-substituted aryl or the $R^7$-substituted heteroaryl may further be substituted with one or more $R^8$;

$R^7$ represents sulfo, carboxyl or phosphono;

$R^8$ represents substituted or unsubstituted $C_{1-6}$ alkyl, substituted or unsubstituted $C_{2-6}$ alkenyl, substituted or unsubstituted $C_{2-6}$ alkynyl, halogeno, hydroxy, substituted or unsubstituted $C_{1-6}$ alkoxy, nitro, amino, mono-$C_{1-6}$ alkylamino, di-$C_{1-6}$ alkylamino, sulfo, carboxyl, phosphono or mono-$C_{1-6}$ alkylphosphono, where they may be different when more than one $R^8$ exist;

Q represents a hydrogen atom, substituted or unsubstituted $C_{1-6}$ alkyl, substituted or unsubstituted $C_{2-6}$ alkenyl, substituted or unsubstituted $C_{2-6}$ alkynyl, carboxyl, $CONR^eR^f$, $CONHNHR^g$, $COR^h$, substituted or unsubstituted aryl or substituted or unsubstituted heteroaryl;

$R^e$ and $R^f$, each independently, represent a hydrogen atom, substituted or unsubstituted $C_{1-6}$ alkyl, substituted or unsubstituted $C_{1-6}$ alkylsulfonyl, substituted or unsubstituted arylsulfonyl, substituted or unsubstituted $C_{3-8}$ cycloalkyl, hydroxy or $C_{1-6}$ alkoxy, or alternatively, $R^e$ and $R^f$ may integrally form a substituted or unsubstituted 5- or 6-membered hetero ring which may further have a heteroatom(s);

$R^g$ represents substituted or unsubstituted $C_{1-6}$ alkylcarbonyl, substituted or unsubstituted benzoyl, substituted or unsubstituted aryl, or substituted or unsubstituted heteroaryl; and $R^h$ represents substituted or unsubstituted $C_{1-6}$ alkoxy, substituted or unsubstituted mercapto, or the following group:

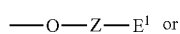 (IIa)

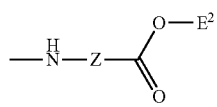 (IIb)

(wherein Z represents a bivalent group of substituted or unsubstituted $C_{1-6}$ hydrocarbon; $E^1$ represents substituted or unsubstituted $C_{1-6}$ acyloxy, substituted or unsubstituted $C_{1-6}$ alkoxycarbonyloxy, substituted or unsubstituted amino, carboxyl, substituted or unsubstituted $C_{1-6}$ alkoxycarbonyl, halogeno, aryl, heteroaryl, substituted or unsubstituted $C_{1-6}$ alkoxy or substituted or unsubstituted carbamoyl; $E^2$ represents a hydrogen atom or $C_{1-6}$ alkyl; and Z and $E^1$ may integrally form a ring), provided that when X is methylene or an oxygen atom, Y is $C=O$, all of $R^1$-$R^5$ are hydrogen atoms and G is phenyl, Q is a group other than carboxyl or $COR^h$].

[3] A pharmaceutical agent comprising the compound or a pharmaceutically acceptable salt thereof according to [1] or [2] above as an active ingredient.

[4] A CaSR agonistic agent comprising a compound represented by the following Formula ($I^0$) or a pharmaceutically acceptable salt thereof as an active ingredient:

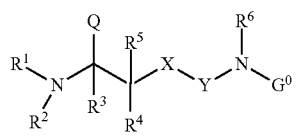 ($I^0$)

[wherein, $R^1$ and $R^2$, each independently, represent a hydrogen atom, substituted or unsubstituted $C_{1-6}$ alkyl, substituted or unsubstituted $C_{2-6}$ alkenyl or substituted or unsubstituted $C_{2-6}$ alkynyl, or $R^1$ and $R^2$ may integrally form a substituted or unsubstituted 5- or 6-membered hetero ring which may further include a heteroatom(s);

$R^3$ represents a hydrogen atom, halogeno or substituted or unsubstituted $C_{1-6}$ alkyl;

$R^4$ and $R^5$, each independently, represent a hydrogen atom, substituted or unsubstituted $C_{1-6}$ alkyl, substituted or unsubstituted $C_{2-6}$ alkenyl, substituted or unsubstituted $C_{2-6}$ alkynyl or halogeno;

X represents $CR^aR^b$, an oxygen atom, $NR^c$ or a sulfur atom (wherein, $R^a$ and $R^b$, each independently, represent a hydrogen atom, $C_{1-6}$ alkyl or halogen, and $R^c$ represents a hydrogen atom or $C_{1-6}$ alkyl);

Y represents $C=O$, SO, $SO_2$, $C=S$ or $C=NR^d$ (wherein $R^d$ represents a hydrogen atom or $C_{1-6}$ alkyl, and $R^d$ and $R^6$ may integrally form a substituted or unsubstituted 5- or 6-membered hetero ring);

$R^6$ represents a hydrogen atom, substituted or unsubstituted $C_{1-6}$ alkyl, substituted or unsubstituted $C_{2-6}$ alkenyl, substituted or unsubstituted $C_{2-6}$ alkynyl or hydroxy;

$G^0$ represents aryl that is unsubstituted or substituted with one or more $R^{70}$ or heteroaryl that is unsubstituted or substituted with one or more $R^{70}$, where the $R^{70}$-substituted aryl or the $R^{70}$-substituted heteroaryl may further be substituted;

$R^{70}$ represents substituted or unsubstituted $C_{1-6}$ alkyl, substituted or unsubstituted $C_{2-6}$ alkenyl, substituted or unsubstituted $C_{2-6}$ alkynyl, halogeno, hydroxy, substituted or unsubstituted $C_{1-6}$ alkoxy, nitro, amino, mono-$C_{1-6}$ alkylamino, di-$C_{1-6}$ alkylamino, sulfo, carboxyl, phosphono, $C_{1-3}$ alkylcarbonylamino or mono-$C_{1-6}$ alkylphosphono, where they may be different when more than one $R^{70}$ exist;

Q represents a hydrogen atom, substituted or unsubstituted $C_{1-6}$ alkyl, substituted or unsubstituted $C_{2-6}$ alkenyl, substituted or unsubstituted $C_{2-6}$ alkynyl, carboxyl, $CONR^eR^f$, $CONHNHR^g$, $COR^h$, substituted or unsubstituted aryl or substituted or unsubstituted heteroaryl;

$R^e$ and $R^f$, each independently, represent a hydrogen atom, substituted or unsubstituted $C_{1-6}$ alkyl, substituted or unsubstituted $C_{1-6}$ alkylsulfonyl, substituted or unsubstituted arylsulfonyl, substituted or unsubstituted $C_{3-8}$ cycloalkyl, hydroxy or $C_{1-6}$ alkoxy, or alternatively, $R^e$ and $R^f$ may integrally form a substituted or unsubstituted 5- or 6-membered hetero ring which may further have a heteroatom(s);

$R^g$ represents substituted or unsubstituted $C_{1-6}$ alkylcarbonyl, substituted or unsubstituted benzoyl, substituted or unsubstituted aryl, or substituted or unsubstituted heteroaryl; and $R^h$ represents substituted or unsubstituted $C_{1-6}$ alkoxy, substituted or unsubstituted mercapto, or the following group:

 (IIa)

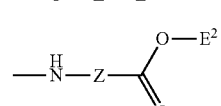 (IIb)

(wherein Z represents a bivalent group of substituted or unsubstituted $C_{1-6}$ hydrocarbon; E' represents substituted or unsubstituted $C_{1-6}$ acyloxy, substituted or unsubstituted $C_{1-6}$ alkoxycarbonyloxy, substituted or unsubstituted amino, carboxyl, substituted or unsubstituted $C_{1-6}$ alkoxycarbonyl, halogeno, aryl, heteroaryl, substituted or unsubstituted $C_{1-6}$ alkoxy or substituted or unsubstituted carbamoyl; $E^2$ represents a hydrogen atom or $C_{1-6}$ alkyl; and Z and $E^1$ may integrally form a ring), provided that when X is methylene or an oxygen atom, Y is $C=O$, all of $R^1$-$R^5$ are hydrogen atoms, and G is phenyl, then, Q is a group other than carboxyl or $COR^h$].

[5] The CaSR agonistic agent according to [4] above, comprising a compound represented by the following Formula (I⁰) or a pharmaceutically acceptable salt thereof as an active ingredient:

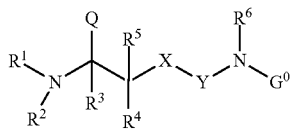

(I⁰)

[wherein, $R^1$ and $R^2$, each independently, represent a hydrogen atom, substituted or unsubstituted $C_{1-6}$ alkyl, substituted or unsubstituted $C_{2-6}$ alkenyl or substituted or unsubstituted $C_{2-6}$ alkynyl, or $R^1$ and $R^2$ may integrally form a substituted or unsubstituted 5- or 6-membered hetero ring which may further include a heteroatom(s);

$R^3$ represents a hydrogen atom, halogeno or substituted or unsubstituted $C_{1-6}$ alkyl;

$R^4$ and $R^5$, each independently, represent a hydrogen atom, substituted or unsubstituted $C_{1-6}$ alkyl, substituted or unsubstituted $C_{2-6}$ alkenyl, substituted or unsubstituted $C_{2-6}$ alkynyl or halogeno;

X represents $CR^aR^b$, an oxygen atom, $NR^c$ or a sulfur atom (wherein, $R^a$ and $R^b$, each independently, represent a hydrogen atom, $C_{1-6}$ alkyl or halogeno, and $R^c$ represents a hydrogen atom or $C_{1-6}$ alkyl);

Y represents C=O, SO, $SO_2$, C=S or C=$NR^d$ (wherein $R^d$ represents a hydrogen atom, $C_{1-6}$ alkyl, $R^d$ and $R^6$ may integrally form a substituted or unsubstituted 5- or 6-membered hetero ring);

$R^6$ represents a hydrogen atom, substituted or unsubstituted $C_{1-6}$ alkyl, substituted or unsubstituted $C_{2-6}$ alkenyl, substituted or unsubstituted $C_{2-6}$ alkynyl or hydroxy;

$G^0$ represents unsubstituted or substituted aryl with one or more $R^{70}$ or unsubstituted or substituted heteroaryl with one or more $R^{70}$, where the $R^{70}$-substituted aryl or the $R^{70}$-substituted heteroaryl may further be substituted;

$R^{70}$ represents substituted or unsubstituted $C_{1-6}$ alkyl, substituted or unsubstituted $C_{2-6}$ alkenyl, substituted or unsubstituted $C_{2-6}$ alkynyl, halogeno, hydroxy, substituted or unsubstituted $C_{1-6}$ alkoxy, nitro, amino, mono-$C_{1-6}$ alkylamino, di-$C_{1-6}$ alkylamino, sulfo, carboxyl, phosphono or mono-$C_{1-6}$ alkylphosphono, where they may be different when more than one $R^{70}$ exist;

Q represents a hydrogen atom, substituted or unsubstituted $C_{1-6}$ alkyl, substituted or unsubstituted $C_{2-6}$ alkenyl, substituted or unsubstituted $C_{2-6}$ alkynyl, carboxyl, $CONR^eR^f$, $CONHNHR^g$, $COR^h$, substituted or unsubstituted aryl or substituted or unsubstituted heteroaryl;

$R^e$ and $R^f$, each independently, represent a hydrogen atom, substituted or unsubstituted $C_{1-6}$ alkyl, substituted or unsubstituted $C_{1-6}$ alkylsulfonyl, substituted or unsubstituted arylsulfonyl, substituted or unsubstituted $C_{3-8}$ cycloalkyl, hydroxy or $C_{1-6}$ alkoxy, or alternatively, $R^e$ and $R^f$ may integrally form a substituted or unsubstituted 5- or 6-membered hetero ring which may further have a heteroatom(s);

$R^h$ represents substituted or unsubstituted $C_{1-6}$ alkylcarbonyl, substituted or unsubstituted benzoyl, substituted or unsubstituted aryl, or substituted or unsubstituted heteroaryl; and $R^h$ represents substituted or unsubstituted $C_{1-6}$ alkoxy, substituted or unsubstituted mercapto, or the following group:

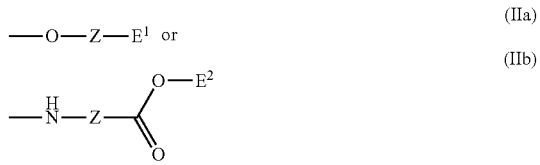

(IIa)
(IIb)

(wherein Z represents a bivalent group of substituted or unsubstituted $C_{1-6}$ hydrocarbon; $E^1$ represents substituted or unsubstituted $C_{1-6}$ acyloxy, substituted or unsubstituted $C_{1-6}$ alkoxycarbonyloxy, substituted or unsubstituted amino, carboxyl, substituted or unsubstituted $C_{1-6}$ alkoxycarbonyl, halogeno, aryl, heteroaryl, substituted or unsubstituted $C_{1-6}$ alkoxy or substituted or unsubstituted carbamoyl; $E^2$ represents a hydrogen atom or $C_{1-6}$ alkyl; and Z and $E^1$ may integrally form a ring), provided that when X is methylene or an oxygen atom, Y is C=O, all of $R^1$-$R^5$ are hydrogen atoms, and G is phenyl, then, Q is a group other than carboxyl or $COR^h$].

[5-2] The CaSR agonistic agent according to either one of [4] and [5] above, which is a prophylactic or therapeutic agent for hyperparathyroidism.

[5-3] The CaSR agonistic agent according to either one of [4] and [5] above, which is a prophylactic or therapeutic agent for diarrhea.

[5-4] The CaSR agonistic agent according to either one of [4] and [5] above, which is a prophylactic or therapeutic agent for peptic ulcer.

[5-5] The CaSR agonistic agent according to either one of [4] and [5] above, which is an agent for imparting kokumi.

[6] The pharmaceutical agent according to [3] above, which is a prophylactic or therapeutic agent for a disease that is ameliorated through CaSR activation.

[7] The pharmaceutical agent according to [3] above, which is a prophylactic or therapeutic agent for hyperparathyroidism.

[8] The pharmaceutical agent according to [3] above, which is a prophylactic or therapeutic agent for diarrhea.

[9] The pharmaceutical agent according to [3] above, which is a prophylactic or therapeutic agent for peptic ulcer.

[10] Seasonings comprising the compound or an edible salt thereof according to [1] or [2] above as an active ingredient.

[11] A agent for imparting kokumi comprising the compound or an edible salt thereof according to either one of [1] and [2] above as an active ingredient.

Effect of the Invention

An alkylamine derivative of the present invention has a superior CaSR agonistic effect, and useful, for example, as a prophylactic or therapeutic agent for a disease that is ameliorated through CaSR activation, in particular, as a prophylactic or therapeutic agent for hyperparathyroidism, diarrhea or peptic ulcer, and as seasonings or an agent for imparting kokumi.

EMBODIMENTS FOR CARRYING OUT THE INVENTION

Figure 1:
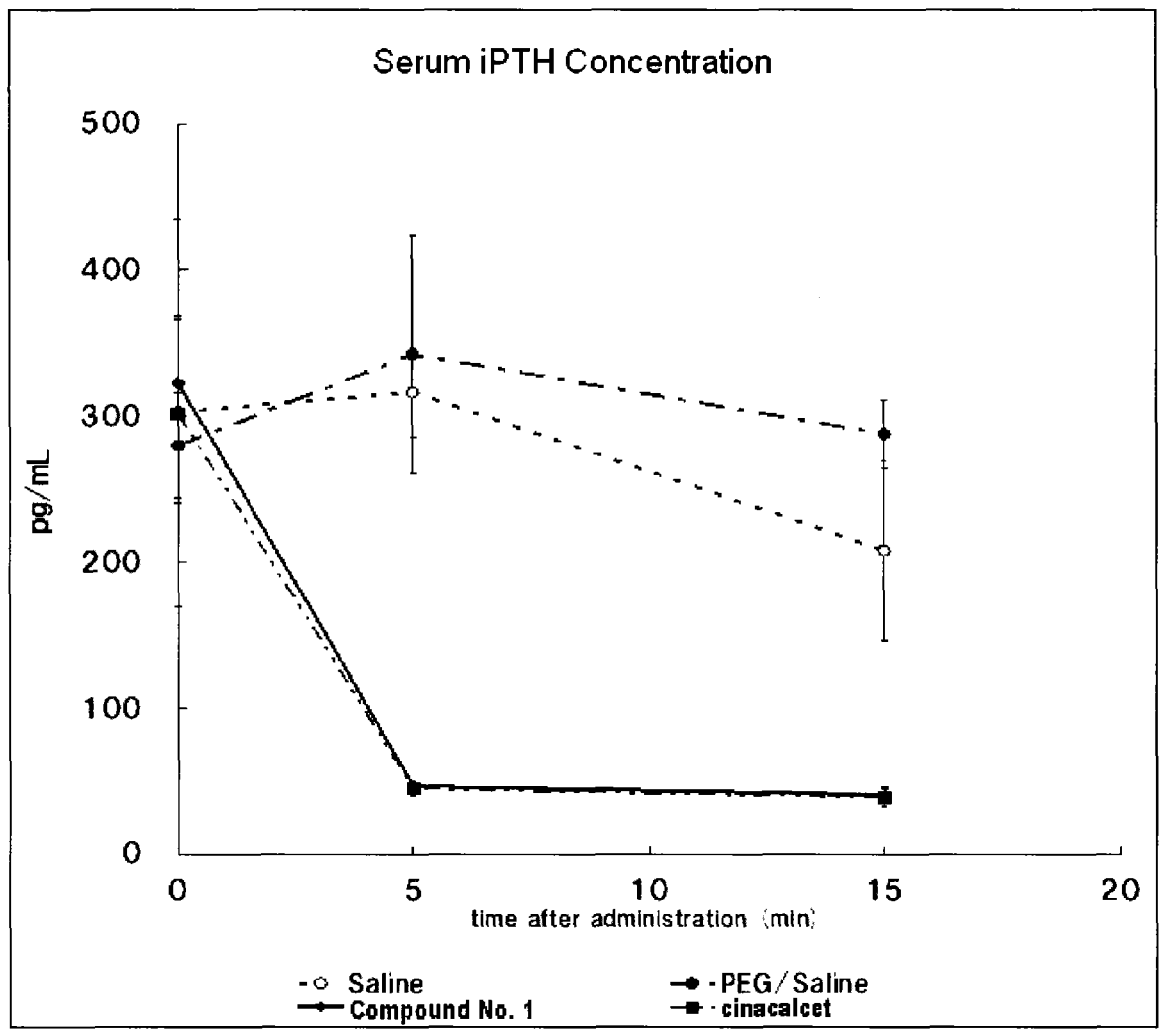
FIG. 1 A graph comparing the effects of Compound No. 1 and cinacalcet with respect to serum iPTH concentration.

Hereinafter, definitions of the groups of the compounds represented by Formulae (I) and (I⁰) will be described.

Herein, "$C_{1-6}$ alkyl" is a monovalent group derived by removing any one hydrogen atom from a linear- or branched-chain aliphatic hydrocarbon having 1-6 carbons. Specific examples include methyl, ethyl, isopropyl, butyl, n-butyl, isobutyl, sec-butyl, t-butyl, pentyl, isopentyl, 2,3-dimethyl-propyl and hexyl. Preferably, it is $C_{1-3}$ alkyl.

"$C_{2-6}$ alkenyl" is a monovalent group with at least one double bond (two adjacent sp2 carbon atoms) among the linear- or branched-chain aliphatic hydrocarbon groups having 1-6 carbons. Specific examples of $C_{2-6}$ alkenyl include vinyl, allyl, 1-propenyl, 2-propenyl, 1-butenyl, 2-butenyl (including cis and trans), 3-butenyl, pentenyl and hexenyl. Preferably, it is $C_{2-3}$ alkenyl.

"$C_{2-6}$ alkynyl" is a monovalent group with at least one triple bond (two adjacent sp carbon atoms) among the linear- or branched-chain aliphatic hydrocarbon groups having 1-6 carbons. Specific examples include ethynyl, 1-propynyl, propargyl and 3-butynyl. Preferably, it may be $C_{2-3}$ alkynyl.

"Halogeno" refers to fluorine, chlorine, bromine, iodine atoms and the like.

"Aryl" refers to an aromatic hydrocarbon ring group such as phenyl and naphthyl. Preferably, it is phenyl.

"Heteroaryl" refers to a 5- to 10-membered aromatic hetero ring group containing one to four heteroatoms selected from N, S and O, Specific examples of the aromatic hetero ring include pyridine, pyridazine, pyrazine, pyrimidine, thiazole, isothiazole, oxazole, isooxazole, oxadiazole, pyrazole, imidazole, furan, thiophene and pyrrol. Preferably, it is pyridine, imidazole, thiophene, oxadiazole or indole. It is preferably a 5- to 6-membered aromatic hetero ring and particularly pyridine or pyrimidine.

"$C_{1-6}$ alkoxy" refers to $C_{1-6}$ alkyl-O—. Specifically, examples include methoxy, ethoxy, 1-propoxy, 2-propoxy, n-butoxy, i-butoxy, sec-butoxy, t-butoxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy and 3-hexyloxy. Preferably, it is $C_{1-3}$ alkoxy.

Examples of "$C_{3-8}$ cycloalkyl" include cyclopropyl, cyclopentyl, cyclohexyl and cycloheptyl. Preferably, it is $C_{5-7}$ cycloalkyl.

"Mono-$C_{1-6}$ alkylamino" is an amino group having one hydrogen atom on the nitrogen atom substituted with the above-described $C_{1-6}$ alkyl, and refers to $C_{1-6}$ alkyl-NH—. Specific examples include methylamino and ethylamino. Preferably, it is mono-$C_{1-3}$ alkylamino.

"Di-$C_{1-6}$ alkylamino" is an amino group where each of two hydrogen atoms on the nitrogen atom is substituted with the above-described $C_{1-6}$ alkyl, and refers to ($C_{1-6}$ alkyl)$_2$N—. The $C_{1-6}$ alkyl groups may be identical to or different from each other. Specific examples include dimethylamino and diethylamino. Preferably, it is di-$C_{1-3}$ alkylamino.

"$C_{1-3}$ alkylcarbonylamino" refers to a group represented by $C_{1-3}$ alkyl-C(O)—NH—. Examples of $C_{1-3}$ alkylcarbonylamino include groups such as acetylamino and propionylamino. Preferably, it is acetylamino.

"Mono-$C_{1-6}$ alkylphosphono" is a phosphono group where one hydrogen atom on the hydroxyl group is substituted with the above-described $C_{1-8}$ alkyl, and refers to —PO$_3$H ($C_{1-6}$ alkyl). Specific examples include methylphosphono and ethylphosphono. Preferably, it is mono-$C_{1-3}$ alkylphosphono.

"$C_{1-6}$ alkylsulfonyl" refers to a group represented by $C_{1-6}$ alkyl-S(O)$_2$—, and specific examples include methylsulfonyl and ethylsulfonyl. Preferably, it is $C_{1-3}$ alkylsulfonyl.

"Arylsulfonyl" refers to a group represented by aryl-S(O)$_2$—, and a specific example includes phenylsulfonyl.

"$C_{1-6}$ alkylcarbonyl" refers to a group represented by $C_{1-6}$ alkyl-C(O)—, and specific examples include methylcarbonyl and ethylcarbonyl. Preferably, it is $C_{1-3}$ alkylcarbonyl.

"$C_{1-6}$ alkoxycarbonyloxy" refers to a group represented by $C_{1-6}$ alkyl-O—C(O)—O—, and examples include methoxycarbonyloxy and ethoxycarbonyloxy. Preferably, it is $C_{1-3}$ alkoxycarbonyloxy.

A "bivalent group of $C_{1-6}$ hydrocarbon" refers to a bivalent group derived by removing any two hydrogen atoms from a linear- or branched-chain aliphatic hydrocarbon that has 1-6 carbons and that may contain one to several double or triple bonds. Specific examples include methylene, ethane-1,1-diyl, vinylene, ethynylene and propargyl.

"$C_{1-6}$ acyloxy" refers to a group represented by $C_{1-6}$ alkyl-C(O)—O—, $C_{3-6}$ cycloalkyl-C(O)—O— or aryl-C(O)—O—. Examples of $C_{1-6}$ acyloxy include groups such as acetyloxy, propionyloxy, cyclohexylcarbonyloxy and benzoyloxy. It is preferably $C_{1-6}$ alkyl-C(O)—O— and more preferably $C_{1-3}$ alkyl-C(O)—O—.

"$C_{1-6}$ alkoxycarbonyl" refers to a group represented by $C_{1-6}$ alkyl-O—C(O)—, and examples include methoxycarbonyl and ethoxycarbonyl. Preferably, it is $C_{1-3}$ alkoxycarbonyl.

"5- or 6-membered hetero ring that may further contain a heteroatom(s)", formed integrally with $R^1$ and $R^2$ or $R^e$ and $R^f$, refers to a saturated or unsaturated 5- or 6-membered hetero ring that may further have, other than the nitrogen atom bound by $R^1$ and $R^2$ or $R^e$ and $R^f$, 1-3 heteroatoms selected from a nitrogen atom, an oxygen atom and a sulfur atom as constituent atoms of the ring Examples of the saturated 5- or 6-membered hetero ring group include pyrrolidine-1-yl, pyrazolidine-1-yl, imidazolidine-1-yl, piperidine-1-yl, piperazine-1-yl, morpholine-4-yl and thiomorpholine-4-yl.

Examples of the unsaturated 5- or 6-membered hetero ring group include pyrrol-1-yl, 2-pyrroline-1-yl, 3-pyrroline-1-yl, pyrazole-1-yl, imidazole-1-yl, 2-pyrazoline-1-yl, 3-pyrazoline-1-yl, 2-imidazoline-1-yl, 1,2,3-triazole-1-yl, 1,2,4-triazole-1-yl, tetrazole-1-yl, 1,4-oxazine-4-yl and 1,4-thiazine-1-yl.

A "5- or 6-membered hetero ring" formed integrally with $R^d$ and $R^6$ refers to a saturated or unsaturated 5- or 6-membered hetero ring which includes N=C—N bound by $R^d$ and $R^6$ as a part of the ring, and may further contain 1-3 heteroatoms selected from a nitrogen atom, an oxygen atom and a sulfur atom as constituent atoms of the ring. Specific examples include 2-imidazolidine, imidazole, triazole, tetrazole, 1,4,5,6-tetrahydropyrimidine, 1,4-dihydropyrimidine, 1,6-dihydropyrimidine and 2H-1,2,4-oxadiazine.

The phrase "which may further substituted" used for $G^o$ means that substitution, for example, with a substituent such as cyano, substituted or unsubstituted mercapto, $C_{1-6}$ alkyl-C(O)—, $C_{1-6}$ alkyl-C(O)—O—, $C_{3-6}$ cycloalkyl, $C_{1-6}$ alkyl-O—C(O)—$C_{1-6}$ alkylene-O—, substituted or unsubstituted aryl, substituted or unsubstituted aryl-O—, substituted or unsubstituted aryl-C(O)—, —O—$C_{1-6}$ alkylene-O—, substituted or unsubstituted aryl-$C_{1-6}$ alkenyl- may take place at a position which may have a substituent(s) other than $R^{70}$.

Here, $C_{1-6}$ alkylene refers to a bivalent group of the above-described $C_{1-6}$ alkyl.

When $R^h$ in CO—$R^h$ of Q is represented by Formula (IIa), the "ring" integrally formed with Z and $E^1$ refers to a saturated or unsaturated 5- or 6-membered ring which contains Z-$E^1$ as a part of the ring, which may further have 1-3 heteroatoms selected from a nitrogen atom, an oxygen atom and a sulfur atom as constituent atoms of the ring, and which may further condense with a benzene ring. Preferably, it is a saturated or unsaturated 5- or 6-membered ring which may have 1-3 oxygen atoms as constituent atoms of the ring.

Specific examples of $R^h$ where the ring is formed integrally with Z and $E^1$ include the following groups.

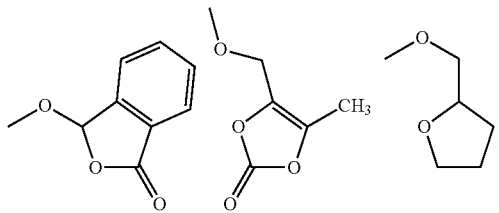

Here, the group represented by the above-described CO—$R^h$ may also represent a carboxyl group which has been subjected to prodrug modification so that it is converted into a carboxyl group in vivo as described, for example, in Prog. Med. 5: 2157-2161 (1985), "Molecular Design", *Iyakuhin No Kaihatsu* (Development of Pharmaceutical Product) Vol. 7, p. 163-198 (Hirokawa Shoten Co., 1990), or *Saisin Soyaku Kagaku* (The Practice of Medicinal Chemistry) Vol. 2, p. 271-298 (Technomics, 1999).

Examples of substituents for substituted or unsubstituted $C_{1-6}$ alkyl, $C_{2-6}$ alkenyl, $C_{2-6}$ alkynyl, $C_{1-6}$ alkoxy, $C_{1-6}$ alkylsulfonyl, $C_{1-6}$ alkylcarbonyl, mercapto, carbamoyl, amino, $C_{1-6}$ alkoxycarbonyl, the bivalent group of $C_{1-6}$ hydrocarbon, $C_{1-6}$ alkoxycarbonyloxy or $C_{1-6}$ acyloxy include a halogen atom (for example, a chlorine atom, a bromine atom and a fluorine atom), hydroxy, cyano, $C_{1-6}$ alkoxy (for example, methoxy), $C_{1-6}$ halogenoalkyl (for example, trifluoromethyl), unsubstituted or mono- or di-substituted carbamoyl with $C_{1-6}$ alkyl, unsubstituted or substituted aryl with 1 to 3 halogeno, $C_{1-6}$ alkyl, $C_{1-6}$ alkoxy or the like, and unsubstituted or substituted heteroaryl with 1 to 3 halogeno, $C_{1-6}$ alkyl, $C_{1-6}$ alkoxy or the like. Preferably, it is cyano, unsubstituted or mono- or di-substituted carbamoyl with $C_{1-6}$ alkyl, unsubstituted or substituted aryl with 1 to 3 halogeno, $C_{1-6}$ alkyl, $C_{1-6}$ alkoxy or the like, or unsubstituted or substituted heteroaryl with 1 to 3 halogeno, $C_{1-6}$ alkyl, $C_{1-6}$ alkoxy or the like. The above-mentioned groups may be 1- to 3-substituted with any substituent selected from these substituents at positions which may have a substituent(s). When there are multiple substitutions, the substituents may be different from each other.

Examples of the substituents for substituted or unsubstituted 5- or 6-membered hetero ring, substituted or unsubstituted aryl, heteroaryl or arylsulfonyl or benzoyl include a halogen atom (for example, a chlorine atom, a bromine atom and a fluorine atom), hydroxy, cyano, $C_{1-6}$ alkyl (for example, methyl or benzyl) that may be substituted with aryl (for example, phenyl), $C_{1-6}$ alkoxy (for example, methoxy), $C_{1-6}$ halogenoalkyl (for example, trifluoromethyl), carbamoyl that is optionally mono- or di-substituted with $C_{1-6}$ alkyl, and heteroaryl that may be substituted with halogen or $C_{1-6}$ alkyl. Preferable examples include $C_{1-6}$ alkyl that may be substituted with aryl (for example, phenyl) and heteroaryl that may be substituted with halogen or $C_{1-6}$ alkyl. The above-described groups may be 1- to 3-substituted with any substituent selected from these substituents at positions which may have a substituent(s). When there are multiple substitutions, the substituents may be different from each other Other than the substituents enumerated above as substituents for the substituted or unsubstituted 5- or 6-membered hetero ring, the substituent for substituted or unsubstituted $C_{3-6}$ cycloalkyl also include oxo.

$R^1$ and $R^2$ are preferably a hydrogen atom or $C_{1-6}$ alkyl, and more preferably a hydrogen atom.

$R^3$ is preferably a hydrogen atom, halogeno or $C_{1-6}$ alkyl, and more preferably a hydrogen atom.

$R^4$ and $R^5$ are preferably, a hydrogen atom, $C_{1-6}$ alkyl or halogeno, and more preferably a hydrogen atom.

X is preferably $CH_2$, an oxygen atom, NH or a sulfur atom, and more preferably NH or a sulfur atom. Particularly preferably, it is NH.

Y is preferably C=O, SO, $SO_2$ or C=S, and more preferably, C=O or C=S.

$R^6$ is preferably a hydrogen atom, hydroxy or $C_{1-6}$ alkyl, and more preferably a hydrogen atom.

G is preferably $R^7$-substituted aryl or $R^7$-substituted heteroaryl, and may further be substituted with one to three $R^8$. More preferably, it is $R^7$-substituted phenyl or $R^7$-substituted pyridyl, and may further be substituted with one to two $R^8$.

In the case where G is $R^7$-substituted phenyl where $R^7$ is sulfo, the substitution position of $R^7$ is preferably the 3-position on the phenyl group (wherein the carbon of the phenyl group which binds to the nitrogen in General Formula (I) is the 1-position). More specifically, G is preferably 5-chloro-2-hydroxy-3-sulfophenyl, 3-chloro-2-methyl-5-sulfophenyl or 3-chloro-4-methyl-5-sulfophenyl.

$G^o$ preferably represents unsubstituted or substituted aryl with one to five $R^{70}$ or unsubstituted or substituted heteroaryl with one to five $R^{70}$, and more preferably unsubstituted or substituted aryl with one to three $R^{70}$ or unsubstituted or substituted heteroaryl with one to three $R^{70}$, and most preferably unsubstituted or substituted phenyl with one to three $R^{70}$ or unsubstituted or substituted pyridyl with one to three $R^{70}$.

In the case where $G^o$ is $R^{70}$-substituted phenyl and one of $R^{70}$ is sulfo, the substitution position of $R^{70}$ is preferably the 3-position on the phenyl group (wherein the carbon in the phenyl group which binds with nitrogen in General Formula ($I^o$) is the 1-position).

$R^7$ is preferably, sulfo or carboxyl, and more preferably sulfo.

$R^{70}$ is preferably $C_{1-6}$ alkyl, $C_{2-6}$ alkenyl, $C_{2-6}$ alkynyl, halogeno, hydroxy, $C_{1-6}$ alkoxy, nitro, amino, mono-$C_{1-6}$ alkylamino, di-$C_{1-6}$ alkylamino or mono-$C_{1-6}$ alkylphosphono, more preferably $C_{1-6}$ alkyl, halogeno, hydroxy, $C_{1-6}$ alkoxy, nitro, sulfo, carboxyl or phosphono, and most preferably, $C_{1-6}$ alkyl, halogeno, hydroxy or sulfo.

$R^8$ is preferably $C_{1-6}$ alkyl, $C_{2-6}$ alkenyl, $C_{2-6}$ alkynyl, halogeno, hydroxy, $C_{1-6}$ alkoxy, nitro, amino, mono-$C_{1-6}$ alkylamino, di-$C_{1-6}$ alkylamino, sulfo, carboxyl, phosphono or mono-$C_{1-6}$ alkylphosphono, more preferably $C_{1-6}$ alkyl, halogeno, hydroxy, nitro or sulfo, and most preferably $C_{1-6}$ alkyl, halogeno or hydroxy.

Q is preferably a hydrogen atom, substituted or unsubstituted $C_{1-6}$ alkyl, carboxyl, $CONR^eR^f$, $CONHNHR^g$, $COR^h$, aryl or substituted heteroaryl, more preferably unsubstituted or substituted $C_{1-6}$ alkyl with cyano, carbamoyl or aryl, carboxyl, $CONR^eR^f$, $CONHNHR^g$, $COR^h$, aryl or substituted heteroaryl with $C_{1-6}$ alkyl, aryl-substituted $C_{1-6}$ alkyl, $C_{1-6}$ alkyl, halogeno-substituted aryl or heteroaryl, and most preferably carboxyl.

In the case where Q is a carboxyl group, $R^3$ is a hydrogen atom and X is $CR^aR^b$, an oxygen atom or $NR^c$, then, the steric structure of the carbon atoms bound with Q and $R^3$ preferably takes S-configuration. Moreover, in the case where Q is a carboxyl group, $R^3$ is a hydrogen atom and X is a sulfur atom, then, the steric structure of the carbon atoms bound with Q and $R^3$ preferably takes R-configuration.

$R^e$ and $R^f$ are preferably a hydrogen atom, substituted or unsubstituted $C_{1-6}$ alkyl, $C_{1-6}$ alkylsulfonyl, arylsulfonyl, $C_{3-6}$ cycloalkyl, hydroxy or $C_{1-6}$ alkoxy, more preferably a hydrogen atom, unsubstituted or substituted $C_{1-6}$ alkyl (with heteroaryl, aryl, halogen or $C_{1-6}$ alkoxy-substituted aryl), $C_{1-6}$ alkylsulfonyl, arylsulfonyl, hydroxy or $C_{1-6}$ alkoxy, and most preferably a hydrogen atom, unsubstituted or substituted $C_{1-6}$ alkyl (with heteroaryl or aryl), $C_{1-6}$ alkylsulfonyl or hydroxy.

$R^g$ is preferably substituted or unsubstituted $C_{1-6}$ alkylcarbonyl and more preferably unsubstituted or substituted $C_{1-6}$ alkylcarbonyl (with aryl).

$R^h$ is preferably $C_{1-6}$ alkoxy, mercapto, or the following group:

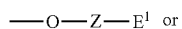 (IIa)

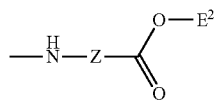 (IIb)

(wherein, Z represents a bivalent group of $C_{1-6}$ hydrocarbon, $E^1$ represents $C_{1-6}$ acyloxy, $C_{1-6}$ alkoxycarbonyloxy, amino, carboxyl, $C_{1-6}$ alkoxycarbonyl, halogeno, aryl, heteroaryl, $C_{1-6}$ alkoxy or carbamoyl, $E^2$ represents a hydrogen atom or $C_{1-6}$ alkyl, Z and $E^1$ may integrally form the following group:

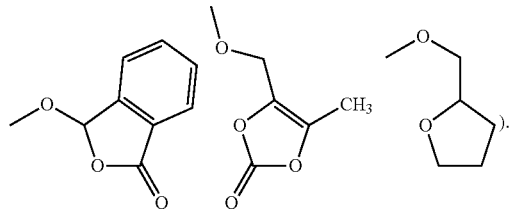

Among the compounds according to [1] above, the compound (I) of the present invention is preferably a compound represented as follows, or a salt thereof:

$R^1$ and $R^2$, each independently, represent a hydrogen atom, substituted or unsubstituted $C_{1-6}$ alkyl, substituted or unsubstituted $C_{2-6}$ alkenyl or substituted or unsubstituted $C_{2-6}$ alkynyl;

$R^4$ and $R^5$, each independently, represent a hydrogen atom;
X represents $CH_2$, an oxygen atom, NH or a sulfur atom;
Y represents C=O, SO, $SO_2$ or C=S;
G represents $R^7$-substituted aryl or $R^7$-substituted heteroaryl, where the $R^7$-substituted aryl or the $R^7$-substituted heteroaryl may further be substituted with one to five $R^8$;

$R^8$ represents substituted or unsubstituted $C_{1-6}$ alkyl, substituted or unsubstituted $C_{2-6}$ alkenyl, or substituted or unsubstituted $C_{2-6}$ alkynyl, halogeno, hydroxy, substituted or unsubstituted $C_{1-6}$ alkoxy, amino, mono-$C_{1-6}$ alkylamino, di-$C_{1-6}$ alkylamino, sulfo, carboxyl, phosphono or mono-$C_{1-6}$ alkylphosphono, where they may be different when more than one $R^8$ exist; and Q is substituted or unsubstituted $C_{1-6}$ alkyl, substituted or unsubstituted $C_{2-6}$ alkenyl, substituted or unsubstituted $C_{2-6}$ alkynyl, carboxyl, $CONR^eR^f$, $CONHNHR^g$, substituted or unsubstituted aryl or substituted or unsubstituted heteroaryl.

Furthermore, among the compounds according to [1] above, the compound (I) of the present invention is more preferably a compound represented as follows, or a salt thereof:

$R^1$, $R^2$, $R^3$, $R^4$, $R^5$ and $R^6$ are hydrogen atoms;
X is NH or a sulfur atom;
Y is C=O or C=S;
Q is carboxyl or $C_{1-6}$ alkoxycarbonyl;
G represents $R^7$-substituted aryl or $R^7$-substituted heteroaryl, where the $R^7$-substituted aryl or the $R^7$-substituted heteroaryl may further be substituted with one to five $R^8$;
$R^7$ is sulfo;
$R^8$ represents substituted or unsubstituted $C_{1-6}$ alkyl, substituted or unsubstituted $C_{2-6}$ alkenyl, or substituted or unsubstituted $C_{2-6}$ alkynyl, halogeno, hydroxy, substituted or unsubstituted $C_{1-6}$ alkoxy, amino, mono-$C_{1-6}$ alkylamino, di-$C_{1-6}$ alkylamino, sulfo, carboxyl, phosphono or mono-$C_{1-6}$ alkylphosphono, where they may be different when more than one $R^8$ exist.

Meanwhile, a compound represented by General Formula (I) wherein when $R^1$, $R^2$, $R^3$, $R^4$, $R^5$ and $R^6$ are hydrogen atoms, X is methylene, Y is C=O and G is carboxyl-substituted pyridyl, Q is not methoxycarbonyl is preferable as a compound of the present invention.

A particularly preferably compound is a compound selected from below or a salt thereof:
(2R)-2-amino-3-{[(3-sulfophenyl)carbamoyl]sulfanyl}propanoic acid;
(2S)-2-amino-3-{[(5-chloro-2-hydroxy-3-sulfophenyl)carbamoyl]amino}propanoic acid;
(2S)-2-amino-3-{[(3-chloro-4-methyl-5-sulfophenyl)carbamoyl]amino}propanoic acid;
(2S)-2-amino-3-{[(3-chloro-2-methyl-5-sulfophenyl)carbamoyl]amino}propanoic acid;
(2S)-2-amino-3-{[(3-sulfophenyl)carbamothioyl]amino}propanoic acid;
(2S)-2-amino-3-{[(3-chloro-2-methyl-5-sulfophenyl)carbamothioyl]amino}propanoic acid;
(2S)-2-amino-3-{[(3-chloro-4-methyl-5-sulfophenyl)carbamothioyl]amino}propanoic acid;
3-[(4S)-4-amino-4-(hydroxycarbamoyl)butanamide]-5-chloro-2-hydroxybenzene-1-sulfonic acid;
3-[(4S)-4-amino-4-(hydroxycarbamoyl)butanamide]-5-chloro-4-methylbenzene-1-sulfonic acid; and
(2S)-2-amino-3-{[(3-sulfophenyl)carbamoyl]amino}propanoic acid.

Hereinafter, a method for producing compound (I) will be described.

A compound represented by General Formula (I) of the present invention can be produced, for example, by the following method.

In the following reaction formula, $R^1$-$R^6$, $R^a$, $R^b$, $R^c$, X, Y, G and Q are the same groups as those in the definition for the above-described Formula (I). In addition, in Formula (2), M represents a functional group that binds to XH or a compound represented by Formula (3) to form X—Y.

(Reaction Formula A)

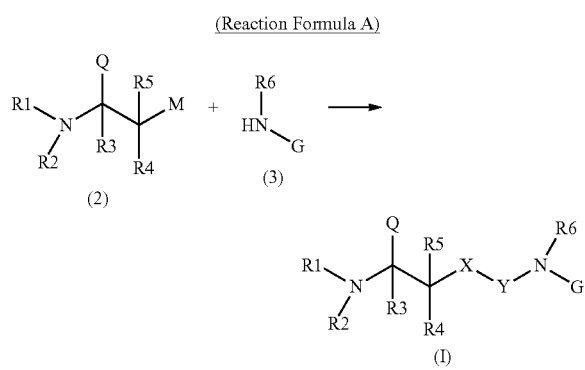

For example, when X—Y of Formula (I) represents —$CR^aR^b$—CO— group in Reaction Formula (A), the compound can be produced as follows.

A carboxylic acid derivative (2a) and an amine derivative (3) are dissolved or suspended in an appropriate solvent, and mixed with a condensing agent such as dicyclohexylcarbodiimide (DCC), 1-ethyl-(3-dimethylaminopropyl)carbodiimide hydrochloride (EDCI) or N,N-carbonyl diimidazole (CDI) in the presence or absence of a base such as triethylamine or pyridine, while the reaction system may be cooled, heated or the like as appropriate to produce (I-a). Upon condensation, an adjuvant, a catalyst or the like that adjusts the reaction, such as 1-hydroxybenzotriazole (HOBt), 1-hydroxy-7-azabenzotriazole (HOAt) may be added. The protective group may be removed as appropriate to produce an amide derivative represented by General Formula (I-a).

(Reaction Formula B)

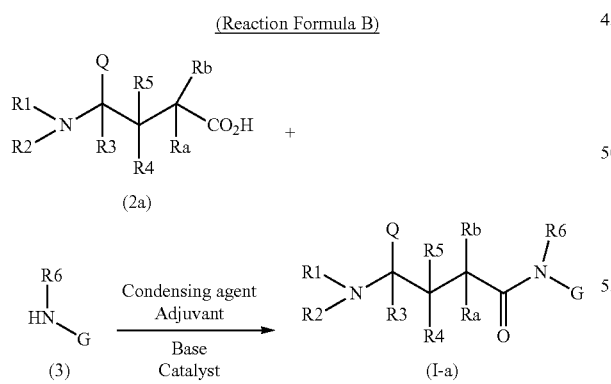

Alternatively, a carboxylic acid halide (2a') and an amine derivative (3) are mixed in an appropriate solvent and a catalyst such as 4-dimethylaminopyridine is used in the presence of a base such as triethylamine or pyridine, while cooling, heating or the like may be performed as appropriate to produce an amide derivative (I-a). Here, Hal in Reaction Formula B2 represents a halogen atom.

(Reaction Formula B2)

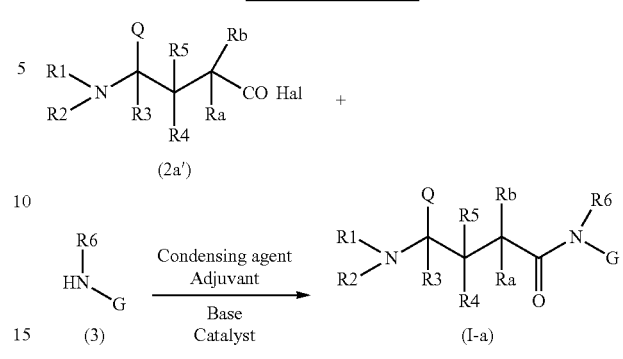

In addition, when X—Y of Formula (I) represents —O—CO— group in Reaction Formula A, the compound may be produced as follows. An alcohol derivative (2b) and an amine derivative (3) are dissolved or suspended in an appropriate solvent, and mixed with a condensing agent such as CDI, phosgene, triphosgene or the like in the presence or absence of a base such as triethylamine or pyridine, while the reaction system may be cooled, heated or the like as appropriate to produce a carbamate derivative (I-b).

(Reaction Formula C)

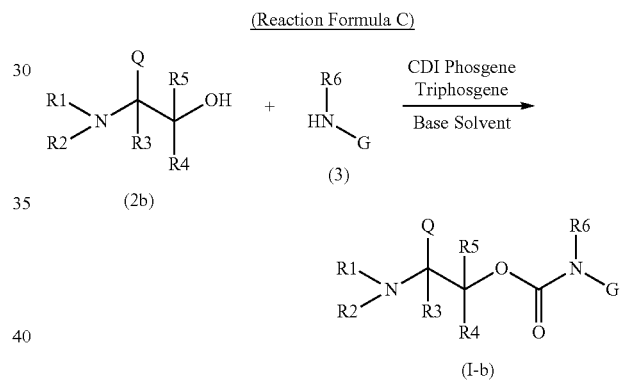

In addition, a thiocarbonylating agent such as 2,4-bis(4-methoxyphenyl)-1,3,2,4-dithiaziphosphetane-2,4-disulfide (Lawesson's reagent) may be reacted with (1-b) in an appropriate solvent with or without heating to produce an O-substituted thiocarbamate derivative (I-b').

(Reaction Formula C2)

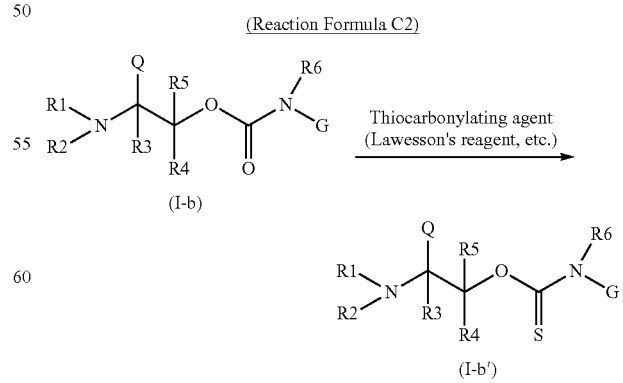

Moreover, in the case where X—Y of Formula (I) in Reaction Formula A represents —$NR^c$—CO— group, the compound may be produced, for example, as follows. The amine of an alkylamine derivative represented by (2c) or a salt thereof and the amine derivative of (3) are dissolved or suspended in an appropriate solvent, and mixed with a condensing agent such as CDI, phosgene or triphosgene or a carbonyl source such as dimethyl carbonate in the presence or absence of a base such as triethylamine or pyridine, while the reaction system may be cooled or heated as appropriate to produce an urea derivative (I-c).

(Reaction Formula D)

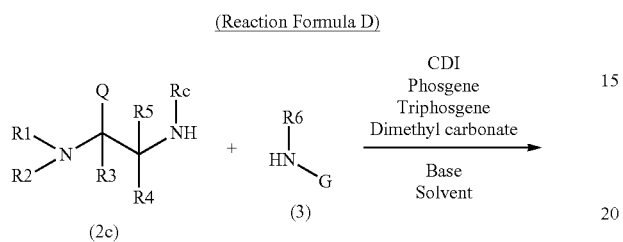

Alternatively, as shown in Reaction Formula D2, a method using Lossen rearrangement may be employed as described in Org. Lett., Vol. 11, No. 24, 2009, 5622-5625 while using a hydroxamic acid derivative (4) and an amine derivative (3) to produce an urea derivative (I-c').

(Reaction Formula D2)

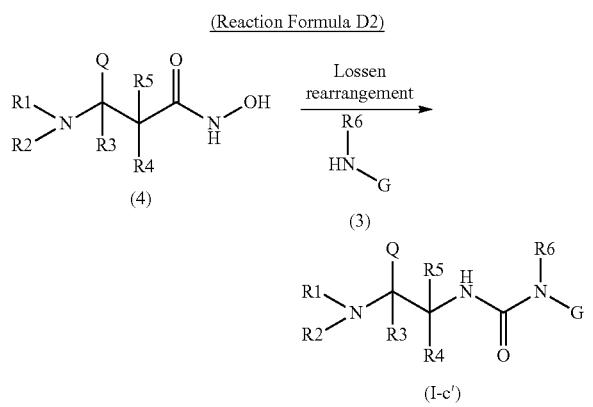

Alternatively, the compound may also be produced by a method in which a carbamate derivative (3a) is produced and then substituted with an amine derivative (2c).

(Reaction Formula D3)

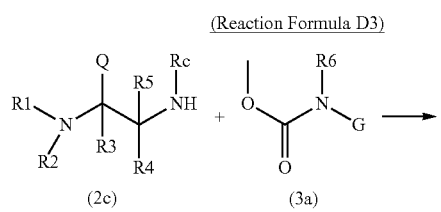

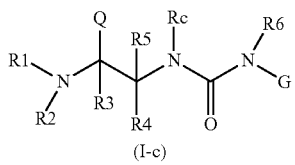

Alternatively, in the case where X—Y of Formula (I) represents —S—CO— group in Reaction Formula A, the compound may be produced as follows. A thiol derivative (2d) and an amine derivative of (3) are dissolved or suspended in an appropriate solvent, and mixed with a condensing agent such as CDI, phosgene or triphosgene or a carbonyl source such as dimethyl carbonate in the presence or absence of a base such as triethylamine or pyridine, while the reaction system may be cooled or heated as appropriate to produce a S-substituted thiocarbamate derivative (I-d).

(Reaction Formula E)

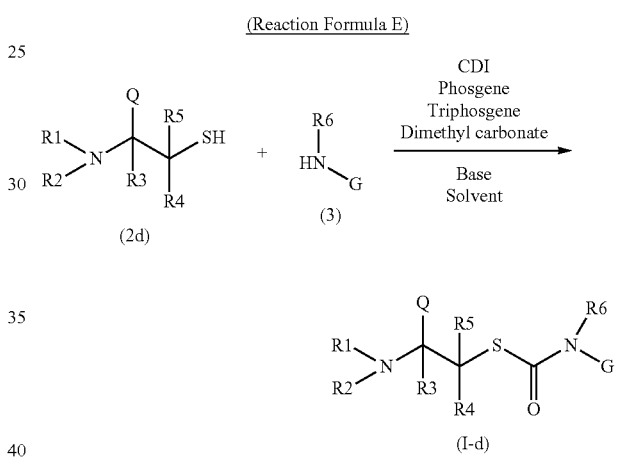

In the case where X—Y of Formula (I) represents N—C (=S)— group in Reaction Formula A, the compound may be produced, for example, as follows. Specifically, an amine derivative represented by (3b) is dissolved or suspended in an appropriate solvent and mixed, for example, with thiophosgene, carbon disulfide or the like in the presence of a base such as sodium carbonate, triethylamine or sodium ethoxide to generate isothiocyanate (5) as an intermediate. The isothiocyanate (5) may also be a commercially available product. The isothiocyanate, either isolated or not isolated, is dissolved in an appropriate solvent, and mixed with amine (2c) of the alkylamine derivative in the presence or absence of a base such as triethylamine, pyridine or sodium carbonate while cooling or heating as appropriate to produce a thiourea derivative (I-e).

(Reaction Formula F)

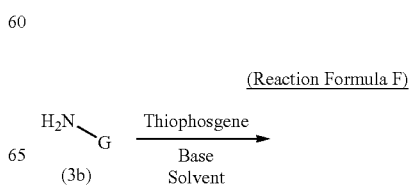

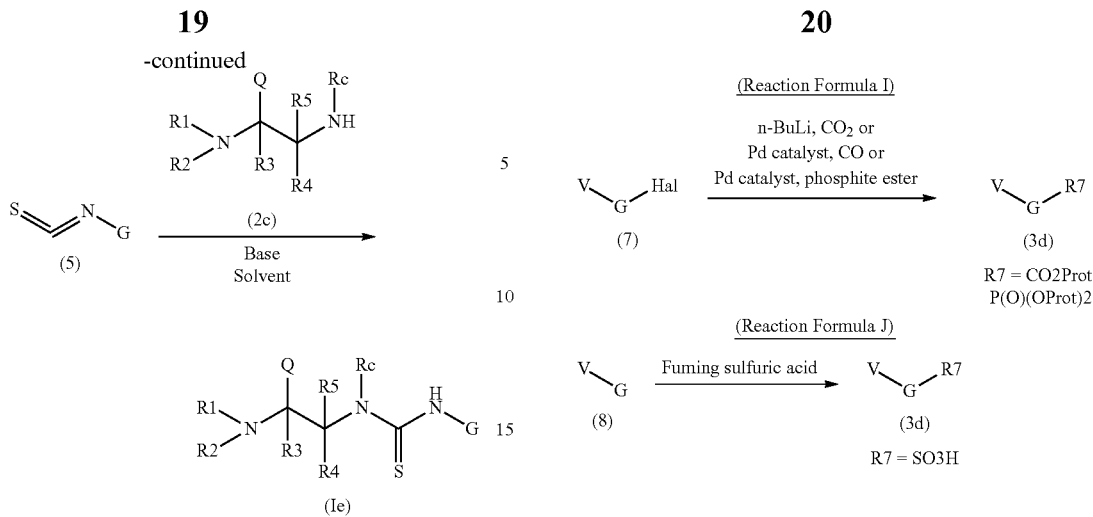

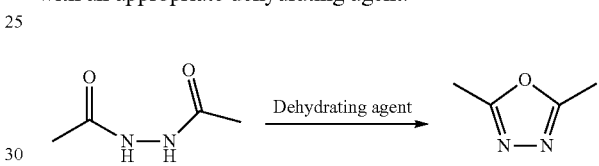

The amine derivative (3) may be a commercially available compound or may be produced as follows.

For example, the following nitro derivative (4) can be used, for example, with hydrogen gas as a reductant to perform hydrogenation reaction in the presence of a catalyst, or used to perform general reduction reaction, for example, through reaction with tin chloride to produce (3b).

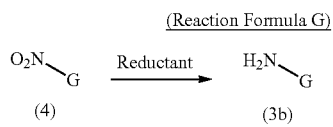

In addition, (3c) can be produced by selecting an appropriate reductant upon reduction as described in Journal of the Chemical Society, Perkin Transactions 1: Organic and Bio-Organic Chemistry (1972-1999), 1998, #3, p. 509-520.

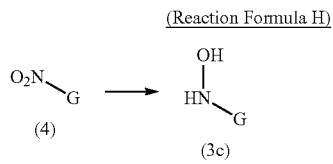

Examples of the substituent $R^7$ on G include a reaction in which aromatic halide (7) is reacted with a strong base such as n-butyllithium to perform lithium-halogen exchange for reaction with dry ice to introduce a carboxyl group, and a reaction in which aromatic halide (7) is reacted with a transition metal such as palladium for reaction with carbon monoxide gas. Similarly, a phosphate ester substitute can be produced, for example, by a method described in Synthesis, 1981, #1 p. 56-57 in which aromatic halide is reacted with a transition metal catalyst such as palladium for reaction with phosphite ester, or a sulfonic acid derivative is produced by reacting fuming sulfuric acid with aromatic compound (8) as shown in Reaction Formula J. Here, in reaction formula I, Hal, V and Prot represent a halogen atom or a pseudohalogen atom, a protected nitrogen atom or a group that can change into a nitrogen atom and a protective group or a hydrogen atom, respectively.

Heteroaryls may be synthesized, for example, according to the method described in Chemical reactivity of aromatic hetero ring compound and ring synthesis (Sakamoto et al., Kodansha Scientific). For example, the following heteroaryl can be synthesized by treating a diacylhydrazine derivative with an appropriate dehydrating agent.

A solvent used for the reaction of each of the above-described steps is not particularly limited as long as it does not interfere with the reaction and dissolves at least a part of the starting material, examples being:

Aliphatic hydrocarbons: hexane, cyclohexane, petroleum ether;

Aromatic hydrocarbons: benzene, toluene, xylene;

Amides: dimethylformamide, N-methyl-2-pyrolidone, dimethylacetamide;

Amines: triethylamine, diisopropylethylamine, pyridine, 2,6-lutidine;

Alcohols: methanol, ethanol, 1-propanol, 2-propanol, 1-butanol, 2-butanol;

Ethers: diethylether, dioxane, tetrahydrofuran, dimethoxyethane;

Ketones: acetone, methyl ethyl ketone, methyl isobutyl ketone, cyclohexanone;

Esters: ethyl acetate, isopropyl acetate, butyl acetate;

Acids: formic acid, acetic acid, propionic acid, trifluoroacetic acid, sulfuric acid;

Sulfoxides: dimethylsulfoxide, sulfolane;

Nitriles: acetonitrile, propionitrile;

Halogenated hydrocarbons: dichloromethane, chloroform, carbon tetrachloride, dichloroethane, chlorobenzene;

Others: water; and mixtures thereof.

In each of the above-described steps, it may be preferable to introduce a protective group into the functional group of the formulae in advance. As the protective group, for example, functional groups described in Protective Groups in Organic Synthesis, 4th Ed. (WILEY-INTERNATIONAL, WUTS, GREEN) and the like may be used, although the present invention is not limited thereto. A compound of interest can be obtained by appropriately performing protection and deprotection according to the method described in the above-mentioned document or the like.

The compound represented by General Formula (I) or a salt thereof produced as described above can be isolated/purified by known separation/purification means such as extraction, condensation, vacuum condensation, solvent extraction, crystallization, recrystallization, re-extraction, various chromatographies or the like.

The alkylamine derivatives used with the present invention also comprise a form of salt. When the alkylamine derivative of the present invention takes a form of salt, the salt should be a pharmaceutically acceptable salt or an edible salt. For acid groups such as a carboxyl group in the formula, examples of salts include ammonium salt, salts with alkali metals such as sodium and potassium, salts with alkali earth metals such as calcium and magnesium, aluminum salt, zinc salt, salts with organic amines such as triethylamine, ethanolamine, morpholine, pyrrolidine, piperidine, piperazine and dicyclohexylamine, and salts with basic amino acids such as arginine and lysine. For basic groups in the formula, if any, examples of salts include salts with inorganic acids such as hydrochloric acid, sulfuric acid, phosphoric acid, nitric acid and hydrobromic acid, salts with organic carboxylic acids such as acetic acid, trifluoroacetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid and malic acid, and salts with organic sulfonic acids such as methanesulfonic acid, benzenesulfonic acid and p-toluenesulfonic acid. These salts are produced by bringing the compound into contact with an acid or a base that can be used for producing a pharmaceutical product.

According to the present invention, a compound represented by Formula (I) or a salt thereof may be an anhydride or may form a solvate such as a hydrate or an alcohol adduct. The term "solvation" as used herein refers to a phenomenon where a solute molecule or ion strongly attracts a solvent molecule adjacent thereto in a solution and form a molecular population. For example, if the solvent is water, it is referred to as hydration. The solvate may be either a hydrate or a non-hydrate. As a non-hydrate, an alcohol (for example, methanol, ethanol, n-propanol), dimethylformamide or the like can be used.

In addition, a compound of the present invention or a salt thereof may be present in several tautometric forms, for example, enol and imine forms, keto and enamine forms, or a mixture thereof. Tautomers are present as a mixture of a tautometric set in a solution. In a solid form, one tautomer is generally dominant over the other. Although only one tautomer may be described, the present invention comprises any tautomer of the compound of the present invention.

The present invention comprises all of the stereoisomers (for example, enantiomers, diastereomers (including cis and trans geometric isomers)) of the compound represented by Formula (I), racemic forms of these isomers, and other mixtures. For example, a compound represented by Formula (I) of the present invention may have one or more asymmetric centers, and the present invention comprises a racemic mixture, a diastereomer mixture and an enantiomer of such a compound.

When a compound according to the present invention is obtained in a form of a free form, it may be converted into a state of a salt formable by the compound, a hydrate thereof or a solvate thereof according to a routine method.

On the other hand, when a compound according to the present invention is obtained as a salt, a hydrate or a solvate of the compound, it may be converted into a free form of the compound according to a routine method.

The present invention comprises any isotope of the compound represented by Formula (I). An isotope of a compound of the present invention has at least one atom substituted with an atom that has the same atomic number (proton number) but has a different mass number (sum of the numbers of protons and neutrons). Examples of isotopes included in the compound of the present invention include a hydrogen atom, a carbon atom, a nitrogen atom, an oxygen atom, a phosphorus atom, a sulfur atom, a fluorine atom and a chlorine atom, including $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$. In particular, unstable radioactive isotopes such as $^{3}H$ and $^{14}C$, that release radiation and emit neutron are useful for a body tissue distribution test of a pharmaceutical product or a compound. Since a stable isotope does not undergo decay, has almost no change in the abundance and has no radioactivity, it can be used safely. An isotope of a compound of the present invention may be converted according to a routine method by replacing the reagent used for synthesis with a reagent containing a corresponding isotope.

A compound of the present invention can be used as a pharmaceutical agent, particularly as a CaSR agonistic agent, and can be used as a prophylactic or therapeutic agent for a disease that is ameliorated through CaSR activation.

CaSR is expressed in various tissues and involved in various physiological actions. CaSR senses an increase in the blood calcium level in parathyroid, and suppresses secretion of parathyroid hormone (PTH) to correct the blood calcium level. Accordingly, in addition to the above-mentioned hyperparathyroidism, a compound that activates CaSR is also expected to serve as a therapeutic drug for various diseases such as bone diseases and upper and lower digestive disorders (The Journal of Clinical Investigation, 1997, Vol. 99, p. 2328-2333 and The American Journal of Physiology-Gastrointestinal and Liver Physiology, 2002, Vol. 283, p. G240-G250), diabetes (The Journal of Biological Chemistry, 1999, Vol. 274, p. 20561-20568 and The Journal of Biological Chemistry, 2000, Vol. 275, p. 18777-18784), and anterior pituitary hypofunction/hyperfunction (Molecular Endocrinology, 1996, Vol. 10, p. 555-565).

In addition to calcium modulation, CaSR is reported to be expressed in both mature and undifferentiated adipocytes and involved in differential inhibition in the adipocytes (Endocrinology. 2005 May; 146(5): 2176-9, Exp Cell Res. 2004 Dec. 10; 301(2):280-92.), expressed in erythroblasts, megakaryocytes and platelets and involved in hematopoiesis regulation in the myeloid cells (J Bone Miner Res. 1997 December; 12(12):1959-70.), and expressed in gastric parietal cells and involved in gastric acid secretion (J Clin Endocrinol Metab. 2005 March; 90(3):1489-94). Additionally, CaSR is also reported to be expressed in the following tissues and involved in the functional regulations thereof: duodenum, jejunum and ileum (Am J Physiol Gastrointest Liver Physiol. 2002 July; 283(1): G240-50.), large intestine (Am J Physiol Gastrointest Liver Physiol. 2002 July; 283(1): G240-50.), epidermal keratinocytes (Cell Calcium. 2004 March; 35(3): 265-73.), hepatocytes (J Biol. Chem. 2001 Feb. 9; 276(6): 4070-9.), epithelium lentis (Biochem Biophys Res Commun. 1997 Apr. 28; 233(3): 801-5.), pancreatic Langerhans' islet β cells (Endocrine. 1999 December; 11(3): 293-300.), lung (J Clin Endocrinol Metab. 1998 February; 83(2): 703-7.), monocytic cells (J Clin Invest. 2000 May; 105(9): 1299-305.), osteoblasts (Endocrinology. 2004 July; 145(7): 3451-62, Am J Physiol Endocrinol Metab. 2005 March; 288(3): E608-16. Epub 2004 Nov. 16.) and the like.

Moreover, since glutathione, which is known as an agent for imparting kokumi, has been confirmed to show a calcium receptor activating effect, and that a peptide derivative having a CaSR agonistic activity presents kokumi (WO2007/055393), a compound having a CaSR agonistic activity is suggested to be useful as an agent for imparting kokumi.

In particular, calcium receptors are expressed in the G cells and the parietal cells of the stomach, and are found to have an effect of stimulating gastrin and gastric acid secretion (Journal of Clinical Investigation (1997), 99: 2328-2333, Gastroenterology 1999; 116: 118-126). In addition, calcium receptors are expressed in the large intestine and regulates secretion of water (The American Journal of Physiology-Gastroinstinal and Liver Physiology (2002), 283: G240-G250). Since calcium receptor agonists such as cinacalcet and gamma-glutamyl peptide derivatives have been shown to have an effect of suppressing diarrhea in animal models (WO2008/139947), an effect of stimulating bicarbonic acid or somatostatin secretion, and an effect of reducing an injury area in non-steroidal anti-inflammatory drug (NSAID)-induced small intestine inflammation animal models (WO2009/119554), a compound having a CaSR agonistic effect is found beneficial as a prophylactic or therapeutic agent for diarrhea or acid secretion-associated diseases such as, gastric ulcer, duodenal ulcer and reflux esophagitis as well as an appetite-modulating agent.

Furthermore, since a peptide or a low-molecular compound with calcium receptor activation has been shown to stimulate secretion of GLP-1 and CCK in intestinal tract-derived STC-1 and GLUTag cells (WO2009/11221), a compound having a CaSR agonistic effect is found beneficial as a prophylactic or therapeutic agent for diabetes and obesity.

Moreover, since cinacalcet and gamma-glutamylvaline have been confirmed to have an IgA production-promoting ability through LPS stimulation and an IgG production-promoting effect through ConA stimulation (WO2009/128523), a compound having a CaSR agonistic effect is found beneficial as an immunostimulator or as a therapeutic or prophylactic agent for a disease that is effectively prevented or treated by immunostimulation, for example, various infectious diseases, diarrhea, polyp, tumor, enteritis or allergy.

Accordingly, a compound of the present invention can be used as an active ingredient of a pharmaceutical composition for preventing or treating a disease that is ameliorated through CaSR activation.

Here, "a disease that is ameliorated through CaSR activation" is an illness or deficiency characterized by abnormal calcium homeostasis, or an illness or a condition that is induced by reduction in CaSR function, specific examples being diarrhea, diseases associated with secretion of digestive tract acid, eating disorders such as excessive appetite, hyperparathyroidisms (primary and secondary parathyroid hyperfunctions, and secondary hyperparathyroidism under maintenance dialysis), diabetes, obesity, compromised immune function, Paget's disease, malignant hypercalcemia, osteoporosis and hypertension.

The diseases associated with secretion of digestive tract acid include ulcer and inflammatory diseases in digestive tracts such as the stomach or the small intestine (duodenum, jejunum, ileum), which include those induced by endogenous causes such as stress or the like, and those induced by exogenous causes such as drugs (non-steroidal anti-inflammatory drugs, alcohol or the like).

Examples of "peptic ulcer" include gastric ulcer, duodenal ulcer, gastritis, NSAID-induced small intestine inflammation, reflux esophagitis, non-erosive gastroesophageal reflux disease and non-steroidal anti-inflammatory drug-induced ulcer.

The compound of the present invention is administered directly or as a pharmaceutical composition that contains the compound of the present invention as an active ingredient. A method for applying such a pharmaceutical composition is not particularly limited, and oral administration, invasive administration using injection or the like, suppository administration or transdermal administration may be employed. The active ingredient can be mixed with a non-toxic solid or liquid carrier for a pharmaceutical agent appropriate for the given method such as oral administration, injection or the like, and administered in a form of a common pharmaceutical formulation. Examples of such formulations include formulations in a solid form such as a tablet, granules, a pill, powder, a capsule, a suppository, a sugarcoated tablet or a depot formulation, liquid formulation such as a solution formulation, suspension and emulsion, and a lyophilized formulation. These formulations can be prepared by pharmaceutically common means.

Examples of the above-described non-toxic carrier for a pharmaceutical agent include glucose, lactose, sucrose, starch, calcium carbonate, calcium phosphate, mannitol, dextrin, fatty acid glyceride, polyethylene glycol, hydroxyethyl starch, ethylene glycol, polyoxyethylene sorbitan fatty acid ester, gelatin, albumin, amino acid, water and physiological saline. If necessary, a common additive such as a stabilizer, a moisturizer, an emulsifier, a binder or a tonicity agent may appropriately be added.

A compound of the present invention can also be used as eatables that have an effect of treating or preventing a CaSR-involved disease. For example, it may be made into eatables with a container or a package thereof indicating that it has an effect of treating or preventing the above-mentioned CaSR-involved disease.

A dosage form and an administration form of a compound of the present invention are not particularly limited, and it may be given by oral administration or by parenteral administration (intake) such as administration by intravenous drip, or administration by injection (transvenous administration). For the sake of easier administration, oral administration is favorable but the administration is not limited thereto.

For an orally administered agent, granules, fine granules, a powdered agent, a coated tablet, a tablet, a suppository, powder, a (micro) capsule, a chewable agent, syrup, juice, a liquid agent, suspension and emulsion can be employed. For an injectable agent, those for direct intravenous infusion, those for administration by intravenous drip, and formulation that prolongs the release of the active substance can be employed. Thus, a dosage form of a general pharmaceutical formulations can be employed.

In the case of oral administration, the dosage differs depending on the condition and age of the patient as well as the given method, but it should be an amount effective for treatment or prevention, which may appropriately be adjusted according to the age, sex, weight, condition and the like of the patient. For example, in the case of an oral administration, an amount of a CaSR agonist per day, in general, is preferably 0.001 mg-10 mg and more preferably 0.1 mg-1 mg per kilogram weight of an adult.

Moreover, a dosage, in the case of parenteral administration such as administration by intravenous drip or administration by injection (transvenous administration), is preferably about one-tenth to one-twentieth of the above-described range of preferable dosage (amount of intake) for oral administration.

The above-described dosage for oral administration may similarly be applied to the later-described food, which does not preclude that the CaSR agonist is contained in the food such that the amount of intake is lower than that for administration.

A compound of the present invention can be formulated according to a routine method. According to the requirement for the formulation, various pharmacologically acceptable formulation substances (such as adjuvant) can be blended. A formulation substance can appropriately be selected according to the dosage form of the formulation, examples being an excipient, a diluent, an additive, a disintegrant, a binder, a coating agent, a lubricant, a sliding agent, a lubricator, a flavoring agent, a sweetening agent and a solubilizer. Furthermore, specific examples of the formulation substance include magnesium carbonate, titanium dioxide, lactose, mannitol and other sugars, talc, milk protein, gelatin, starch, cellulose and derivatives thereof, animal and plant oils, polyethylene glycol, solvents such as sterile water and mono- or polyalcohol such as glycerol.

Other than a routine method, a compound of the present invention can also be formulated according to various pharmaceutical formulation forms that will be developed in the future. For such formulations, methods developed in the future can appropriately be employed.

A package containing a compound of the present invention may include directions providing explanations about use thereof. The directions may be, for example, a so-called package insert that provides explanatory matter related to use, efficacy, an administration method and the like.

A compound of the present invention may be contained in food. The form of food is not particularly limited, and can be produced by the same production method and with the same materials as general food except that a CaSR agonist is blended therein. Examples of food include seasonings; beverage such as juice and milk; sweets; jelly; health food; processed agricultural products; processed seafood products; processed livestock products such as milk; and supplementary food. In addition, such food can be provided as food with health claims, including food labeled with a claim that it is used for preventing, treating or ameliorating acid secretion-associated diseases, in particular, food for specified health use.

When a compound of the present invention is used as supplementary food, it may be prepared into a form such as a tablet, a capsule, powder, granule, suspension, a chewable agent or syrup. Other than those taken in as food, supplementary food according to the present invention also refers to those taken in for the purpose of supplying nutrition, including nutritious supplements, supplements and the like. In addition, the supplementary food of the present invention also includes some of the food with health claims.

A method for using an agent for imparting kokumi that contains one or more types of compounds selected from the compounds of the present invention as active ingredients is not particularly limited, and it may be used by adding to eatables such as seasonings, food, beverage or the like.

A substance for imparting kokumi of the present invention may be used alone or in combination with other various additives or the like to be used by being added to eatables such as seasonings, food and beverage.

Moreover, an agent for imparting kokumi of the present invention may consist, for example, only of one or more types of compounds selected from the above-described compounds of the present invention, or it may further be added with an existing compound having kokumi imparting activity (glutathione, alliin, etc.), various additives and the like. In this respect, one or more types of existing compounds with CaSR stimulating activity may be added, and the present invention also comprises such compounds.

Herein, "imparting kokumi" refers to enhancement of any one of the five basic tastes, i.e., sweetness, saltiness, sourness, bitterness and umami (savory taste), and impartment of tastes associated with the basic tastes such as richness, thickness, growth (or mouthfulness), continuity and harmony that come along with the basic tastes. Moreover, an agent for imparting kokumi can also be expressed as a flavor enhancer. Hence, an agent for imparting kokumi of the present invention can also be used as a sweetness enhancer, a saltiness enhancer, a sourness enhancer, a bitterness enhancer or a umami enhancer.

Examples of existing compounds with CaSR activity include cations such as calcium and gadolinium, basic peptides such as polyarginine and polylysine, polyamines such as putrescine, spermine and spermidine, proteins such as protamine, peptides such as phenylalanine and glutathione, and cinacalcet. These compounds may also take a form of acceptable salt.

The above-mentioned additives can be used without particular limitation as long as they are known to be able to be added to and blended into eatables such as seasonings, food and beverage. Examples of such additives include flavors, sugars, sweeteners, food fiber, vitamins, amino acids such as monosodium glutamate (MSG), nucleic acids such as inosine monophosphate (IMP), inorganic salts such as sodium chloride, and water.

An amount of a substance for imparting kokumi of the present invention or an agent for imparting kokumi of the present invention used for eatables should be an effective amount for imparting kokumi, and can appropriately be adjusted according to use. For example, in the case of seasonings, food or beverage, a total amount of an agent for imparting kokumi or a substance for imparting kokumi of the present invention in the seasonings, food or beverage is 1 wt·ppb-99.9 wt %, preferably 10 wt·ppb-99.9 wt %, and more preferably about 10 wt·ppm-10 wt %.

Thus, one or more types of the substances for imparting kokumi of the compound of the present invention or the agents for imparting kokumi of the present invention can be added to eatables to give a content of 1 wt·ppb-99.9 wt %, preferably 10 wt·ppb-99.9 wt %, and more preferably about 10 wt·ppm-10 wt % so as to produce eatables with an imparted kokumi.

Furthermore, the above-described seasonings that has been imparted with kokumi by containing 1 wt·ppb-99.9 wt % of one or more types of the substances for imparting kokumi of the present invention or the agents for imparting kokumi of the present invention can be added to eatables to give a content of 0.01-10 wt % and preferably 0.1-10 wt % so as to produce eatables with an imparted kokumi.

A form of the substance for imparting kokumi of a compound of the present invention or the agent for imparting kokumi of the present invention, which is added to eatables is not limited in terms of its physicality, i.e., whether dry powder, paste, solution or the like.

EXAMPLES

The present invention will be described in detail by means of examples below. They are preferable embodiments of the present invention and the present invention should not be limited to these examples. The structures and MS value or NMR measurements of the compounds synthesized according to the following methods are shown in Tables 1-15.

In these examples, purification step A refers to a step of lyophilizing a fraction of interest by performing elution with a mixed solution of water and acetonitrile containing 0.1% trifluoroacetic acid (v/v) upon a reversed-phase high-performance liquid chromatography that uses a silica gel chemically bounded with an octadodecyl group as a filler. A routine method generally refers to a synthetic chemical method, for example, solvent extraction, back extraction, washing, neutralization and drying.

Example 1

Synthesis of
(2S)-2-amino-4-[(pyridine-2-yl)carbamoyl]butanoic
acid trifluoroacetic acid salt 70 mg (0.188 mmol, 1 equivalent) of Cbz-Glu-OBzl and 85 mg (0.226 mmol) of O-(7-azabenzotriazole-1-yl)-N,N,N',N'-tetramethyluronium hexafluorophosphate (HATU) were dissolved in 1 ml of DMF, added with 39 µl (0.282 mmol) of triethylamine and stirred for 5 minutes. 18 mg of 2-aminopyridine was added, and stirred at room temperature overnight. Aftertreatment was performed according to a routine method and the resulting crude product was dissolved in 3 ml of acetic acid, to which a catalyst amount of palladium carbon (Pd/C) was added and stirred in a hydrogen atmosphere overnight. After filtrating the catalyst, the solvent was distilled away, and the resulting residue was subjected to purification step A to obtain the title compound.
Yield: 23.1 mg Example 2

Synthesis of (2S)-2-amino-4-[(5-bromo-6-methylpyridine-2-yl)carbamoyl]butanoic acid trifluoroacetic
acid salt 100 mg (0.33 mmol) of Boc-Glu-OtBu, 53.8 mg (0.40 mmol) of 1-hydroxy-7-azabenzotriazole and 150.4 mg (0.40 mmol) of O-(7-azabenzotriazole-1-yl)-N,N,N',N'-tetramethyluronium hexafluorophosphate were dissolved in 1 ml of DMF, added with 68.5 µl (0.49 mmol) of triethylamine and stirred at room temperature for 5 minutes. 61.7 mg (0.33 mmol) of 6-amino-3-bromo-2-methylpyridine was added and stirred at room temperature overnight. After diluting the reaction solution with water and acetonitrile, the purification step A was used to obtain 109.3 mg of the crude purified substance of the title compound in protected form. To the obtained crude purified substance, 2 ml of trifluoroacetic acid was added and the resultant was stirred at room temperature overnight. After distilling the solvent away, the resultant was purified using purification step A to obtain the title compound.
Yield: 43.36 mg Example 3

Synthesis of
(2S)-2-amino-4-[(3-sulfophenyl)sulfamoyl]butanoic
acid

According to the method described in J. Med. Chem. 1999, 42, 5197-5211, 0.24 g (0.425 mmol) of 2-{[(benzyloxy)carbonyl]amino}-4-[(3-{[(benzyloxy)carbonyl]amino}-4-methoxy-4-oxobutyl)disulfanyl]methyl butanoate was obtained as an intermediate. To 0.24 g of the resulting intermediate, 2 ml of acetic acid and 0.5 ml of water were added and 87 µl (1.7 mmol) of bromine was added while cooling with ice. After agitation for 20 minutes, the solvent was distilled away, and aftertreatment was performed with ethyl acetate and 1M hydrochloric acid according to a routine method to distill away the solvent. To the resulting residue, 191 mg (1.1 mmol) of 3-aminobenzenesulfonic acid was added and the resultant was suspended in 5 ml of methylene chloride. To this, 0.52 ml (3 mmol) of N,N-diisopropylethylamine was added and stirred overnight. After distilling the solvent away, purification step A was used to obtain 33.2 mg of the crude product.

The resulting crude product was dissolved in 1 ml of tetrahydrofuran, 0.5 ml of methanol and 0.5 ml of water, to which 9 mg of lithium hydroxide was added. Following an hour of agitation, the solvent was distilled away. To the resulting residue, 3 ml of 48% hydrogen bromide-acetic acid solution was added and stirred for an hour. After distilling the solvent away, purification step A was used to obtain the title compound.
Yield: 9.2 mg Example 4

Synthesis of (2R)-2-amino-3-{[(3-sulfophenyl)carbamoyl]sulfanyl}propanoic acid

To 171 mg (1 mmol) of L-cysteine methyl ester hydrochloride, 2 ml of tetrahydrofuran and 0.3 ml of triethylamine were added, 218 mg (1 mmol) of di-tert-butyl dicarbonate dissolved in 2 ml of tetrahydrofuran was added and the resultant was stirred at room temperature for 2 hours. Ethyl acetate and 10% aqueous citric acid solution were used for aftertreatment according to a routine method to obtain a crude product of Boc-Cys-OMe. To the obtained crude product, 191 mg of 3-aminobenzene sulfonic acid and 100 mg (0.33 mmol) of triphosgene were added and the resultant was suspended in 3 ml of methylene chloride. To this, 3 mmol of N,N-diisopropylethylamine was added and stirred for 2 hours. After distilling the solvent away, the resultant was diluted with water and acetonitrile, and purification step A was employed to obtain 72 mg of a crude purified substance of the title compound in protected form. 72 mg of the resulting crude purified substance was dissolved in 1 ml of tetrahydrofuran, 0.5 ml of methanol and 0.5 ml of water, to which 17 mg of lithium hydroxide was added and the resultant was stirred at room temperature for 2 hours. After distilling the solvent away, 2 ml of trifluoroacetic acid was added and stirred for 2 hours. The resultant residue was purified by purification step A to obtain the title compound.
Yield: 44.0 mg Example 5

Synthesis of (2R)-2-amino-3-{[(5-chloro-2-hydroxy-3-sulfophenyl)carbamoyl]sulfanyl}propanoic acid The title compound was obtained through a similar operation except that 3-aminobenzenesulfonic acid used in Example 4 was replaced with 3-amino-5-chloro-2-hydroxy-benzenesulfonic acid.
Yield: 15.0 mg Example 6

Synthesis of (2S)-2-amino-3-{[(5-chloro-2-hydroxy-3-sulfophenyl)carbamoyl]amino}propanoic acid 297 mg (1 mmol) of 3-amino-N-(tert-butoxycarbonyl)-L-alanine tert-butylester hydrochloride, 223 mg (1 mmol) of 3-amino-5-chloro-2-hydroxybenzenesulfonic acid and 100 mg (0.33 mmol) of triphosgene were suspended in methylene chloride (3 ml), added with 0.8 ml of pyridine, and stirred at room temperature overnight. The solvent was distilled away, and the resultant residue was purified by employing purification step A to obtain the title compound in protected form. To the resulting protected form, 3 ml of trifluoroacetic acid was added, and the resultant was stirred for 5 hours. Subsequently, the solvent was distilled away and the obtained residue was purified using purification step A to obtain the title compound.

Yield: 20.1 mg

Example 7

Synthesis of 3-({[(2S)-2-amino-propoxy]carbonyl}amino)-5-chloro-2-hydroxybenzene-1-sulfonic acid 75 mg (1 mmol) of (S)-2-(tert-butoxycarbonylamino)-1-propanol (Boc-Ala-ol), 223 mg (1 mmol) of 3-amino-5-chloro-2-hydroxybenzenesulfonic acid and 100 mg (0.33 mmol) of triphosgene were suspended in 3 ml of methylene chloride, and added with 0.7 ml of pyridine. Following agitation at room temperature overnight, the solvent was distilled away, purified using purification step A to obtain a crude purified substance of the title compound in protected form. To the resultant crude purified substance, 2 ml of trifluoroacetic acid was added, and the resultant was stirred at room temperature for 2 hours. Subsequently, the solvent was distilled away, and the resulting residue was added with water and acetonitrile for deposition and the deposited solid was filtrated to obtain the title compound.

Yield: 140.1 mg

Example 8

3-({[(2S)-2-amino-3-methylbutoxy]carbonyl}amino)-5-chloro-2-hydroxybenzene-1-sulfonic acid The title compound was obtained through a similar operation except that Boc-Ala-ol used in Example 7 was replaced with (S)-(–)-2-(butoxycarbonylamino-3-methyl 1-butanol (Boc-Val-ol).

Yield: 108.5 mg

Example 9

Synthesis of 3-({[(2S)-2-amino-3-phenylpropoxy]carbonyl}amino)-5-chloro-2-hydroxybenzene-1-sulfonic acid 285 mg (1 mmol) of (S)-2-(benzyloxycarbonylamino)-3-phenyl-1-propanol, 223 mg (1 mmol) of 3-amino-5-chloro-2-hydroxybenzenesulfonic acid and 100 mg (0.33 mmol) of triphosgene were suspended in 3 ml of methylene chloride, to which 0.7 ml of pyridine was dropwisely added. Following agitation at room temperature overnight, the solvent was distilled away, and the resultant was purified using purification step A to obtain a crude purified substance of the title compound in protected form. To the obtained crude purified substance, 2 ml of 48% hydrogen bromide-acetic acid solution was added, and the resultant was stirred at room temperature for 2 hours. The solvent was distilled away and water and acetonitrile were added to the obtained residue for deposition. The deposited solid substance was filtrated to obtain the title compound.

Yield: 151.6 mg

Example 10

Synthesis of 3-({[(2S)-2-amino-2-phenylethoxy]carbonyl}amino)-5-chloro-2-hydroxybenzene-1-sulfonic acid The title compound was obtained through a similar operation except that Boc-Ala-ol used in Example 7 was replaced with (S)—N-(tert-butoxycarbonyl)-2-phenylglycinol.

Yield: 55.2 mg

Example 11

Synthesis of 3-({[(2S)-2-amino-4-carbamoylbutoxy]carbonyl}amino)-5-chloro-2-hydroxybenzene-1-sulfonic acid The title compound was obtained through a similar operation except that Boc-Ala-ol used in Example 7 was replaced with (S)-tert-butyl 5-amino-1-hydroxy-5-oxopentane-2-yl-carbamate (Boc-Gln-ol).

Yield: 25.2 mg

Example 12

Synthesis of 3-({[(2S)-2-amino-4-cyanobutoxy]carbonyl}amino)-5-chloro-2-hydroxybenzene-1-sulfonic acid The compound was obtained as a by-product during synthesis in Example 11.

Yield: 6.2 mg

Example 13

Synthesis of (2S)-2-amino-3-{[(3-chloro-4-methyl-5-sulfophenyl)carbamoyl]amino}propanoic acid 100 mg (0.336 mmol) of 3-amino-N-(tert-butoxycarbonyl)-L-alanine tert-butylester hydrochloride, 74 mg (0.336 mmol) of 5-amino-3-chloro-2-methylbenzenesulfonic acid and 55 mg (0.336 mmol) of N,N-carbonyl diimidazole were added with 1 ml of methylene chloride and 0.25 ml of pyridine, and the resultant was stirred at room temperature overnight. The solvent was distilled away, and the resulting residue was purified using purification step A to obtain the title compound in protected form. The obtained protected form was added with 3 ml of trifluoroacetic acid, stirred for 2 hours, and then the solvent was distilled away. The resulting residue was purified using purification step A to obtain the title compound.

Yield: 43.98 mg

Example 14

Synthesis of (2S)-2-amino-3-{[(3-chloro-2-methyl-5-sulfophenyl)carbamoyl]amino}propanoic acid The title compound was obtained through a similar operation except that 3-amino-5-chloro-4-methylbenzenesulfonic acid was used instead of 5-amino-3-chloro-2-methylbenzenesulfonic acid in Example 13.

Yield: 4.0 mg

Example 15

Synthesis of 3-[(4S)-4-amino-4-(5-methyl-1,3,4-oxadiazol-2-yl)butanamide]-5-chloro-2-hydroxybenzene-1-sulfonic acid Step 1

Synthesis of (4S)-4-{[(tert-butoxy)carbonyl]amino}-4-(5-methyl-1,3,4-oxadiazole-2-yl)butanoic acid benzyl ester 674 mg (2 mmol) of (S)-5-(benzyloxy)-2-(tert-butoxycarbonylamino)-5-oxopentanoic acid (Boc-Glu (OBzl)-OH) and 148 mg (2 mmol) of acetohydrazide were added with 5 ml of tetrahydrofuran, added with 356 mg of N,N-carbonyl diimidazole and stirred at room temperature overnight. The solvent was distilled away, and the resultant was purified using purified purification step A to obtain a crude purified substance of (4S)-4-(N'-acetylhydrazinecarbonyl)-4-{[(tert-butoxy)carbonyl]amino}butanoic acid benzyl ester. The obtained crude purified substance was dissolved in 2 ml of methylene chloride, which was added with 72 mg of Burgess reagent and stirred at room temperature overnight. Another 72 mg of Burgess reagent was added and stirred for two days. After distilling the solvent away, purification was carried out using purification step A to obtain the title compound.

Step 2

The compound obtained in Step 1 was dissolved in ethyl acetate, added with a catalyst amount of Pd/C, and stirred in a hydrogen atmosphere overnight. The catalyst was filtrated and the solvent was distilled away, thereby obtaining a crude product. To the resulting crude product, 6 mg of 3-amino-5-chloro-2-hydroxybenzenesulfonic acid, 4.3 mg of 1-hydroxy-7-azabenzotriazole, 12 mg of O-(7-azabenzotriazole-1-yl)-N,N,N',N'-tetramethyluronium hexafluorophosphate, 0.5 ml of DMF, and 11 μl of triethylamine were added and the resultant was stirred overnight. Following dilution with water and acetonitrile, a crude purified substance that had been purified by purification step A was obtained. The obtained crude purified substance was added with 1 ml of trifluoroacetic acid and stirred for an hour. Thereafter, the solvent was distilled away, and the obtained residue was purified by purification step A to obtain the title compound.
Yield: 5.2 mg

Example 16

Synthesis of 3-[(4S)-4-amino-4-(5-benzyl-1,3,4-oxadiazol-2-yl)butanamide]-5-chloro-2-hydroxybenzene-1-sulfonic acid Step 1

Synthesis of (4S)-4-(5-benzyl-1,3,4-oxadiazole-2-yl)-4-[(tert-butoxy)carbonyl]amino/butanoic acid benzyl ester 337 mg (1 mmol) of Boc-Glu (OBzl)-OH and 150 mg (1 mmol) of 2-phenylacetohydrazide were dissolved in methylene chloride, to which 235 mg of 1-(3-dimethylamino-propyl)-3-ethylcarbodiimide hydrochloride, 183 mg of 1-hydroxybenzotriazole monohydrate and 278 μl of triethylamine were sequentially added. Following agitation at room temperature for 3 hours, ethyl acetate, 1M aqueous sodium hydroxide solution, 1M hydrochloric acid and saturated saline were used for aftertreatment, and then the solvent was distilled away to obtain 0.392 g of a crude purified substance. The obtained crude purified substance was dissolved in 5 ml of methylene chloride, added with 260 mg of Burgess reagent and stirred for three days. Ethyl acetate, 1M aqueous sodium hydroxide solution, 1M hydrochloric acid and saturated saline were used for aftertreatment, and then the solvent was distilled away and the resultant was purified by silica gel column chromatography to obtain the title compound.
Yield: 96 mg Step 2

A similar operation to Step 2 in Example 15 was performed on the compound obtained in Step 1 to obtain the title compound.
Yield: 27.6 mg

Example 17

Synthesis of 3-[(4S)-4-amino-5-oxo-5-(2-phenylacetohydrazide)pentanamide]-5-chloro-2-hydroxybenzene-1-sulfonic acid The compound was obtained as a by-product during the operation in Example 16.
Yield: 44.4 mg

Example 18

Synthesis of 3-[(4S)-4-amino-4-(5-benzyl-1,3,4-oxadiazol-2-yl)butanamide]benzene-1-sulfonic acid In Example 16, the title compound was obtained by performing a similar operation except that 3-amino-5-chloro-2-hydroxybenzenesulfonic acid used in Step 2 was replaced with 3-aminobenzenesulfonic acid.
Yield: 15.6 mg

Example 19

Synthesis of 3-[(4S)-4-amino-4-[5-(4-bromophenyl)-1,3,4-oxadiazole-2-yl]butanamide]-5-chloro-2-hydroxybenzene-1-sulfonic acid The title compound was obtained through a similar operation except that 2-phenylacetohydrazide used in Step 1 in Example 16 was replaced with 4-bromobenzhydrazide.
Yield: 48.9 mg

Example 20

Synthesis of 3-[(4S)-4-amino-4-[5-(4-bromophenyl)-1,3,4-oxadiazole-2-yl]butanamide]benzene-1-sulfonic acid The title compound was obtained through a similar operation except that 2-phenylacetohydrazide used in Step 1 in Example 16 was replaced with 4-bromobenzhydrazide, and 3-amino-5-chloro-2-hydroxybenzenesulfonic acid used in Step 2 was replaced with 3-aminobenzenesulfonic acid.
Yield: 73.2 mg

Example 21

Synthesis of 3-[(4S)-4-amino-4-(5-phenyl-1,3,4-oxadiazol-2-yl)butanamide]-5-chloro-2-hydroxybenzene-1-sulfonic acid The title compound was obtained by performing Steps 1 and 2 except that benzhydrazide was used instead of 2-phenylacetohydrazide used in Step 1 in Example 16.
Yield: 25.6 mg

Example 22

Synthesis of 3-[(4S)-4-amino-4-(benzylcarbamoyl)butanamide]-5-chloro-2-hydroxybenzene-1-sulfonic acid 2.0 mmol of Boc-Glu (OBzl)-OH, 2.2 mmol of 1-(3-dimethylamino-propyl)-3-ethylcarbodiimide hydrochloride and 2.2 mmol of 1-hydroxybenzotriazole monohydrate were dissolved in methylene chloride, to which 2.5 mmol of triethylamine was added. To this, 2.0 mmol of benzylamine was added and stirred overnight. Ethyl acetate, 1M aqueous sodium hydroxide solution, 1M hydrochloric acid and saturated saline were used for aftertreatment, and then the solvent was distilled away. The resultant residue was dissolved in 5 ml of THF, 2.5 ml of methanol and 2.5 ml of water, added with 90 mg of lithium hydroxide and stirred at room temperature for two hours. Ethyl acetate, 1M hydrochloric acid and saturated saline were used for aftertreatment, and then the solvent was distilled away to obtain 440 mg of residue. The obtained residue was added with 261 mg of 1-hydroxy-7-azabenzotriazole, 730 mg of O-(7-azabenzotriazole-1-yl)-N,N,N',N'-tetramethyluronium hexafluorophosphate and 330 mg of 3-amino-5-chloro-2-hydroxybenzenesulfonic acid, and the resultant was dissolved in 5 ml of DMF. To this, 412 μl of triethylamine was added and stirred at room temperature overnight. After distilling the solvent away, the resultant was purified by employing purification step A to obtain a crude product of the title compound in protected form. The obtained crude product was dissolved in 5 ml of methylene chloride and 3 ml of trifluoroacetic acid and stirred for 2 hours. After distilling the solvent away, the resultant was purified by employing purification step A to obtain the title compound.
Yield: 76.3 mg

Example 23

Synthesis of 3-[(4S)-4-amino-4-[(2-phenylethyl)carbamoyl]butanamide]-5-chloro-2-hydroxybenzene-1-sulfonic acid 2.0 mmol of Boc-Glu (OMe)-OH, 2.2 mmol of 1-(3-dimethylamino-propyl)-3-ethylcarbodiimide hydrochloride and 2.2 mmol of 1-hydroxybenzotriazole monohydrate were dissolved in methylene chloride, to which 2.5 mmol of triethylamine was added. To this, 2.0 mmol of 2-phenylethylamine was added and stirred overnight. Ethyl acetate, 1M aqueous sodium hydroxide solution, 1M hydrochloric acid and saturated saline were used for aftertreatment, and then the solvent was distilled away. The obtained residue was dissolved in 5 ml of THF, 2.5 ml of methanol and 2.5 ml of water, to which 90 mg of lithium hydroxide was added and stirred at room temperature for 2 hours. Ethyl acetate, 1M hydrochloric acid and saturated saline were used for aftertreatment, and then the solvent was distilled away to obtain 440 mg of residue. The obtained residue was added with 261 mg of 1-hydroxy-7-azabenzotriazole, 730 mg of O-(7-azabenzotriazole-1-yl)-N,N,N',N'-tetramethyluronium hexafluorophosphate and 330 mg of 3-amino-5-chloro-2-hydroxybenzenesulfonic acid, which was dissolved in 5 ml of DMF. To this, 412 μl of triethylamine was added and stirred at room temperature overnight. After distilling the solvent away, the resultant was purified by employing purification step A to obtain a crude product of the title compound in protected form. The obtained crude product was dissolved in 5 ml of methylene chloride and 3 ml of trifluoroacetic acid, and stirred for 2 hours. After distilling the solvent away, water and acetonitrile were added for deposition and the deposited solid substance was filtrated to obtain the title compound.
Yield: 151.9 mg

Example 24

Synthesis of 3-[(4S)-4-amino-4-[(3-phenylpropyl)carbamoyl]butanamide]-5-chloro-2-hydroxybenzene-1-sulfonic acid The title compound was obtained through a similar operation except that 2-phenylethylamine in Example 23 was replaced with 3-phenylpropylamine.
Yield: 126.7 mg

Example 25

Synthesis of 3-[(4S)-4-amino-4-[(5-phenylbutyl)carbamoyl]butanamide]-5-chloro-2-hydroxybenzene-1-sulfonic acid The title compound was obtained through a similar operation except that 2-phenylethylamine in Example 23 was replaced with 4-phenylbutylamine.
Yield: 135.9 mg

Example 26

Synthesis of 3-[(4S)-4-amino-4-[5-[4-(dimethylamino)phenyl]-1,3,4-oxadiazole-2-yl]butanamide]-5-chloro-2-hydroxybenzene-1-sulfonic acid The title compound was obtained by carrying out Steps 1 and 2 except that 4-(dimethylamino)benzhydrazide was used instead of 2-phenylacetohydrazide used in Step 1 in Example 16.
Yield: 48.6 mg

Example 27

Synthesis of 3-[(4S)-4-amino-4-[5-(thiophene-2-yl)-1,3,4-oxadiazolo-2-yl]butanamide]-5-chloro-2-hydroxybenzene-1-sulfonic acid The title compound was obtained by carrying out Steps 1 and 2 except that 2-thiophenecarboxylic acid hydrazide was used instead of 2-phenylacetohydrazide used in Step 1 in Example 16.
Yield: 40.1 mg

Example 28

Synthesis of (2S)-2-amino-3-{[(2-hydroxy-3-sulfophenyl)carbamoyl]amino}propanoic acid The compound obtained in Example 6 was dissolved in water and methanol, to which a catalyst amount of Pd/C was added, and the resultant was stirred for three days in a hydrogen atmosphere. After filtrating the catalyst, the solvent was distilled away, and the resultant was purified using purification step A to obtain the title compound.
Yield: 1.2 mg Example 29

Synthesis of 3-{[(2-aminoethyl)carbamoyl]amino}-5-chloro-2-hydroxybenzene-1-sulfonic acid The title compound was obtained through a similar operation except that tert-butyl N-(2-aminoethyl)carbamate was used instead of 3-amino-N-(tert-butoxycarbonyl)-L-alanine tert-butylester hydrochloride used in Example 6.
Yield: 1.0 mg Example 30

Synthesis of 3-[(4S)-4-amino-4-{[2-(1H-indole-3-yl)ethyl]carbamoyl}butanamide]-5-chloro-2-hydroxybenzene-1-sulfonic acid The title compound was obtained through a similar operation except that tryptamine was used instead of 2-phenylethylamine used in Example 23.
Yield: 61.9 mg Example 31

Synthesis of 3-[(4S)-4-amino-4-{[2-(3-methoxyphenyl)ethyl]carbamoyl}butanamide]-5-chloro-2-hydroxybenzene-1-sulfonic acid The title compound was obtained through a similar operation except that 3-methoxyphenethylamine was used instead of 2-phenylethylamine used in Example 23.
Yield: 80.8 mg Example 32

Synthesis of 3-[(4S)-4-amino-4-{[2-(3-chlorophenyl)ethyl]carbamoyl}butanamide]-5-chloro-2-hydroxybenzene-1-sulfonic acid The title compound was obtained through a similar operation except that 3-chlorophenethylamine was used instead of 2-phenylethylamine used in Example 23.
Yield: 122 mg Example 33

Synthesis of 3-[(4S)-4-amino-4-{[3-(1H-imidazole-1-yl)propyl]carbamoyl}butanamide]-5-chloro-2-hydroxybenzene-1-sulfonic acid The title compound was obtained through a similar operation except that 1-(3-aminopropyl)imidazole was used instead of 2-phenylethylamine used in Example 23.
Yield: 20 mg Example 34

Synthesis of 3-[(4S)-4-amino-4-(methanesulfonylcarbamoyl)butanamide]-5-chloro-2-hydroxybenzene-1-sulfonic acid 337 mg (1 mmol) of Boc-Glu (OBzl)-OH, 95 mg (1 mmol) of methanesulfonamide, 250 mg (1.2 mmol) of dicyclohexylcarbodiimide and a catalyst amount of 4-(dimethylamino)pyridine were added and dissolved in 5 ml of methylene chloride. After agitation at room temperature overnight, the insoluble matter was filtrated and the solution was distilled away. Thereafter, ethyl acetate, 1M hydrochloric acid and saturated saline were used for aftertreatment. The resulting residue was dissolved in ethyl acetate, to which a catalyst amount of Pd/C was added, and the resultant was stirred in a hydrogen atmosphere overnight. After the catalyst was filtrated, the solvent was distilled away to obtain a residue. To the obtained residue, 220 mg of 3-amino-5-chloro-2-hydroxybenzenesulfonic acid, then 150 mg of 1-hydroxy-7-azabenzotriazole and 400 mg of O-(7-azabenzotriazole-1-yl)-N,N,N',N'-tetramethyluronium hexafluorophosphate were added, and 1 ml of DMF were added. Following addition of 200 µl of triethylamine, agitation took place overnight. After confirming the reaction progress, the reaction solution was diluted with water and acetonitrile and purified by purification step A. The resulting crude purified substance was dissolved in 2 ml of methylene chloride and 2 ml of trifluoroacetic acid. After two hours of agitation, the solvent was distilled away and the resultant was purified by purification step A to obtain the title compound.
Yield: 15.3 mg Example 35

Synthesis of 3-[(4S)-4-amino-4-(methanesulfonylcarbamoyl)butanamide]benzene-1-sulfonic acid The title compound was obtained through a similar operation except that 3-aminobenzenesulfonic acid was used instead of 3-amino-5-chloro-2-hydroxybenzenesulfonic acid used in Example 34.
Yield: 7.6 mg Example 36

Synthesis of 5-[(4S)-4-amino-4-(methanesulfonylcarbamoyl)butanamide]-3-chloro-2-methylbenzene-1-sulfonic acid The title compound was obtained through a similar operation except that 5-amino-3-chloro-2-methylbenzenesulfonic acid was used instead of 3-amino-5-chloro-2-hydroxybenzenesulfonic acid used in Example 34.
Yield: 108.4 mg Example 37

Synthesis of 3-[(4S)-4-amino-4-(methanesulfonylcarbamoyl)butanamide]-5-chloro-4-methylbenzene-1-sulfonic acid The title compound was obtained through a similar operation except that 3-amino-5-chloro-4-methylbenzenesulfonic acid was used instead of 3-amino-5-chloro-2-hydroxybenzenesulfonic acid used in Example 34.
Yield: 86.8 mg Example 38

Synthesis of 3-[(4S)-4-amino-4-(hydroxycarbamoyl)butanamide]benzene-1-sulfonic acid 337 mg (1 mmol) of Boc-Glu-OBzl, 173 mg (1 mmol) of 3-aminobenzenesulfonic acid, and 420 mg (1.1 mmol) of O-(7-azabenzotriazole-1-yl)-N,N,N',N'-tetramethyluronium hexafluorophosphate were dissolved in 2 ml of DMF, added with 200 μl of triethylamine and stirred at room temperature overnight. Following dilution with water and acetonitrile, purification step A was used to obtain a crude purified substance. 50 mg of the obtained crude purified substance was dissolved in 1 ml of ethanol, to which 200 μl of a 50% aqueous hydroxylamine solution was added. Following agitation at room temperature overnight, the solvent was distilled away, and the resultant was purified using purification step A to obtain the title compound.

Yield: 7.49 mg

Example 39

Synthesis of 5-[(4S)-4-amino-4-(hydroxycarbamoyl) butanamide]-3-chloro-2-methylbenzene-1-sulfonic acid The title compound was obtained through a similar operation except that 5-amino-3-chloro-2-methylbenzenesulfonic acid was used instead of 3-aminobenzenesulfonic acid in Example 38.

Yield: 5.4 mg

Example 40

Synthesis of 3-[(4S)-4-amino-4-(hydroxycarbamoyl) butanamide]-5-chloro-4-methylbenzene-1-sulfonic acid The title compound was obtained through a similar operation except that 3-amino-5-chloro-4-methylbenzenesulfonic acid was used instead of 3-aminobenzenesulfonic acid in Example 38.

Yield: 7.88 mg

Example 41

Synthesis of 3-[(4S)-4-amino-4-(hydroxycarbamoyl) butanamide]-5-chloro-2-hydroxybenzene-1-sulfonic acid The title compound was obtained through a similar operation except that 3-amino-5-chloro-2-hydroxybenzenesulfonic acid was used instead of 3-aminobenzenesulfonic acid in Example 38.

Yield: 5.7 mg

Example 42

Synthesis of (2S)-2-amino-4-[(6-sulfopyridine-2-yl) carbamoyl]butanoic acid trifluoroacetic acid salt 50 mg (0.16 mmol) of Boc-Glu-OtBu, 35 mg (0.16 mmol) of 1-(3-dimethylamino-propyl)-3-ethylcarbodiimide hydrochloride and 28 mg (0.16 mmol) of 1-hydroxybenzotriazole monohydrate were suspended in 1.0 ml of methylene chloride, to which 28 mg (0.16 mmol) of 6-amino-2-pyridinesulfonic acid was added. Following agitation at room temperature overnight, the resultant was subjected to extraction with ethyl acetate/water. The organic layer was washed with saturated saline, and then added with sodium sulfate for drying. The organic layer was subjected to vacuum condensation, 4.0 ml of TFA was added to the resulting residue, and the resultant was stirred overnight. 6.5 mg of the title compound was obtained using purification step A.

Yield: 6.5 mg

Example 43

Synthesis of (2S,3S)-2-amino-3-{[(3-sulfophenyl) carbamoyl]oxy}butanoic acid

Step 1

Synthesis of Boc-Allo-Thr-OMe 340 mg (2.0 mmol) of Allo-Thr-OMe hydrochloride was dissolved in 8.0 ml of methylene chloride, and added with 558 μl (4.0 mmol) of triethylamine and 436 mg (2.0 mmol) of di-tert-butyl dicarbonate. Following agitation at room temperature for 4 hours, the resultant was subjected to vacuum condensation and extraction with ethyl acetate/water. The organic layer was washed with saturated saline and then added with sodium sulfate for drying. The organic layer was subjected to vacuum condensation to obtain a crude product of the title compound.

Yield: 460 mg

MS (ESI, m/z): 234 [M+H]+

Step 2

Synthesis of (2S,3S)-2-amino-3-{[(3-sulfophenyl) carbamoyl]oxy}butanoic acid 117 mg of the compound obtained in Step 1, 148 mg (0.5 mmol) of triphosgene and 87 mg (0.5 mmol) of 3-aminobenzenesulfonic acid were dissolved in 2.0 ml of methylene chloride, added with 70 μl (0.5 mmol) of triethylamine and stirred at room temperature overnight. Following addition of 1.0 ml of ammonia-methanol solution, the solvent was distilled away. Purification step A was employed to obtain a crude product of (2S,3S)-2-(N-tert-butoxycarbonylamino)-3-{[(3-sulfophenyl)carbamoyl]oxy}butanic acid methyl ester. To this, 20 mg (1.2 mmol) of lithium hydroxide and 2.0 ml of water were added and stirred at room temperature overnight. Subsequently, 4.0 ml of TFA was added and stirred at room temperature for another 5 hours. After distilling the solvent away, purification step A was employed to obtain 5.2 mg of the title compound.

Yield: 5.2 mg

Example 44

Synthesis of (2S,3S)-2-amino-3-{[(5-chloro-2-hydroxy-3-sulfophenyl)carbamoyl]oxy}butanoic acid The title compound was obtained through a similar operation except that 3-aminobenzenesulfonic acid used in Example 43 was replaced with 3-amino-5-chloro-2-hydroxybenzenesulfonic acid.

Yield: 32.1 mg

Example 45

Synthesis of (2S,3R)-2-amino-3-{[(5-chloro-2-hydroxy-3-sulfophenyl)carbamoyl]oxy}butanoic acid The title compound was obtained through a similar operation except that Boc-Allo-Thr-OMe and 3-aminobenzenesulfonic acid were replaced with Boc-Thr-OMe and 3-amino-5-chloro-2-hydroxybenzenesulfonic acid, respectively, after Step 2 in Example 43.

Yield: 33.4 mg

Example 46

Synthesis of (2S)-2-amino-3-{[(3-sulfophenyl)carbamothioyl]amino}propanoic acid 35 mg (0.2 mmol) of 3-aminobenzenesulfonic acid and 57 mg (0.68 mmol) of sodium hydrogen carbonate were added to a mixed solvent of 2.0 ml of water and 0.5 ml of THF, and stirred at room temperature for 15 minutes. 20 µl (0.26 mmol) of thiophosgene was added and stirred at room temperature for another 40 minutes. Subsequently, 60 mg (0.2 mmol) of tert-butyl (2S)-3-amino-2-{[(tert-butoxy)carbonyl]amino}propanoate hydrochloride was added and stirred overnight. Following extraction with ethyl acetate, the solvent was distilled away, and 4.0 ml of trifluoroacetic acid was added to the residue, and the resultant was stirred at room temperature for 5 hours. After distilling the solvent away, purification step A was used to obtain 3.5 mg of the title compound.

Yield: 3.5 mg

Example 47

Synthesis of (2S)-2-amino-3-{[(3-chloro-2-methyl-5-sulfophenyl)carbamothioyl]amino}propanoic acid The title compound was obtained through a similar operation except that 3-aminobenzenesulfonic acid used in Example 46 was replaced with 3-amino-5-chloro-4-methylbenzenesulfonic acid.

Yield: 6.9 mg

Example 48

Synthesis of (2S)-2-amino-3-{[(3-chloro-4-methyl-5-sulfophenyl)carbamothioyl]amino}propanoic acid The title compound was obtained through a similar operation except that 3-aminobenzenesulfonic acid used in Example 46 was replaced with 5-amino-3-chloro-2-methylbenzenesulfonic acid.

Yield: 5.8 mg

Example 49

Synthesis of 3-[(4S)-4-amino-4-(carbamoyl)butanamide]benzene-1-sulfonic acid

Step 1

Synthesis of (4S)-4-(N-tert-butoxycarbonylamino)-4-(carbamoyl)butanoic acid 1010 mg (3.0 mmol) of Boc-Glu (OBzl)-OH, 316 µl (3.3 mmol) of ethyl chloroformate and 460 µl (3.3 mmol) of triethylamine were suspended in 12.0 ml of tetrahydrofuran, to which 2.0 ml of a concentrated aqueous ammonia solution was added. Following agitation at room temperature overnight, the resultant was subjected to extraction with ethyl acetate/water. The organic layer was washed with saturated saline and then sodium sulfate was added for drying. The organic layer was subjected to vacuum condensation, and the resulting residue was added with 100 mg of 10% Pd/C and 12.0 ml of methanol and stirred at room temperature overnight in a hydrogen atmosphere under a normal pressure. After the reaction, the catalyst was filtrated away and the solvent was distilled away to obtain a crude purified substance of the title compound.

MS (ESI, m/z): 275 [M+H]+

Step 2

Synthesis of 3-[(4S)-4-amino-4-(carbamoyl)butanamide]-benzene-1-sulfonic acid 100 mg (0.37 mmol) of the compound obtained in Step 1, 190 mg (0.5 mmol) of O-(7-azabenzotriazole-1-yl)-N,N,N',N'-tetramethyluronium hexafluorophosphate, 70 mg (0.5 mmol) of 1-hydroxy-7-azabenzotriazole and 65 mg (0.37 mmol) of 3-aminobenzenesulfonic acid were suspended in 2.0 ml of methylene chloride, added with 0.5 ml pyridine and stirred at room temperature overnight. After distilling the solvent away, purification step A was used to obtain a crude product of 3-[(4S)-4-(N-tert-butoxycarbonylamino)-4-(carbamoyl)butanamide]-benzene-1-sulfonic acid. To this, 4.0 ml of TFA was added and stirred at room temperature for 2 hours. After distilling the solvent away, purification step A was used to obtain 1.6 mg of the title compound.

Yield: 1.6 mg

Example 50

Synthesis of 3-[(4S)-4-amino-4-(carbamoyl)butanamide]-5-chloro-2-hydroxybenzene-1-sulfonic acid The title compound was obtained through a similar operation except that 3-aminobenzenesulfonic acid used in Example 49 was replaced with 3-amino-5-chloro-2-hydroxybenzenesulfonic acid.

Yield: 4.1 mg

Example 51

Synthesis of 5-[(4S)-4-amino-4-(carbamoyl)butanamide]-3-chloro-2-methylbenzene-1-sulfonic acid The title compound was obtained through a similar operation except that 3-aminobenzenesulfonic acid used in Example 49 was replaced with 3-amino-5-chloro-6-methylbenzenesulfonic acid.

Yield: 5.3 mg

Example 52

Synthesis of 3-[(4S)-4-amino-4-(5-ethyl-1,3,4-oxadiazole-2-yl)butanamide]-5-chloro-2-hydroxybenzene-1-sulfonic acid

Step 1

Synthesis of (4S)-4-(N-tert-butoxycarbonylamino)-4-(N'-propionyl carbohydrazide)butanoic acid benzyl ester 674 mg (2.0 mmol) of Boc-Glu (OBzl)-OH, 420 mg (2.2 mmol) of 1-(3-dimethylaminopropyl)-3-ethylcarbodiimide hydrochloride, 336 mg (2.2 mmol) of 1-hydroxybenzotriazole monohydrate and 230 mg (2.6 mmol) of propionic acid hydrazide were suspended in 5.0 ml of methylene chloride, to which 557 µl (4.0 mmol) of triethylamine was added. Following agitation at room temperature overnight, vacuum condensation was performed and purification step A was used to obtain a crude purified substance of the title compound.

Yield: 500 mg

MS (ESI, m/z): 380 [M+H]+

Step 2

Synthesis of (4S)-4-(N-tert-butoxycarbonylamino)-4-(5-ethyl-1,3,4-oxadiazole-2-yl)butanoic acid 500 mg of the compound obtained in Step 1 and 182 mg (0.76 mmol) of Burgess reagent were dissolved in 4.0 ml methylene chloride, and stirred at room temperature overnight. After distilling the solvent away, silica gel column chromatography was used for partial purification. To the residue, 50 mg of 10% Pd/C and 4.0 ml of ethyl acetate were added and the resultant was stirred at room temperature overnight in a hydrogen atmosphere under a normal pressure. The catalyst was filtrated away after the reaction, and the solvent was distilled away to obtain a crude purified substance of the title compound.

Yield: 270 mg
MS (ESI, m/z): 300[M+H]+

Step 3

Synthesis of 3-[(4S)-4-amino-4-(5-ethyl-1,3,4-oxadiazole-2-yl)butanamide]-5-chloro-2-hydroxybenzene-1-sulfonic acid 270 mg of the compound obtained in Step 2, 266 mg (0.7 mmol) of O-(7-azabenzotriazole-1-yl)-N,N,N',N'-tetramethyluronium hexafluorophosphate, 100 mg (0.7 mmol) of 1-hydroxy-7-azabenzotriazole and 160 mg (0.7 mmol) of 3-amino-5-chloro-2-hydroxybenzenesulfonic acid were suspended in 4.0 ml of methylene chloride, to which 0.3 ml of triethylamine was added and the resultant was stirred at room temperature overnight. After distilling the solvent away, purification step A was used to obtain a crude product of 3-[(4S)-4-(N-tert-butoxycarbonylamino)-4-(5-ethyl-1,3,4-oxadiazole-2-yl)butanamide]-5-chloro-2-hydroxybenzene-1-sulfonic acid. To this, 4.0 ml of TFA was added and stirred at room temperature for 2 hours. After distilling the solvent away, purification step A was used to obtain 9.0 mg of the title compound.

Yield: 9.0 mg

Example 53

Synthesis of 3-[(4S)-4-amino-4-(N'-propanoylhydrazinecarbonyl)butanamide]-5-chloro-2-hydroxybenzene-1-sulfonic acid The compound was obtained as a by-product in Step 3 in Example 52.

Yield: 12.8 mg

Example 54

Synthesis of 3-[(4S)-4-amino-4-(5-propyl-1,3,4-oxadiazole-2-yl)butanamide]-5-chloro-2-hydroxybenzene-1-sulfonic acid The title compound was obtained through a similar operation except that propionic acid hydrazide used in Step 1 in Example 52 was replaced with butyric acid hydrazide.

Yield: 12.0 mg

Example 55

Synthesis of 3-[(4S)-4-amino-4-[5-(propane-2-yl)-1,3,4-oxadiazole-2-yl]butanamide]-5-chloro-2-hydroxybenzene-1-sulfonic acid The title compound was obtained through a similar operation except that propionic acid hydrazide used in Step 1 in Example 52 was replaced with isobutyric acid hydrazide.

Yield: 11.8 mg

Example 56

Synthesis of 3-[(4S)-4-amino-4-(ethylcarbamoyl)butanamide]-5-chloro-2-hydroxybenzene-1-sulfonic acid

Step 1

Synthesis of (4S)-4-(N-tert-butoxycarbonylamino)-4-(ethylcarbamoyl)butanoic acid 337 mg (1.0 mmol) of Boc-Glu (OBzl)-OH, 191 mg (1.0 mmol) of 1-(3-dimethylaminopropyl)-3-ethylcarbodiimide hydrochloride, 152 mg (1.0 mmol) of 1-hydroxybenzotriazole monohydrate and 0.5 ml of triethylamine were suspended in 4.0 ml of DMF, to which 150 µl of 33% aqueous ethylamine solution was added. Following agitation at room temperature overnight, extraction was performed with ethyl acetate/water. The organic layer was washed with saturated saline and added with sodium sulfate for drying. The organic layer was subjected to vacuum condensation. The resulting residue was dissolved in 4.0 ml of 10% aqueous sodium hydroxide solution and stirred overnight. Purification step A was used to obtain a crude product of the title compound.

MS (ESI, m/z): 275 [M+H]+

Step 2

Synthesis of 3-[(4S)-4-amino-4-(ethylcarbamoyl)butanamide]-5-chloro-2-hydroxybenzene-1-sulfonic acid 220 mg (0.8 mmol) of the compound obtained in Step 1, 300 mg (0.8 mmol) of O-(7-azabenzotriazole-1-yl)-N,N,N',N'-tetramethyluronium hexafluorophosphate, 110 mg (0.8 mmol) of 1-hydroxy-7-azabenzotriazole and 180 mg (0.8 mmol) of 3-amino-5-chloro-2-hydroxybenzenesulfonic acid were suspended in 4.0 ml of methylene chloride, to which 0.5 ml of triethylamine was added and stirred at room temperature overnight. After distilling the solvent away, purification step A was used to obtain 160 mg of a crude product of 3-[(4S)-4-(N-tert-butoxycarbonylamino)-4-(ethylcarbamoyl)butanamide]-5-chloro-2-hydroxybenzene-1-sulfonic acid. 144 mg of this crude product was dissolved in 4.0 ml of TFA and stirred at room temperature for 2 hours. After distilling the solvent away, purification step A was used to obtain 5.8 mg of the title compound.

Yield: 5.8 mg

Example 57

Synthesis of 3-[(4S)-4-amino-4-(butylcarbamoyl) butanamide]-5-chloro-2-hydroxybenzene-1-sulfonic acid The title compound was obtained through a similar operation except that an aqueous ethylamine solution used in Step 1 in Example 56 was replaced with n-butylamine.
Yield: 11.5 mg

Example 58

Synthesis of 3-[(4S)-4-amino-5-(morpholine-4-yl)-5-oxopentanamide]-5-chloro-2-hydroxybenzene-1-sulfonic acid The title compound was obtained through a similar operation except that an aqueous ethylamine solution used in Step 1 in Example 56 was replaced with morpholine.
Yield: 7.6 mg

Example 59

Synthesis of 3-[(4S)-4-amino-4-(cyclohexylcarbamoyl)butanamide]-5-chloro-2-hydroxybenzene-1-sulfonic acid The title compound was obtained through a similar operation except that an aqueous ethylamine solution used in Step 1 in Example 56 was replaced with cyclohexylamine.
Yield: 3.9 mg

Example 60

Synthesis of 3-[(4S)4-amino-4-(cycloheptylcarbamoyl)butanamide]-5-chloro-2-hydroxybenzene-1-sulfonic acid The title compound was obtained through a similar operation except that an aqueous ethylamine solution used in Step 1 in Example 56 was replaced with cycloheptylamine.
Yield: 1.6 mg

Example 61

Synthesis of 3-[(4S)-4-amino-4-[(benzenesulfonyl) carbamoyl]butanamide]benzene-1-sulfonic acid

Step 1

Synthesis of (4S)-4-(N-tert-butoxycarbonylamino)-4-[(benzenesulfonyl)carbamoyl]butanoic acid 1.7 g (5.0 mmol) of Boc-Glu (OBzl)-OH, 1.03 g (5.0 mmol) of dicyclohexylcarbodiimide and 611 mg (5.0 mmol) of 4-(dimethylamino)pyridine were suspended in 20 ml of methylene chloride, to which 866 mg (5.0 mmol) of benzenesulfonamide was added. Following agitation at room temperature overnight, extraction was performed with ethyl acetate/1N hydrochloric acid. The organic layer was washed with saturated saline and then added with sodium sulfate for drying. The organic layer was subjected to vacuum condensation. To the resulting residue, 100 mg of 10% Pd/C and 20 ml of methanol were added and stirred overnight in a hydrogen atmosphere under a normal pressure. After filtrating the catalyst away, the solvent was distilled away and purification step A was used to obtain a crude product of the title compound.
MS (ESI, m/z): 387 [M+H]+

Step 2

Synthesis of 3-[(4S)-4-amino-4-[(benzenesulfonyl) carbamoyl]butanamide]benzene-1-sulfonic acid 100 mg of the compound obtained in Step 1, 114 mg (0.3 mmol) of O-(7-azabenzotriazole-1-yl)-N,N,N',N'-tetramethyluronium hexafluorophosphate, 40 mg (0.8 mmol) of 1-hydroxy-7-azabenzotriazole and 55 mg (0.3 mmol) of 3-aminobenzenesulfonic acid were suspended in 1.0 ml of methylene chloride, to which 0.1 ml of triethylamine was added and stirred at room temperature overnight. After distilling the solvent away, purification step A was used to obtain a crude product of 3-[(4S)-4-(N-tert-butoxycarbonylamino)-4-[(benzenesulfonyl)carbamoyl]butanamide]benzene-1-sulfonic acid. This crude product was dissolved in 4.0 ml of TFA and the resultant was stirred at room temperature for 2 hours. After distilling the solvent away, purification step A was used to obtain 14.1 mg of the title compound.
Yield: 14.1 mg

Example 62

Synthesis of 3-[(4S)-4-amino-4-[(benzenesulfonyl) carbamoyl]butanamide]-5-chloro-2-hydroxybenzene-1-sulfonic acid The title compound was obtained through a similar operation except that 3-aminobenzenesulfonic acid used in Step 2 in Example 61 was replaced with 3-amino-5-chloro-2-hydroxybenzenesulfonic acid.
Yield: 3.2 mg

Example 63

Synthesis of 3-[(4S)-4-amino-4-[(benzenesulfonyl) carbamoyl]butanamide]-5-chloro-4-methylbenzene-1-sulfonic acid The title compound was obtained through a similar operation except that 3-aminobenzenesulfonic acid used in Step 2 in Example 61 was replaced with 3-amino-5-chloro-4-hydroxybenzenesulfonic acid.
Yield: 31.4 mg

Example 64

Synthesis of 3-[(4S)-4-amino-4-(methylcarbamoyl) butanamide]benzene-1-sulfonic acid

Step 1

Synthesis of (4S)-4-(N-tert-butoxycarbonylamino)-4-(methylcarbamoyl)butanoic acid 1010 mg (3 mmol) of Boc-Glu (OBzl)-OH, 600 mg (3.2 mmol) of 1-(3-dimethylaminopropyl)-3-ethylcarbodiimide hydrochloride and 460 mg (3.1 mmol) of 1-hydroxybenzotriazole monohydrate were suspended in 12 ml of DMF, to which 300 µl (2.0 mmol) of a 40% aqueous methylamine solution was added. Following agitation at room temperature overnight, extraction was performed with ethyl acetate/water.

The organic layer was washed with saturated saline, and the resultant was added with sodium sulfate for drying. The organic layer was subjected to vacuum condensation, and the resultant residue was dissolved in 10 ml of methanol, added with 100 mg of 10% Pd/C, and then stirred overnight in a hydrogen atmosphere. After the catalyst was filtrated away and the solvent was distilled away, purification step A was used to obtain a crude product of the title compound.

MS (ESI, m/z): 261 [M+H]+

Step 2

Synthesis of 3-[(4S)-4-amino-4-(methylcarbamoyl) butanamide]benzene-1-sulfonic acid 100 mg of the compound obtained in Step 1, 76 mg (0.2 mmol) of O-(7-azabenzotriazole-1-yl)-N,N,N',N'-tetramethyluronium hexafluorophosphate, 28 mg (0.2 mmol) of 1-hydroxy-7-azabenzotriazole and 36 mg (0.2 mmol) of 3-aminobenzenesulfonic acid were suspended in 1.0 ml of methylene chloride, to which 0.1 ml of triethylamine was added and the resultant was stirred at room temperature overnight. After distilling the solvent away, purification step A was used to obtain a crude product of 3-[(4S)-4-(N-tert-butoxycarbonylamino)-4-(methylcarbamoyl)butanamide]benzene-1-sulfonic acid. This crude product was dissolved in 4.0 ml of TFA, and stirred at room temperature for 2 hours. After distilling the solvent away, purification step A was used to obtain 9.9 mg of the title compound.

Yield: 9.9 mg

Example 65

Synthesis of 3-[(4S)-4-amino-4-(methylcarbamoyl) butanamide]-5-chloro-4-methylbenzene-1-sulfonic acid The title compound was obtained through a similar operation except that 3-aminobenzenesulfonic acid used in Step 2 in Example 64 was replaced with 3-amino-5-chloro-4-methylbenzenesulfonic acid.

Yield: 4.1 mg

Example 66

Synthesis of 3-({[(2S)-2-amino-3-methoxy-3-oxopropyl]carbamoyl}amino)benzene-1-sulfonic acid To 127 mg (0.5 mmol) of (2S)-3-amino-2-{[(tert-butoxy)carbonyl]amino}propanoic acid methylester hydrochloride, 87 mg (0.5 mmol) of 3-aminobenzenesulfonic acid and 97 mg (0.6 mmol) of N,N-carbonyl diimidazole, 1 ml of methylene chloride and 1 ml of tetrahydrofuran were added and stirred at room temperature overnight. After distilling the solvent away, purification was carried out using purification step A to obtain a crude purified substance of the title compound in protected form. To the obtained crude purified substance, 1 ml of methylene chloride and 1 ml of trifluoroacetic acid were added and stirred at room temperature for 5 hours. After distilling the solvent away, purification was carried out by purification step A to obtain the title compound.

Yield: 33.15 mg

Example 67

Synthesis of 3-({[(2S)-2-amino-3-methoxy-3-oxopropyl]carbamoyl}amino)-5-chloro-2-hydroxybenzene-1-sulfonic acid The title compound was obtained through a similar operation except that 3-aminobenzenesulfonic acid used in Example 66 was replaced with 3-amino-5-chloro-2-hydroxybenzenesulfonic acid.

Yield: 19.1 mg

Example 68

Synthesis of 5-({[(2S)-2-amino-3-methoxy-3-oxopropyl]carbamoyl}amino)-3-chloro-2-methylbenzene-1-sulfonic acid The title compound was obtained through a similar operation except that 3-aminobenzenesulfonic acid used in Example 66 was replaced with 5-amino-3-chloro-2-methylbenzenesulfonic acid.

Yield: 11.84 mg

Example 69

Synthesis of 3-({[(2S)-2-amino-3-methoxy-3-oxopropyl]carbamoyl}amino)-5-chloro-4-methylbenzene-1-sulfonic acid The title compound was obtained through a similar operation except that 3-aminobenzenesulfonic acid used in Example 66 was replaced with 3-amino-5-chloro-4-methylbenzenesulfonic acid.

Yield: 14.57 mg

Example 70

Synthesis of 3-({[(2S)-2-amino 2-(methylcarbamoyl) ethoxy]carbonyl}amino)benzene-1-sulfonic acid Step 1

Synthesis of t-butyl N-[(1S)-2-hydroxy-1-(methylcarbamoyl)ethyl]carbamate 885 mg (3.0 mmol) of Boc-Ser (OBzl)-OH, 600 mg (3.2 mmol) of 1-(3-dimethylamino-propyl)-3-ethylcarbodiimide hydrochloride and 460 mg (3.1 mmol) of 1-hydroxybenzotriazole monohydrate were dissolved in 12 ml of DMF, to which 300 μl of 40% aqueous methylamine solution was added. Following agitation at room temperature overnight, extraction was performed with ethyl acetate/1N hydrochloric acid. After washing the organic layer with saturated saline, sodium sulfate was added for drying. The organic layer was subjected to vacuum condensation, and the resulting residue was dissolved in 12 ml of methanol, to which 100 mg of 10% Pd/C was added and stirred overnight in a hydrogen atmosphere. Purification step A was used to obtain a crude product of the title compound.

MS (ESI, m/z): 219 [M+H]+

Step 2

Synthesis of 3-({[(2S)-2-amino-2-(methylcarbamoyl)ethoxy]carbonyl}amino)benzene-1-sulfonic acid 80 mg (0.37 mmol) of the compound obtained in Step 1, 40 mg (0.1 mmol) of triphosgene and 60 mg (0.35 mmol) of 3-aminobenzenesulfonic acid were suspended in 2.0 ml of methylene chloride, to which 0.5 ml of pyridine was added and stirred at room temperature overnight. After distilling the solvent away, purification step A was used to obtain an intermediate. This crude product was dissolved in 4.0 ml of trifluoroacetic acid and stirred at room temperature for 15 minutes. After distilling the solvent away, purification step A was used to obtain 6.79 mg of the title compound.

Yield: 6.79 mg

Example 71

Synthesis of 3-({[(2S)-2-amino-2-(methylcarbamoyl)ethoxy]carbonyl}amino)-5-chloro-2-hydroxybenzene-1-sulfonic acid The title compound was obtained through a similar operation except that 3-aminobenzenesulfonic acid used in Example 70 was replaced with 3-amino-5-chloro-2-hydroxybenzenesulfonic acid.

Yield: 26.3 mg

Example 72

Synthesis of 3-({[(2S)-2-amino-2-(methylcarbamoyl)ethoxy]carbonyl}amino)-5-chloro-4-methylbenzene-1-sulfonic acid The title compound was obtained through a similar operation except that 3-aminobenzenesulfonic acid used in Example 70 was replaced with 3-amino-5-chloro-4-methylbenzenesulfonic acid.

Yield: 0.8 mg

Example 73

Synthesis of 3-({[(2S)-2-amino-2-[(benzenesulfonyl)carbamoyl]ethoxy]carbonyl}amino)benzene-1-sulfonic acid

Step 1

Synthesis of t-butyl N-[(1S)-1-[(benzenesulfonyl)carbamoyl]-2-hydroxyethyl]carbamate 885 mg (3.0 mmol) of Boc-Ser (OBzl)-OH, 620 mg (3.0 mmol) of dicyclohexylcarbodiimide and 370 mg (3.0 mmol) of 4-(dimethylamino)pyridine were dissolved in 12 ml of methylene chloride, to which 470 mg (3.0 mmol) of benzenesulfonamide was added. Following agitation at room temperature overnight, extraction was performed with ethyl acetate/1N hydrochloric acid. After washing the organic layer with saturated saline, sodium sulfate was added for drying. The organic layer was subjected to vacuum condensation. The resulting residue was dissolved in 12 ml of methanol, added with 100 mg of 10% Pd/C and stirred overnight in a hydrogen atmosphere. Purification step A was used to obtain a crude product of the title compound.

ESI (m/z): 345 [M+H]+

Step 2

Synthesis of 3-({[(2S)-2-amino-2-[(benzenesulfonyl)carbamoyl]ethoxy]carbonyl}amino)benzene-1-sulfonic acid 80 mg (0.23 mmol) of the compound obtained in Step 1, 40 mg (0.1 mmol) of triphosgene and 40 mg (0.23 mmol) of 3-aminobenzenesulfonic acid were suspended in 2.0 ml of methylene chloride, to which 0.5 ml of pyridine was added and stirred at room temperature overnight. After distilling the solvent away, purification step A was used to obtain an intermediate. This crude product was dissolved in 4.0 ml of trifluoroacetic acid and stirred at room temperature for an hour. After distilling the solvent away, purification step A was used to obtain 21.2 mg of the title compound.

Yield: 21.2 mg

Example 74

Synthesis of 3-({[(2S)-2-amino-2-[(benzenesulfonyl)carbamoyl]ethoxy]carbonyl}amino)-5-chloro-2-hydroxybenzene-1-sulfonic acid The title compound was obtained through a similar operation except that 3-aminobenzenesulfonic acid used in Example 73 was replaced with 3-amino-5-chloro-2-hydroxybenzenesulfonic acid.

Yield: 8.36 mg

Example 75

Synthesis of 3-({[(2S)-2-amino-2-[(benzenesulfonyl)carbamoyl]ethoxy]carbonyl}amino)-5-chloro-4-methylbenzene-1-sulfonic acid The title compound was obtained through a similar operation except that 3-aminobenzenesulfonic acid used in Example 73 was replaced with 3-amino-5-chloro-4-methylbenzenesulfonic acid.

Yield: 8.8 mg

Example 76

Synthesis of (2S)-4-[(5-chloro-2-hydroxy-3-sulfophenyl)carbamoyl]-2-(dimethylamino)butanoic acid

Step 1

Synthesis of (2S)-2-amino-4-[(5-chloro-2-hydroxy-3-sulfophenyl)carbamoyl]butanoic acid 101 mg (0.33 mmol) of Boc-Glu-OtBu, 130 mg (0.33 mmol) of HATU, 45 mg (0.33 mmol) of HOAt and 77 mg (0.33 mmol) of 3-amino-5-chloro-2-hydroxybenzenesulfonic acid were suspended in 2.0 ml of DMF, to which 0.5 ml of pyridine was added and stirred at room temperature overnight. After distilling the solvent away, purification step A was used to obtain an intermediate. This crude product was dissolved in 2.0 ml of TFA and stirred at room temperature for 90 minutes. After distilling the solvent away, purification step A was used to obtain the title compound.

Yield: 90 mg
ESI (m/z): 353, 355 [M+H]+

Step 2

Synthesis of (2S)-4-[(5-chloro-2-hydroxy-3-sulfophenyl)carbamoyl]-2-(dimethylamino)butanoic acid 35 mg (0.1 mmol) of the compound obtained in Step 1 and 30 mg of Pd/C were suspended in 1.0 ml of a 37% aqueous formaldehyde solution and stirred overnight in a hydrogen atmosphere. After filtrating Pd/C away, purification step A was used to obtain 11.2 mg of the title compound.

Yield: 11.2 mg

Example 77

Synthesis of (2S)-2-amino-3-{[(3-sulfophenyl)carbamoyl]amino}propanoic acid 100 mg of (2S)-3-amino-2-{[(tert-butoxy)carbonyl]amino}propanoic acid tert-butylester hydrochloride (Boc-DAP-OtBu.HCl) and 65 mg of N,N'-carbonyl diimidazole (CDI) were dissolved in acetonitrile and stirred at room temperature for 10 minutes. To this, 60 mg of 3-aminobenzenesulfonic acid was added and stirred at 50° C. for 5 hours. The solvent was distilled away, and the resultant was subjected to extraction with ethyl acetate to collect and dry the organic layer. The solvent was distilled away to obtain a crude product of the title compound in protected form. The obtained crude product was added with 5 ml of trifluoroacetic acid and stirred overnight. The solvent was distilled away and the resulting residue was purified by purification step A to obtain the title compound.

Yield: 4.93 mg

Example 78

Synthesis of (2S)-4-[5-chloro-2-hydroxy-3-sulfophenyl)carbamoyl]-2-(methylamino)butanoic acid To 75 mg of 3-[(4S)-4-amino-5-(benzyloxy)-5-oxopentanamide]-5-chloro-2-hydroxybenzene-1-sulfonic acid, 1 ml of methylene chloride, 41 mg of 2-nitrobenzenesulfonyl chloride and 50 µl of triethylamine were added. After agitation for an hour, extraction was performed with ethyl acetate to obtain 100 mg of a crude product. The obtained crude product was added with 23 mg of potassium carbonate, 1 ml of DMF and 10.5 µl of methyl iodide and stirred at room temperature overnight. The resultant was diluted with water and acetonitrile, and subjected to partial purification by purification step A. The resulting crude purified substance was dissolved in 1 ml of THF, 0.5 ml of ethanol and 0.5 ml of water, to which 10 mg of lithium hydroxide was added. While confirming the reaction progress, sodium hydroxide was appropriately added. At the end of the reaction, 2 ml of ethyl acetate was added and stirred. The solvent was distilled away, and the resultant was added with water and lyophilized. The resulting lyophilized product was dissolved in 1 ml of DMF, to which 45 µl of 1-dodecanethiol and 60 µl of an ethanol solution of 28% sodium ethoxide were added and the resultant was stirred for an hour. 45 µl of 1-dodecanethiol and 60 µl of an ethanol solution of 28% sodium ethoxide were further added and stirred. The reaction solution was diluted with water and acetonitrile, and then purified using purification step A to obtain the title compound.

Yield: 2.4 mg

Example 79

Synthesis of (2S)-3-{[(3-chloro-4-methyl-5-sulfophenyl)carbamoyl]amino}-2-(methylamino)propanoic acid 100 mg of Boc-DAP-OtBu hydrochloride and 60 mg of CDI were dissolved in 1 ml of acetonitrile and stirred for 5 minutes. 75 mg of 5-amino-3-chloro-2-methylbenzenesulfonic acid was added and stirred overnight. Extraction was performed with ethyl acetate to obtain a crude product. The obtained crude product was added with 1.5 ml of dioxane and 0.5 ml of dioxane solution containing 4N hydrochloric acid and stirred for 2 hours. The solvent was distilled away to obtain a crude product. To the obtained crude product, 2 ml of methylene chloride was added, and 52 mg of 2-nitrobenzenesulfonyl chloride and 0.14 ml of triethylamine were added. After 2 hours of agitation, extraction was performed with ethyl acetate to obtain a crude product. The obtained crude product was added with 50 mg of potassium carbonate, 2 ml of DMF and 0.1 ml of methyl iodide and stirred at room temperature overnight. Following extraction with ethyl acetate, the solvent was distilled away to obtain a crude product. The obtained crude product was added with 3 ml of trifluoroacetic acid and stirred at room temperature for 5 hours. The solvent was distilled away and the residue was lyophilized. The resulting lyophilized product was added with 1 ml of DMF, further added with 54 µl of 1-dodecanethiol and 80 µl of a 28% sodium ethoxide ethanol solution, and stirred at room temperature. Following dilution with water and acetonitrile, purification was performed using purification step A to obtain the title compound.

Yield: 18.4 mg

Example 80

Synthesis of (2S)-2-amino-3-{[(4-methyl-3-sulfophenyl)carbamoyl]amino}propanoic acid The title compound was obtained through a similar operation except that 3-aminobenzenesulfonic acid used in Example 77 was replaced with 5-amino-2-methylbenzenesulfonic acid.

Yield: 6.86 mg

Example 81

Synthesis of (2S)-2-amino-3-{[(4-methoxy-3-sulfophenyl)carbamoyl]amino}propanoic acid The title compound was obtained through a similar operation except that 3-aminobenzenesulfonic acid used in Example 77 was replaced with 5-amino-2-methoxybenzenesulfonic acid.

Yield: 3.5 mg

Example 82

Synthesis of (2S)-2-amino-3-{[(2-methoxy-5-sulfophenyl)carbamoyl]amino}propanoic acid The title compound was obtained through a similar operation except that 3-aminobenzenesulfonic acid used in Example 77 was replaced with 3-amino-4-methoxybenzenesulfonic acid.

Yield: 6.22 mg

Example 83

Synthesis of (2S)-2-amino-3-{[(3-acetamide-2-hydroxy-5-sulfophenyl)carbamoyl]amino}propanoic acid The title compound was obtained through a similar operation except that 3-aminobenzenesulfonic acid used in Example 77 was replaced with 3-(acetylamino)-5-amino-4-hydroxybenzenesulfonic acid.

Yield: 5.81 mg

Example 84

Synthesis of (2S)-2-amino-3-{[(2-hydroxy-3-nitro-5-sulfophenyl)carbamoyl]amino}propanoic acid The title compound was obtained through a similar operation except that 3-aminobenzenesulfonic acid used in Example 77 was replaced with 3-amino-4-hydroxy-5-nitrobenzenesulfonic acid.
Yield: 6.1 mg

Example 85

Synthesis of 3-({[(2S)-2-amino-2-carboxyethyl]carbamoyl}amino)benzoic acid

The title compound was obtained through a similar operation except that 3-aminobenzenesulfonic acid used in Example 77 was replaced with 3-aminobenzoic acid.
Yield: 2.66 mg

Example 86

Synthesis of 3-({[(2S)-2-amino-2-carboxyethyl]carbamoyl}-amino)-2,5-dichlorobenzoic acid The title compound was obtained through a similar operation except that 3-aminobenzenesulfonic acid used in Example 77 was replaced with 3-amino-2,5-dichlorobenzoic acid.
Yield: 7.56 mg

Example 87

Synthesis of 3-({[(2S)-2-amino-2-carboxyethyl]carbamoyl}amino)-2-methylbenzoic acid The title compound was obtained through a similar operation except that 3-aminobenzenesulfonic acid used in Example 77 was replaced with 3-amino-2-methylbenzoic acid.
Yield: 10.76 mg

Example 88

Synthesis of 3-({[(2S)-2-amino-2-carboxyethyl]carbamoyl}amino)-4-chlorobenzoic acid The title compound was obtained through a similar operation except that 3-aminobenzenesulfonic acid used in Example 77 was replaced with 3-amino-4-chlorobenzoic acid.
Yield: 2.3 mg

Example 89

Synthesis of (2S)-2-amino-3-{[(2,4-dimethyl-5-sulfophenyl)carbamoyl]amino}propanoic acid The title compound was obtained through a similar operation except that 3-aminobenzenesulfonic acid used in Example 77 was replaced with 5-amino-2,4-dimethylbenzoic acid.
Yield: 1 mg

Example 90

Synthesis of 3-({[(2S)-2-amino-2-carboxyethyl]carbamoyl}amino)-2-hydroxybenzoic acid The title compound was obtained through a similar operation except that 3-aminobenzenesulfonic acid used in Example 77 was replaced with 3-aminosalicylic acid.
Yield: 10.5 mg

Example 91

Synthesis of 3-({[(2S)-2-amino-2-carboxyethyl]carbamoyl}amino)-4-methoxybenzoic acid The title compound was obtained through a similar operation except that 3-aminobenzenesulfonic acid used in Example 77 was replaced with 3-amino-4-methoxybenzoic acid.
Yield: 4.72 mg

Example 92

Synthesis of 3-({[(2S)-2-amino-2-carboxyethyl]carbamoyl}amino)-5-nitrobenzoic acid The title compound was obtained through a similar operation except that 3-aminobenzenesulfonic acid used in Example 77 was replaced with 3-amino-5-nitrobenzoic acid.
Yield: 3.5 mg

Example 93

Synthesis of 3-({[(2S)-2-amino-2-carboxyethyl]carbamoyl}amino)-4-methylbenzoic acid The title compound was obtained through a similar operation except that 3-aminobenzenesulfonic acid used in Example 77 was replaced with 3-amino-4-methylbenzoic acid.
Yield: 20.4 mg

Example 94

Synthesis of 3-({[(2S)-2-amino-2-carboxyethyl]carbamoyl}amino)-4-hydroxybenzoic acid The title compound was obtained through a similar operation except that 3-aminobenzenesulfonic acid used in Example 77 was replaced with 3-amino-4-hydroxybenzoic acid.
Yield: 5.6 mg

Example 95

Synthesis of 5-({[(2S)-2-amino-2-carboxyethyl]carbamoyl}amino)-2-chlorobenzoic acid The title compound was obtained through a similar operation except that 3-aminobenzenesulfonic acid used in Example 77 was replaced with 5-amino-2-chlorobenzoic acid.
Yield: 24.4 mg

Example 96

Synthesis of 5-({[(2S)-2-amino-2-carboxyethyl] carbamoyl}amino)-2-hydroxybenzoic acid The title compound was obtained through a similar operation except that 3-aminobenzenesulfonic acid used in Example 77 was replaced with 5-amino-2-hydroxybenzoic acid.

Yield: 2.75 mg

Example 97

Synthesis of 3-({[(2S)-2-amino-2-carboxyethyl] carbamoyl}amino)-4-fluorobenzoic acid The title compound was obtained through a similar operation except that 3-aminobenzenesulfonic acid used in Example 77 was replaced with 3-amino-4-fluorobenzoic acid.

Yield: 31.92 mg

Example 98

Synthesis of 5-({[(2S)-2-amino-2-carboxyethyl] carbamoyl}amino)-2-methoxybenzoic acid The title compound was obtained through a similar operation except that 3-aminobenzenesulfonic acid used in Example 77 was replaced with 5-amino-2-methoxybenzoic acid.

Yield: 9.1 mg

Example 99

Synthesis of 5-({[(2S)-2-amino-2-carboxyethyl] carbamoyl}amino)-2-methylbenzoic acid The title compound was obtained through a similar operation except that 3-aminobenzenesulfonic acid used in Example 77 was replaced with 5-amino-2-methylbenzoic acid.

Yield: 4.3 mg

Example 100

Synthesis of 3-({[(2S)-2-amino-2-carboxyethyl] carbamoyl}amino)-2-methoxybenzoic acid The title compound was obtained through a similar operation except that 3-aminobenzenesulfonic acid used in Example 77 was replaced with 3-amino-2-methoxybenzoic acid.

Yield: 2.35 mg

Example 101

Synthesis of 3-({[(2S)-2-amino-2-carboxyethyl] carbamoyl}amino)-5-methoxybenzoic acid The title compound was obtained through a similar operation except that 3-aminobenzenesulfonic acid used in Example 77 was replaced with 3-amino-5-methoxybenzoic acid.

Yield: 2.42 mg

Example 102

Synthesis of 5-({[(2S)-2-amino-2-carboxyethyl] carbamoyl}amino)-2-fluorobenzoic acid The title compound was obtained through a similar operation except that 3-aminobenzenesulfonic acid used in Example 77 was replaced with 5-amino-2-fluorobenzoic acid.

Yield: 16.73 mg

Example 103

Synthesis of (2S)-2-amino-3-{[(3,4-dimethyl-5-sulfophenyl)carbamoyl]amino}propanoic acid The title compound was obtained through a similar operation except that 3-aminobenzenesulfonic acid used in Example 77 was replaced with 5-amino-2,3-dimethylbenzenesulfonic acid.

Yield: 3.33 mg

Example 104

Synthesis of (2S)-2-amino-3-{[(2-fluoro-5-sulfophenyl)carbamoyl]amino}propanoic acid The title compound was obtained through a similar operation except that 3-aminobenzenesulfonic acid used in Example 77 was replaced with 3-amino-4-fluorobenzenesulfonic acid.

Yield: 2.54 mg

TABLE 1

| Example Number | Structure | 1H-NMR | MS (ESI, m/z) |
|---|---|---|---|
| 1 | 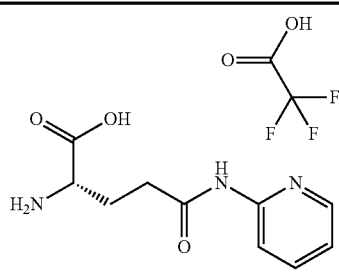 | | 224[M + H]$^+$ |

TABLE 1-continued

| Example Number | Structure | 1H-NMR | MS (ESI, m/z) |
|---|---|---|---|
| 2 | (structure) | 1H-NMR(300 MHz, D₂O) δ: 8.12(d, 1H), 7.3(d, 1H), 3.87(t, 1H), 2.63-2.69(m, 2H), 2.55(s, 3H), 2.10-2.20(m, 2H) | 317[M + H]⁺ |
| 3 | (structure) | | 339[M + H]⁺ |
| 4 | (structure) | 1H-NMR(300 MHz, D₂O) δ: 7.68-7.80(m, 1H), 7.30-7.50(m, 3H), 4.00-4.19(m, 1H), 2.97-3.68(m, 2H) | 321[M + H]⁺ |
| 5 | (structure) | 1H-NMR(300 MHz, D₂O) δ: 10.98(s, 1H), 10.02(s, 1H), 8.30(br, 2H), 7.70(s, 1H), 7.21(s, 1H), 4.05-4.25(m, 1H), 3.00-3.80(m, 2H) | 371[M + H]⁺ |
| 6 | (structure) | 1H-NMR(300 MHz, D₂O) δ: 7.62(d, 1H), 7.34(d, 1H), 4.02(dd, 1H), 3.74(dd, 1H), 3.59(dd, 1H) | 354[M + H]+ 352[M − H]⁻ |
| 7 | (structure) | 1H-NMR(300 MHz, DMSO-d6) δ: 7.83(d, 1H,), 7.12(d, 1H), 4.17-4.22(m, 1H), 4.02-4.06(m, 1H), 1.19(d, 3H) | 323[M − H]⁻ |
| 8 | (structure) | 1H-NMR(300 MHz, DMSO-d6) δ: 7.85(d, 1H), 7.12(d, 1H), 4.34(dd, 1H), 4.11(dd, 1H), 1.90-2.00(m, 1H), 0.95-1.00(m, 6H) | 353[M + H]+ 351[M − H]⁻ |

TABLE 1-continued

| Example Number | Structure | 1H-NMR | MS (ESI, m/z) |
|---|---|---|---|
| 9 | (structure) | 1H-NMR(300 MHz, DMSO-d6) δ: 7.83(d, 1H), 7.29-7.40(m, 5H), 7.12(d, 1H), 4.21(dd, 1H), 3.96(dd, 1H), 3.64-3.73(m, 1H), 2.89-2.94(m, 2H) | 401[M + H]+ 399[M − H]− |

TABLE 2

| Example Number | Structure | 1H-NMR | MS (ESI, m/z) |
|---|---|---|---|
| 10 | (structure) | 1H-NMR(300 MHz, DMSO-d6) δ: 7.80-7.85(m, 1H), 7.46-7.52(m, 5H), 7.13(d, 1H), 4.60-4.80(m, 1H), 4.30-4.44(m, 2H) | 387[M + H]+ 385[M − H]− |
| 11 | (structure) | 1H-NMR(300 MHz, D$_2$O) δ: 7.63(brs, 1H), 7.38(d, 1H), 4.35(dd, 1H), 4.19(dd, 1H), 3.48-3.57(m, 1H), 2.33-2.39(m, 2H), 1.86-1.94(m, 2H) | 382[M + H]+ 380[M − H]− |
| 12 | (structure) | 1H-NMR(300 MHz, D$_2$O) δ: 7.68(brs, 1H), 7.39(dd, 1H), 4.41(dd, 1H) 4.24(dd, 1H), 3.55-3.65(m, 1H), 2.61(t, 2H), 1.90-2.10(m, 2H) | 364[M + H]+ 362[M − H]− |
| 13 | (structure) | 1H-NMR(300 MHz, D$_2$O) δ: 7.62(d, 1H), 7.51(d, 1H), 3.88(dd, 1H), 3.71(dd, 1H), 3.52(dd, 1H), 2.45(s, 3H) | 352[M + H]+ 350[M − H]− |

TABLE 2-continued
| Example Number | Structure | 1H-NMR | MS (ESI, m/z) |
|---|---|---|---|
| 14 | 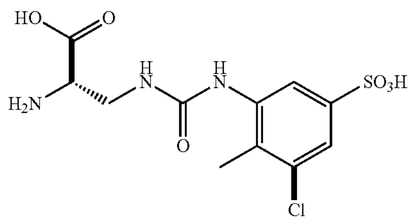 | 1H-NMR(300 MHz, D₂O) δ: 7.60(d, 1H), 7.55(d, 1H), 3.82(dd, 1H), 3.69(d, 1H), 3.51(dd, 1H), 2.20(s, 3H) | 352[M + H]+ 350[M − H]− |
| 15 | 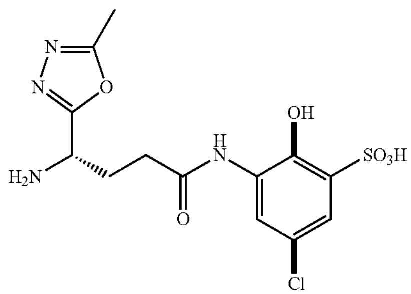 | | 391[M + H]+ |
| 16 | 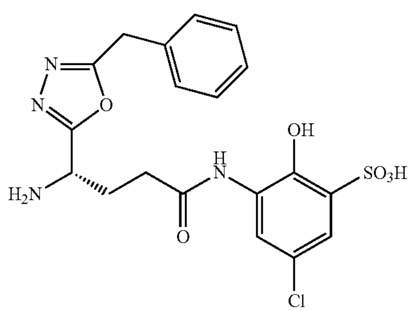 [SMILES: N[C@@H](CCC(=O)Nc1cc(Cl)cc(S(=O)(=O)O)c1O)c1nnc(Cc2ccccc2)o1] | 1H-NMR(300 MHz, D₂O) δ: 7.52(d, 1H), 7.42(d, 1H), 7.17-7.30(m, 5H), 4.60-4.80(m, 1H), 4.14(s, 2H), 2.55-2.60(m, 2H), 2.33-2.40(m, 2H) | 467[M + H]+ 465[M − H]− |
| 17 | 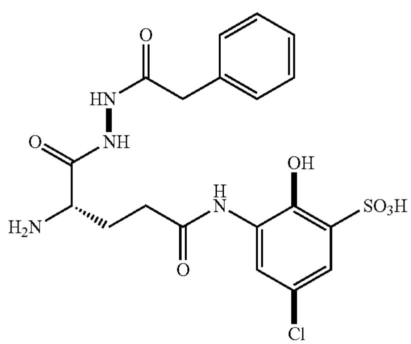 | 1H-NMR(300 MHz, D₂O) δ: 7.66(d, 1H), 7.44(d, 1H), 7.20-7.31(m, 5H), 3.98(t, 1H), 3.58(s, 2H), 2.6(t, 2H), 2.10-2.20(m, 2H) | 485[M + H]+ 483[M − H]− |
TABLE 3
| Example Number | Structure | 1H-NMR | MS (ESI, m/z) |
|---|---|---|---|
| 18 | 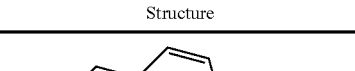 | 1H-NMR(300 MHz, D₂O) δ: 7.66(s, 1H), 7.46-7.55(m, 1H), 7.35-7.40(m, 2H), 7.10-7.30(m, 5H), 4.78-4.83(m, 1H), 4.12(s, 2H), 2.47-2.53(m, 2H), 2.32-2.39(m, 2H) | 417[M + H]+ 415[M − H]− |

TABLE 3-continued

| Example Number | Structure | 1H-NMR | MS (ESI, m/z) |
| --- | --- | --- | --- |
| 19 | (structure: 5-(4-bromophenyl)-1,3,4-oxadiazole linked to CH(NH2)CH2CH2C(O)NH-phenyl with OH, SO3H, Cl substituents) | 1H-NMR(300 MHz, D2O) δ: 7.15-7.62(m, 6H), 4.70-4.80(m, 1H), 2.60-2.73(m, 2H), 2.40-2.52(m, 2H) | 533[M + H]+ |
| 20 | (structure: 5-(4-bromophenyl)-1,3,4-oxadiazole linked to CH(NH2)CH2CH2C(O)NH-phenyl-SO3H) | 1H-NMR(300 MHz, D2O) δ: 7.17-7.60(m, 8H), 4.77-4.90(m, 1H), 2.55(m, 2H), 2.40-2.47(m, 2H) | 481, 483 [M + H]+ |
| 21 | (structure: 5-phenyl-1,3,4-oxadiazole linked to CH(NH2)CH2CH2C(O)NH-phenyl with OH, SO3H, Cl substituents) | 1H-NMR(300 MHz, DMSO-d6) δ: 11.07(brs, 1H), 9.39(s, 1H), 8.01-8.05(m, 2H), 7.96(d, 1H), 7.59-7.69(m, 3H), 7.12(d, 1H), 4.89(t, 1H), 2.60-2.73(m, 2H), 2.27-2.37(m, 2H) | 453, 455[M + H]+ 451, 453[M − H]− |
| 22 | (structure: benzyl-NH-C(O)-CH(NH2)-CH2CH2-C(O)NH-phenyl with OH, SO3H, Cl substituents) | 1H-NMR(300 MHz, DMSO-d6) δ: 11.10(s, 1H), 9.37(s, 1H), 8.91(t, 1H), 8.16(m, 2H), 8.03(m, 1H), 7.23-7.40(m, 6H), 7.15(d, 1H), 4.20-4.50(m, 2H), 3.80-3.85(m, 1H), 2.50-2.60(m, 2H), 2.05(dd, 2H) | 442, 444[M + H]+ 440[M − H]− |

TABLE 3-continued

| Example Number | Structure | 1H-NMR | MS (ESI, m/z) |
|---|---|---|---|
| 23 | 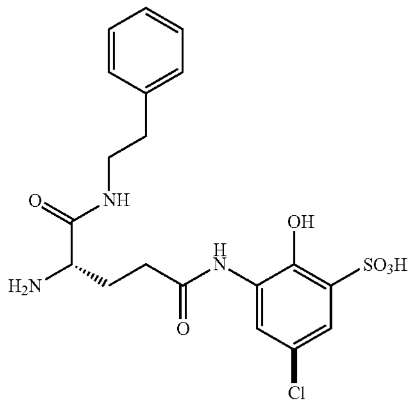 | 1H-NMR(300 MHz, DMSO-d6) δ: 11.11(s, 1H), 10.31(s, 1H), 8.45-8.54(m, 1H), 8.00-8.20(m, 3H), 7.12-7.33(m, 6H), 3.70-3.80(m, 1H), 3.40-3.50(m, 2H), 2.71-2.80(m, 2H), 2.40-2.60(m, 2H), 1.90-2.08(m, 2H) | 456, 458[M + H]+ 454, 456[M − H]− |

TABLE 4

| Example Number | Structure | 1H-NMR | MS (ESI, m/z) |
|---|---|---|---|
| 24 | 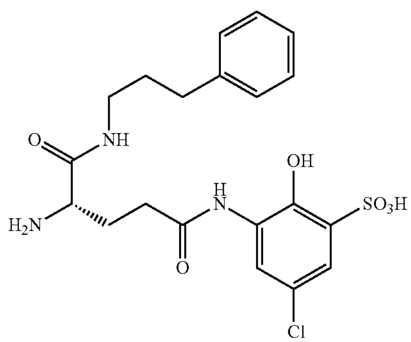 [SMILES: N[C@@H](CCC(=O)Nc1cc(Cl)cc(S(=O)(=O)O)c1O)C(=O)NCCCc1ccccc1] | 1H-NMR(300 MHz, DMSO-d6) δ: 9.38(s, 1H), 8.40(m, 1H), 8.03(m, 1H), 7.10-7.31(m, 7H), 3.68-3.78(m, 1H), 3.10-3.20(m, 2H), 2.40-2.70(m, 4H), 1.85-2.06(m, 2H), 1.70-1.80(m, 2H) | 470, 472[M + H]+ 468, 471[M − H]− |
| 25 | 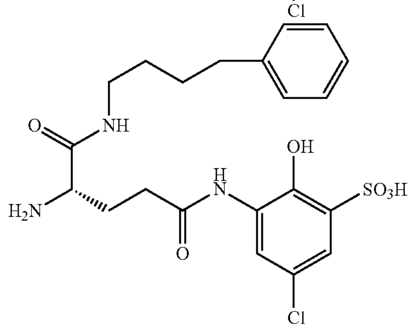 | 1H-NMR(300 MHz, DMSO-d6) δ: 9.36(s, 1H), 8.30-8.40(m, 1H), 8.00-8.05(m, 1H), 7.10-7.30(m, 7H), 3.70(t, 1H), 3.30-3.45(m, 2H), 3.10-3.20(m, 2H), 2.50-2.65(m, 2H), 1.90-2.05(m, 2H), 1.40-1.65(m, 4H) | 484, 486[M + H]+ 482, 484[M − H]− |
| 26 | 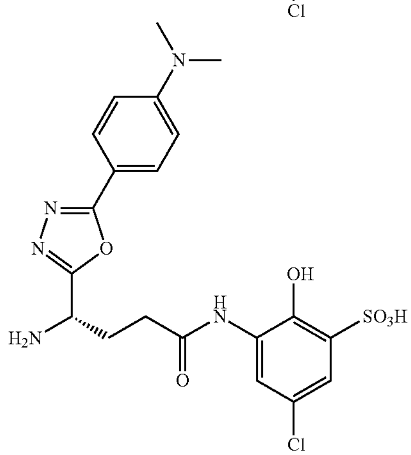 | 1H-NMR(300 MHz, DMSO-d6) δ: 11.07(brs, 1H), 9.41(s, 1H), 8.80(m, 3H), 7.98(d, 1H), 7.79(d, 2H), 7.12(d, 1H), 6.83(d, 2H), 4.87(br, 1H), 3.02(s, 6H), 2.55-2.75(m, 2H), 2.27-2.36(m, 2H) | 496, 498[M + H]+ 494[M − H]− |

TABLE 4-continued

| Example Number | Structure | 1H-NMR | MS (ESI, m/z) |
|---|---|---|---|
| 27 | 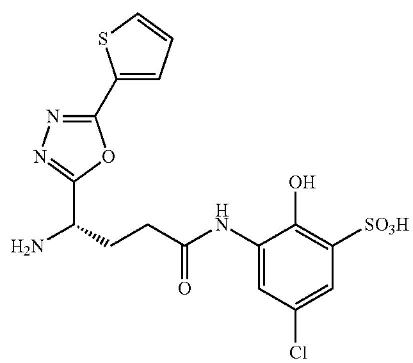 [SMILES: N[C@@H](CCC(=O)Nc1cc(Cl)cc(S(=O)(=O)O)c1O)c1nnc(-c2cccs2)o1] | 1H-NMR(300 MHz, DMSO-d6) δ: 11.07(br, 1H), 9.38(s, 1H), 7.99(m, 2H), 7.83(dd, 1H), 7.31(dd, 1H), 7.12(d, 1H), 4.80(m, 1H), 2.20-2.80(m, 4H) | 459[M + H]+ 457[M − H]− |
| 28 | 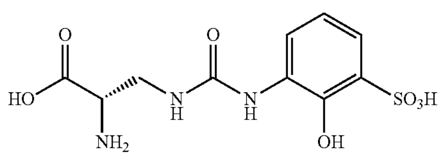 [SMILES: N[C@@H](CNC(=O)Nc1cccc(S(=O)(=O)O)c1O)C(=O)O] | | 318[M − H]− |
| 29 | 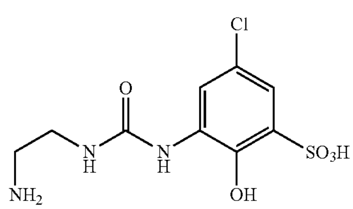 [SMILES: NCCNC(=O)Nc1cc(Cl)cc(S(=O)(=O)O)c1O] | | 308[M − H]− |

TABLE 5

| Example Number | Structure | 1H-NMR | MS (ESI, m/z) |
|---|---|---|---|
| 30 | 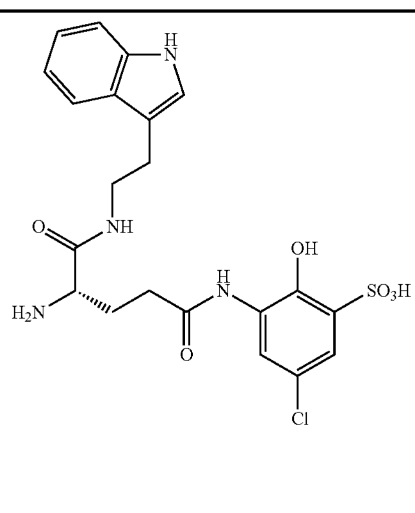 | 1H-NMR(300 MHz, DMSO-d6) δ: 11.09(s, 1H), 10.83(s, 1H), 9.36(s, 1H), 8.53(t, 1H), 8.00-8.30(m, 4H), 6.96-7.60(m, 5H), 3.76-3.79(m, 1H), 3.20-3.50(m, 2H), 2.85-2.92(m, 2H), 2.40-2.60(m, 2H), 1.97-2.07(m, 2H) | 495[M + H]+ |

TABLE 5-continued

| Example Number | Structure | 1H-NMR | MS (ESI, m/z) |
|---|---|---|---|
| 31 | 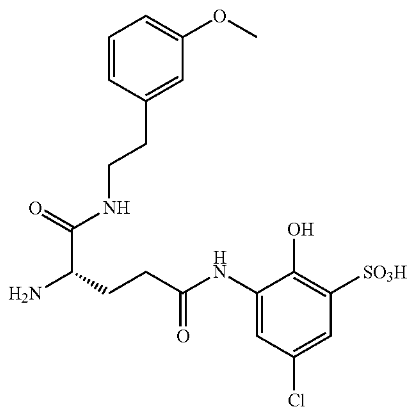 [SMILES: COc1cccc(CCNC(=O)[C@@H](N)CCC(=O)Nc2cc(Cl)cc(S(=O)(=O)O)c2O)c1] | 1H-NMR(300 MHz, DMSO-d6) δ: 9.38(s, 1H), 8.47(t, 1H), 7.90-8.20(m, 3H), 7.14-7.23(m, 2H), 6.70-6.81(m, 2H), 3.70-3.80(m, 3H), 3.40-3.50(m, 2H), 2.74(t, 2H), 2.40-2.55(m, 2H), 1.90-2.01(m, 2H) | 488[M + H]+ |
| 32 | 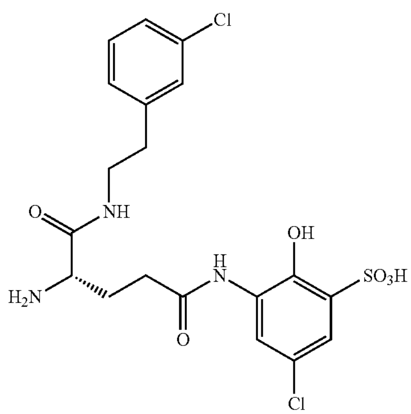 [SMILES: N[C@@H](CCC(=O)Nc1cc(Cl)cc(S(=O)(=O)O)c1O)C(=O)NCCc1cccc(Cl)c1] | | 490, 492[M + H]+ 488[M − H]− |
| 33 | 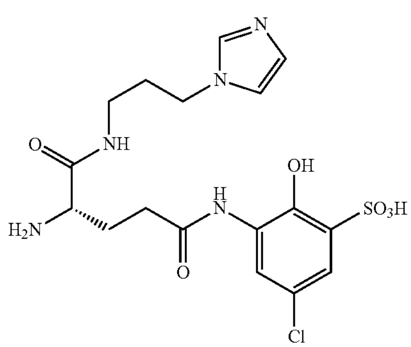 [SMILES: N[C@@H](CCC(=O)Nc1cc(Cl)cc(S(=O)(=O)O)c1O)C(=O)NCCCn1ccnc1] | 1H-NMR(400 MHz, D2O) δ: 8.57(s, 1H), 7.73(d, 1H), 7.41(d, 1H), 7.32-7.37(m, 2H), 4.11(t, 2H), 3.96(dd, 1H), 3.07-3.25(m, 2H), 2.63(t, 2H), 2.15-2.30(m, 2H), 1.89-2.00(m, 2H) | 460, 461[M + H]+ 458[M − H]− |
| 34 | 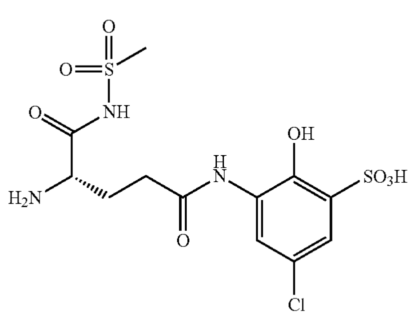 [SMILES: CS(=O)(=O)NC(=O)[C@@H](N)CCC(=O)Nc1cc(Cl)cc(S(=O)(=O)O)c1O] | 1H-NMR(300 MHz, D2O) δ: 7.66(d, 1H), 7.42(d, 1H), 3.8(t, 1H), 2.99(s, 3H), 2.54-2.62(m, 2H), 2.08-2.20(m, 2H) | 430, 432[M + H]+ 428, 430[M − H]− |

TABLE 5-continued

| Example Number | Structure | 1H-NMR | MS (ESI, m/z) |
|---|---|---|---|
| 35 | 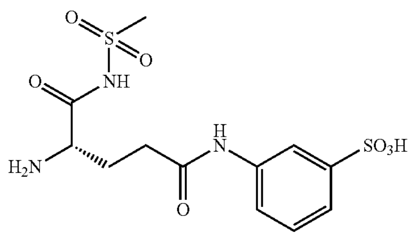 [SMILES: CS(=O)(=O)NC(=O)[C@@H](N)CCC(=O)Nc1cccc(S(=O)(=O)O)c1] | 1H-NMR(300 MHz, D₂O) δ: 7.76-7.77(m, 1H), 7.20-7.51(m, 4H), 3.99(t, 1H), 3.16(s, 3H), 2.54-2.60(m, 2H), 2.16-2.24(m, 2H) | 380[M + H]⁺ |

TABLE 6

| Example Number | Structure | 1H-NMR | MS (ESI, m/z) |
|---|---|---|---|
| 36 | 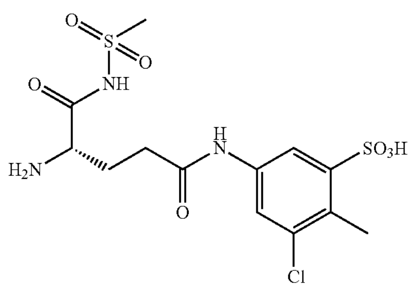 [SMILES: Cc1c(Cl)cc(NC(=O)CC[C@H](N)C(=O)NS(C)(=O)=O)cc1S(=O)(=O)O] | 1H-NMR(300 MHz, D₂O) δ: 7.72(d, 1H), 7.53(d, 1H), 4.01(t, 1H), 3.19(s, 3H), 2.50-2.56(m, 2H), 2.46(s, 3H), 2.14-2.23(m, 2H) | 428[M + H]+ 426[M − H]⁻ |
| 37 | 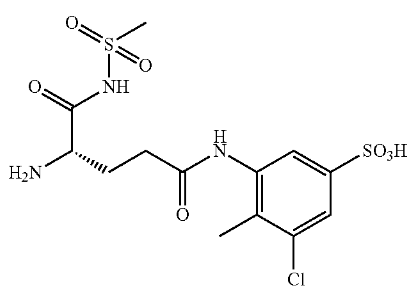 [SMILES: Cc1c(Cl)cc(S(=O)(=O)O)cc1NC(=O)CC[C@H](N)C(=O)NS(C)(=O)=O] | 1H-NMR(300 MHz, D₂O) δ: 7.66(d, 1H), 7.49(d, 1H), 3.99(t, 1H), 3.16(s, 3H), 2.63(t, 2H), 2.15-2.30(m, 5H) | 428[M + H]+ 426[M − H]⁻ |
| 38 | 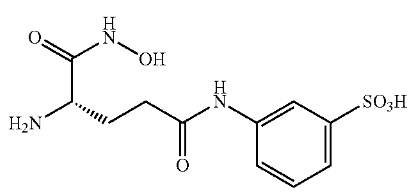 [SMILES: N[C@@H](CCC(=O)Nc1cccc(S(=O)(=O)O)c1)C(=O)NO] | 1H-NMR(400 MHz, D₂O) δ 7.35-7.75(m, 4H), 3.82(t, 1H), 2.38-2.56(m, 2H), 2.05-2.15(m, 2H) | 318[M + H]⁺ |
| 39 | 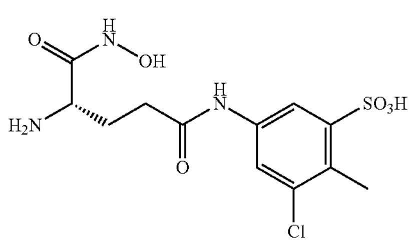 [SMILES: Cc1c(Cl)cc(NC(=O)CC[C@H](N)C(=O)NO)cc1S(=O)(=O)O] | 1H-NMR(400 MHz, D₂O) δ: 7.70(s, 1H), 7.62(s, 1H), 3.70-3.83(m, 1H), 2.35-2.50(m, 5H), 2.02-2.15(m, 2H) | 366[M + H]+ 364[M − H]⁻ |

TABLE 6-continued

| Example Number | Structure | 1H-NMR | MS (ESI, m/z) |
|---|---|---|---|
| 40 | (structure) | 1H-NMR(400 MHz, D₂O) δ: 7.64(d, 1H), 7.45(d, 1H), 3.74(t, 1H), 2.45-2.55(m, 2H), 2.14(s, 3H), 2.04-2.10(m, 2H) | 366[M + H]⁺ |
| 41 | (structure) | 1H-NMR(400 MHz, D₂O) δ: 7.65(d, 1H), 7.42(d, 1H), 3.75-3.83(m, 1H), 2.40-2.60(m, 2H), 2.04-2.14(m, 2H) | 368[M + H]+ <br> 366[M − H]⁻ |
| 42 | (structure) | | 303[M + H]⁺ |

TABLE 7

| Example Number | Structure | 1H-NMR | MS (ESI, m/z) |
|---|---|---|---|
| 43 | (structure) | 1H-NMR(300 MHz, DMSO-d6): δ 7.58-7.12(m, 4H), 4.20-4.03(m, 2H), 1.08 (m, 3H) | 319[M + H]⁺ |
| 44 | (structure) | 1H-NMR(300 MHz, DMSO-d6): δ 8.08 (s, 1H), 6.97(s, 1H), 4.22-4.06(m, 2H), 1.08(m, 3H) | 369, 371[M + H]⁺ |
| 45 | (structure) | 1H-NMR(400 MHz, DMSO-d6): δ 8.08 (s, 1H), 6.97(s, 1H), 4.22-4.06(m, 2H), 1.08(m, 3H) | 369, 371[M + H]⁺ |

TABLE 7-continued

| Example Number | Structure | 1H-NMR | MS (ESI, m/z) |
|---|---|---|---|
| 46 | 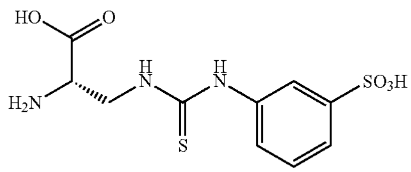 [SMILES: N[C@@H](CNC(=S)Nc1cccc(S(=O)(=O)O)c1)C(=O)O] | 1H-NMR(300 MHz, D₂O): δ 7.65-7.41(m, 4H), 4.21-4.16(m, 2H), 4.01-3.95(m, 1H) | 320[M + H]⁺ |
| 47 | 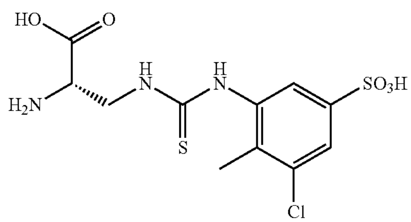 [SMILES: Cc1c(Cl)cc(S(=O)(=O)O)cc1NC(=S)NC[C@H](N)C(=O)O] | 1H-NMR(400 MHz, DMSO-d6): δ 9.62(s, 1H), 8.24(s, 3H), 7.67(s, 1H), 7.49(s, 1H), 7.38(s, 1H), 4.21-4.03(m, 1H), 4.03-4.00(m, 1H), 3.86-3.79(m, 1H), 2.18(s, 3H) | 368, 370[M + H]⁺ |
| 48 | 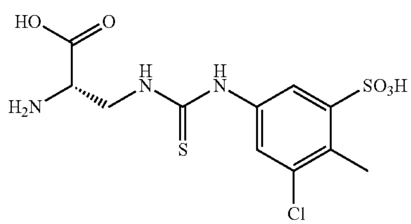 [SMILES: Cc1c(Cl)cc(NC(=S)NC[C@H](N)C(=O)O)cc1S(=O)(=O)O] | 1H-NMR(400 MHz, DMSO-d6): δ 9.98(s, 1H), 8.26(s, 3H), 7.81(s, 1H), 7.77(s, 1H), 7.62(s, 1H), 4.22-4.15(m, 1H), 4.10-4.07(m, 1H), 3.84-3.78(m, 1H), 2.53(s, 3H) | 368, 370[M + H]⁺ |
| 49 | 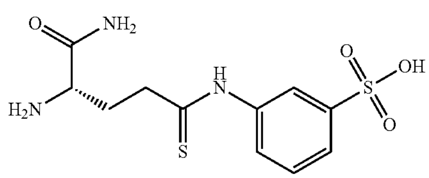 [SMILES: NC(=O)[C@@H](N)CCC(=S)Nc1cccc(S(=O)(=O)O)c1] | | 302[M + H]⁺ |

TABLE 8

| Example Number | Structure | 1H-NMR | MS (ESI, m/z) |
|---|---|---|---|
| 50 | 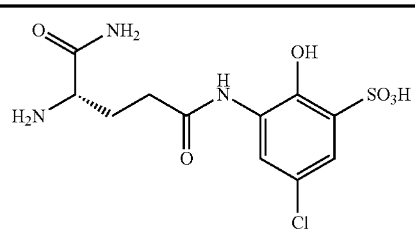 | 1H-NMR(400 MHz, DMSO-d6): δ 11.1(s, 1H), 9.41(s, 1H), 8.05(s, 3H), 8.01(s, 1H) 7.85(s, 1H), 7.62(s, 1H), 7.15(s, 1H), 3.77-3.75(m, 1H), 2.55-2.53(m, 2H), 2.06-1.99(m, 2H) | 352, 354[M + H]⁺ |
| 51 | 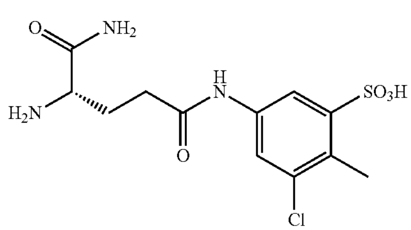 [SMILES: Cc1c(Cl)cc(NC(=O)CC[C@H](N)C(N)=O)cc1S(=O)(=O)O] | 1H-NMR(400 MHz, DMSO-d6): δ 10.19 (s, 1H), 8.08(s, 3H), 7.94(s, 1H), 7.87 (s, 1H) 7.80(s, 1H), 7.64(s, 1H), 3.79-3.76(m, 1H), 2.50(s, 3H), 2.46-2.40(m, 2H), 2.06-1.99(m, 2H) | 350, 352[M + H]⁺ |

TABLE 8-continued

| Example Number | Structure | 1H-NMR | MS (ESI, m/z) |
|---|---|---|---|
| 52 | 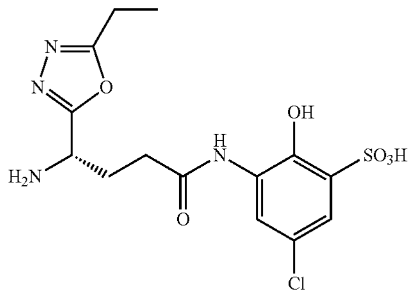 [SMILES: CCc1nnc([C@@H](N)CCC(=O)Nc2cc(Cl)cc(S(=O)(=O)O)c2O)o1] | 1H-NMR(400 MHz, DMSO-d6): δ 11.6(s, 1H), 11.2(s, 1H), 10.6(s, 1H), 10.5(s, 1H) 9.93(s, 1H), 8.01(s, 1H), 7.20(s, 1H), 4.97-4.94(m, 1H), 3.02-2.99(m, 2H), 2.58-2.50(m, 2H), 2.25-2.20(m, 2H), 1.07-1.04(m, 3H) | 405, 407[M + H]+ |
| 53 | 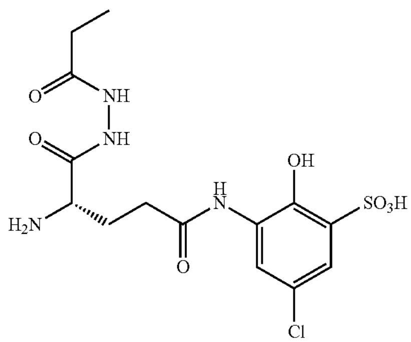 [SMILES: CCC(=O)NNC(=O)[C@@H](N)CCC(=O)Nc1cc(Cl)cc(S(=O)(=O)O)c1O] | 1H-NMR(400 MHz, DMSO-d6): δ 11.2(s, 1H), 10.1(s, 1H), 9.83(s, 1H), 9.71(s, 1H) 8.25(s, 3H), 8.00(s, 1H), 7.22(s, 1H), 4.25-4.21(m, 1H), 2.32-2.28(m, 2H), 2.15-2.03(m, 4H), 1.03-0.99(m, 3H) | 423, 425[M + H]+ |
| 54 | 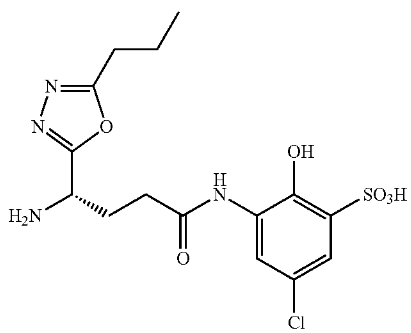 [SMILES: CCCc1nnc([C@@H](N)CCC(=O)Nc2cc(Cl)cc(S(=O)(=O)O)c2O)o1] | | 419[M + H]+ |
| 55 | 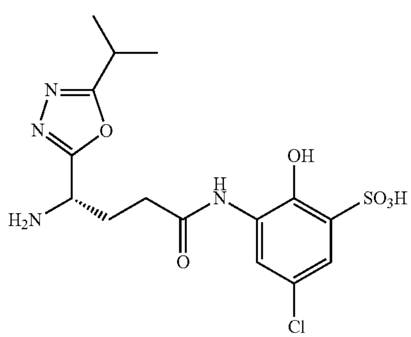 [SMILES: CC(C)c1nnc([C@@H](N)CCC(=O)Nc2cc(Cl)cc(S(=O)(=O)O)c2O)o1] | | 419[M + H]+ |
| 56 | 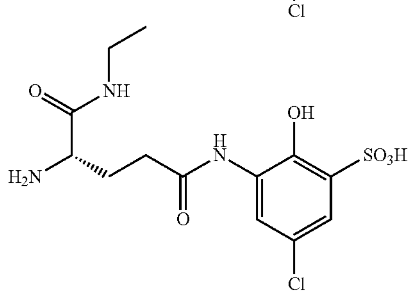 | 1H-NMR(300 MHz, D2O): δ 7.69(s, 1H), 7.44(s, 1H), 3.91-3.84(m, 1H), 3.15-3.08(m, 2H), 2.56-2.52(m, 2H), 2.15-2.09(m, 2H), 1.01-0.96(m, 3H) | 380, 382[M + H]+ |

TABLE 9

| Example Number | Structure | 1H-NMR | MS (ESI, m/z) |
|---|---|---|---|
| 57 | 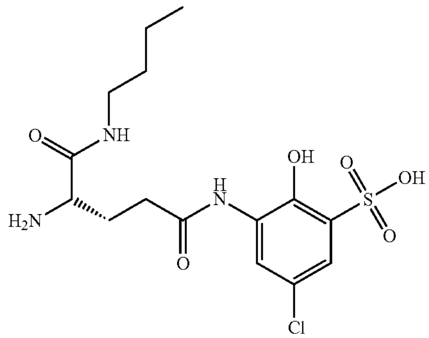 | 1H-NMR(300 MHz, D$_2$O): δ 7.72(s, 1H), 7.43(s, 1H), 3.91-3.84(m, 1H), 3.12-3.03(m, 2H), 2.58-2.52(m, 2H), 2.15-2.09(m, 2H), 1.37-1.26(m, 2H), 1.25-1.09(m, 2H), 0.74-0.68(m, 3H) | 408, 410[M + H]$^+$ |
| 58 | 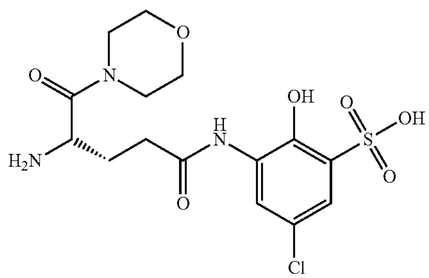 | 1H-NMR(300 MHz, D$_2$O): δ 7.66(s, 1H), 7.43(s, 1H), 4.53-4.47(m, 1H), 3.66-3.49(m, 8H), 2.61-2.57(m, 2H), 2.15-2.11(m, 2H) | 422, 424[M + H]$^+$ |
| 59 | 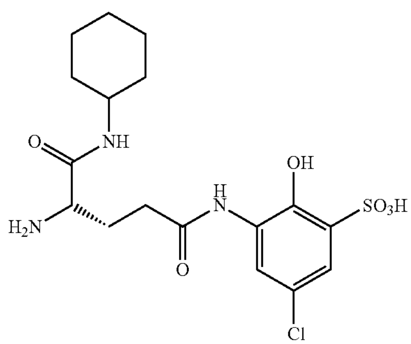 | 1H-NMR(400 MHz, DMSO-d6): δ 11.01 (s, 1H), 9.39(s, 1H), 8.29(s, 1H), 8.08 (s, 3H), 8.01(s, 1H), 7.14(s, 1H), 3.73-3.70(m, 1H), 3.59-3.53(m, 2H), 2.03-1.96(m, 2H), 1.81-1.69(m, 5H), 1.29-1.16(m, 6H) | 434, 436[M + H]$^+$ |
| 60 | 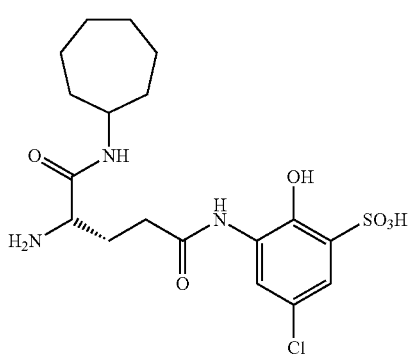 | 1H-NMR(300 MHz, CD$_3$OD): δ 8.08(s, 1H), 7.26(s, 1H), 3.77-3.76(m, 1H), 3.70-3.67(m, 1H), 2.54-2.53(m, 2H), 2.07-2.02(m, 2H), 1.59-1.38(m, 12H) | 448, 450[M + H]$^+$ |

TABLE 9-continued

| Example Number | Structure | 1H-NMR | MS (ESI, m/z) |
|---|---|---|---|
| 61 | 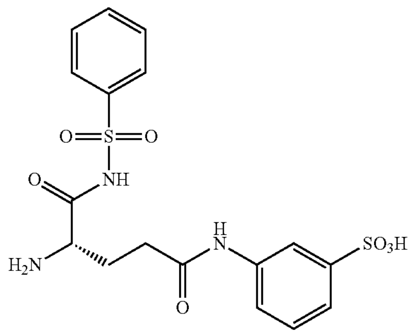 [SMILES: N[C@@H](CCC(=O)Nc1cccc(S(=O)(=O)O)c1)C(=O)NS(=O)(=O)c1ccccc1] | 1H-NMR(300 MHz, DMSO-d6): δ 8.18-7.21(m, 9H), 3.89-3.81(m, 1H), 2.41-2.33(m, 2H), 2.04-1.96(m, 2H) | 442[M + H]+ |
| 62 | 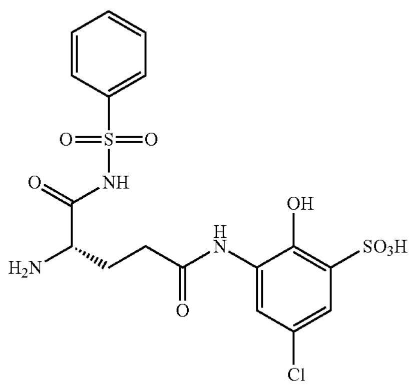 | 1H-NMR(300 MHz, CD3OD): δ 8.18-7.37 (m, 7H), 3.95-3.87(m, 1H), 2.61-2.48 (m, 2H), 2.20-2.08(m, 2H) | 492, 494[M + H]+ |

TABLE 10

| Example Number | Structure | 1H-NMR | MS (ESI, m/z) |
|---|---|---|---|
| 63 | 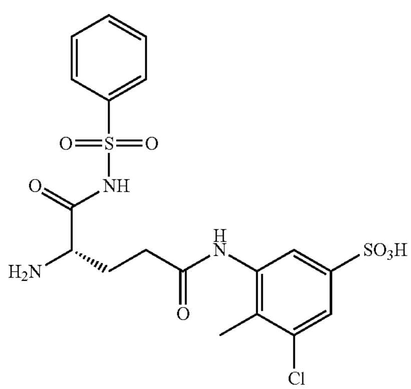 [SMILES: Cc1c(Cl)cc(S(=O)(=O)O)cc1NC(=O)CC[C@H](N)C(=O)NS(=O)(=O)c1ccccc1] | 1H-NMR(300 MHz, DMSO-d6): δ 8.18-7.39(m, 7H), 3.89-3.81(m, 1H), 2.41-2.36(m, 2H), 2.16(s, 3H), 2.04-1.96(m, 2H) | 490, 492[M + H]+ |
| 64 | 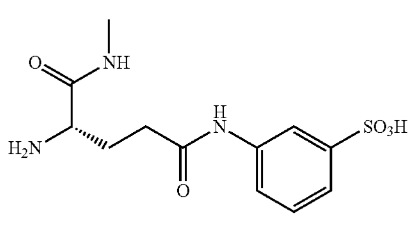 [SMILES: CNC(=O)[C@@H](N)CCC(=O)Nc1cccc(S(=O)(=O)O)c1] | 1H-NMR(300 MHz, CD3OD): δ 8.04(s, 1H), 7.67-7.33(m, 3H), 3.95-3.91(m, 1H), 2.81(s, 3H), 2.59-2.49(m, 2H), 2.19-2.13(m, 2H) | 316[M + H]+ |

TABLE 10-continued

| Example Number | Structure | 1H-NMR | MS (ESI, m/z) |
|---|---|---|---|
| 65 | (structure) | 1H-NMR(300 MHz, CD₃OD): δ 7.74(s, 1H), 7.70(s, 1H), 3.95-3.91(m, 1H), 2.82(s, 3H), 2.65-2.59(m, 2H), 2.28(s, 3H), 2.21-2.15(m, 2H) | 364, 366[M + H]⁺ |
| 66 | (structure) | 1H-NMR(400 MHz, D₂O) δ: 7.66(m, 1H), 7.35-7.48(m, 3H), 4.24(t, 1H), 3.79(s, 3H), 3.70-3.74(m, 2H) | 318[M + H]+ 316[M − H]⁻ |
| 67 | (structure) | 1H-NMR(400 MHz, D₂O) δ: 7.63-7.66(m, 1H), 7.38-7.41(m, 1H), 4.20-4.29(m, 1H), 3.50-3.82(m, 5H) | 368, 370[M + H]+ 366[M − H]⁻ |
| 68 | (structure) | 1H-NMR(400 MHz, D₂O) δ: 7.66(d, 1H), 7.53(d, 1H), 4.25(t, 1H), 3.80(s, 3H), 3.66-3.79(m, 2H), 2.52(s, 3H) | 366, 368[M + H]⁺ |
| 69 | (structure) | 1H-NMR(400 MHz, D₂O) δ: 7.67(d, 1H), 7.57(d, 1H), 4.25(t, 1H), 3.80(s, 3H), 3.72(d*2, 2H), 2.24(s, 3H) | 366, 368[M + H]⁺ |
| 70 | (structure) | 1H-NMR(400 MHz, DMSO-d6): δ 9.73(s, 1H), 8.50-8.46(m, 1H), 8.30(s, 3H), 7.78(s, 1H), 7.41-7.39(m, 1H), 7.27-7.21(m, 2H), 4.45-4.29(m, 2H), 4.06(m, 1H), 2.69(s, 3H) | 318[M + H]⁺ |

TABLE 11

| Example Number | Structure | 1H-NMR | MS (ESI, m/z) |
|---|---|---|---|
| 71 | 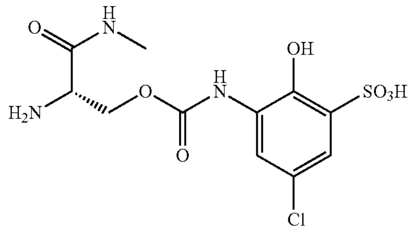 [SMILES: CNC(=O)[C@@H](N)COC(=O)Nc1cc(Cl)cc(S(=O)(=O)O)c1O] | 1H-NMR(400 MHz, DMSO-d6): δ 8.53(s, 1H), 8.43(s, 1H), 8.28(8, 3H), 7.81(s, 1H), 7.13(s, 1H), 4.43-4.34(m, 2H), 4.13 (m, 1H), 2.69(s, 3H) | 368, 370[M + H]$^+$ |
| 72 | 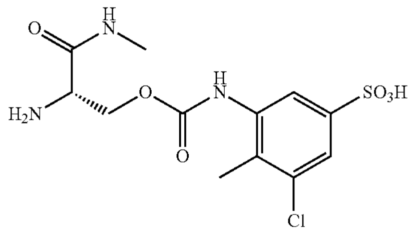 [SMILES: CNC(=O)[C@@H](N)COC(=O)Nc1cc(S(=O)(=O)O)cc(Cl)c1C] | | 368[M + H]$^+$ |
| 73 | 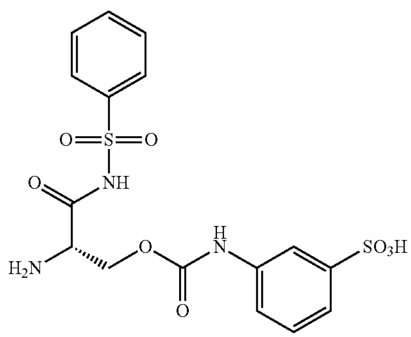 [SMILES: N[C@@H](COC(=O)Nc1cccc(S(=O)(=O)O)c1)C(=O)NS(=O)(=O)c1ccccc1] | 1H-NMR(300 MHz, DMSO-d6): δ 10.5(s, 1H), 8.38(s, 3H), 7.88-7.86(m, 3H), 7.69-7.49(m, 5H), 7.34-7.29(m, 2H), 4.44-4.43 (m, 2H), 4.22(m, 1H) | 444[M + H]$^+$ |
| 74 | 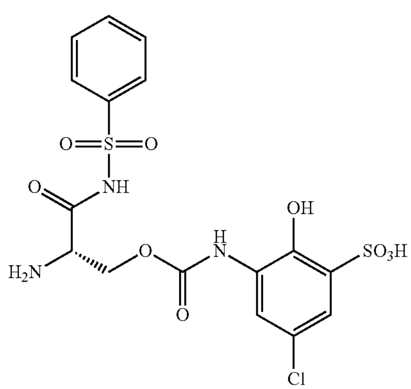 [SMILES: N[C@@H](COC(=O)Nc1cc(Cl)cc(S(=O)(=O)O)c1O)C(=O)NS(=O)(=O)c1ccccc1] | 1H-NMR(300 MHz, DMSO-d6): δ 11.1(s, 1H), 10.1(s, 1H), 8.34(s, 3H), 7.93-7.89 (m, 3H), 7.69-7.59(m, 3H), 7.21(s, 1H), 4.44-4.40(m, 3H) | 494, 496[M + H]$^+$ |
| 75 | 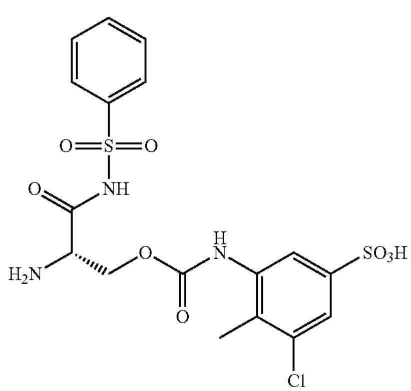 [SMILES: Cc1c(Cl)cc(S(=O)(=O)O)cc1NC(=O)OC[C@H](N)C(=O)NS(=O)(=O)c1ccccc1] | 1H-NMR(300 MHz, DMSO-d6): δ 10.1(s, 1H), 8.37(s, 3H), 7.91-7.88(m, 2H), 7.71-7.55(m, 4H), 7.46(s, 1H), 7.21(s, 1H), 4.46-4.45(m, 2H), 4.33-4.32(m, 1H), 2.13 (s, 3H) | 492, 494[M + H]$^+$ |

TABLE 11-continued

| Example Number | Structure | 1H-NMR | MS (ESI, m/z) |
|---|---|---|---|
| 76 | (structure) | 1H-NMR(300 MHz, DMSO-d6): δ 10.1(s, 1H), 9.41(s, 1H), 7.96(s, 1H), 7.07(s, 1H), 4.01-3.98(m, 1H), 2.78(s, 6H), 2.60-2.58(m, 2H), 2.23-2.02(m, 2H) | 381, 383[M + H]+ |

TABLE 12

| Example Number | Structure | 1H-NMR | MS (ESI, m/z) |
|---|---|---|---|
| 77 | (structure) | 1H NMR(D2O, 400 MHz): δ: 7.71-7.64 (m, 1H), 7.48-7.38 (m, 3H), 3.96 (dd, J = 6.3, 3.7 Hz, 1H), 3.77 (dd, J = 15.2, 3.8 Hz, 1H), 3.60 (dd, J = 15.2, 6.3 Hz, 1H) | 304[M + H+] |
| 78 | (structure) | 1H NMR(D2O, 400 MHz): δ: 7.71 (d, J = 2.6 Hz, 1H), 7.50 (d, J = 2.6 Hz, 1H), 3.79-3.70 (m, 1H), 2.70 (s, 3H), 2.64 (t, J = 7.4 Hz, 2H), 2.34-2.09 (m, 2H) | 367[M + H+] |
| 79 | (structure) | 1H NMR(D2O, 400 MHz): δ: 7.67 (d, J = 2.3 Hz, 1H), 7.56 (d, J = 2.3 Hz, 1H), 3.83 (dd, J = 15.3, 3.5 Hz, 1H), 3.72 (dd, J = 5.2, 3.5 Hz, 1H), 3.57 (dd, J = 15.3, 5.3 Hz, 1H), 2.72 (s, 3H), 2.51 (s, 3H) | 366[M + H+] |
| 80 | (structure) | 1H NMR (400 MHz, D2O) δ 7.69 (d, J = 2.33 Hz, 1H), 7.31 (dd, J = 2.32, 8.18 Hz, 1H), 7.25 (d, J = 8.27 Hz, 1H), 3.95 (dd, J = 3.7, 6.4 Hz, 1H), 3.76 (dd, J = 3.8, 15.2 Hz, 1H), 3.58 (dd, J = 6.4, 15.2 Hz, 1H), 2.47 (s, 3H). | 318[M + H+] |
| 81 | (structure) | 1H NMR (400 MHz, D2O) δ 7.60 (d, J = 2.7 Hz, 1H), 7.38 (dd, J = 2.7, 8.9 Hz, 1H), 7.07 (d, J = 8.9 Hz, 1H), 3.90 (dd, J = 3.6, 6.5 Hz, 1H), 3.83 (s, 3H), 3.77 3.66 (m, 1H), 3.60 3.44 (m, 1H). | 334[M + H+] |

TABLE 12-continued

| Example Number | Structure | 1H-NMR | MS (ESI, m/z) |
|---|---|---|---|
| 82 | (structure) | 1H NMR (400 MHz, D2O) δ 7.99 (d, J = 2.3 Hz, 1H), 7.49 (dd, J = 8.6, 2.3 Hz, 1H), 7.07 (d, J = 8.7 Hz, 1H), 3.88-3.83 (m, 4H), 3.77 (dd, J = 15.2, 3.5 Hz, 1H), 3.56 (dd, J = 15.3, 6.3 Hz, 1H). | 334[M + H$^+$] |
| 83 | (structure) | | 377[M + H$^+$] |

TABLE 13

| Example Number | Structure | 1H-NMR | MS (ESI, m/z) |
|---|---|---|---|
| 84 | (structure) | | 365[M + H$^+$] |
| 85 | (structure) | | 268[M + H$^+$] |
| 86 | (structure) | | 337[M + H$^+$] |
| 87 | (structure) | 1H NMR(DMSO, 400 MHz): δ: 8.14 (s, 1H), 7.83 (d, J = 8.1 Hz, 1H), 7.39 (dd, J = 7.7, 1.1 Hz, 1H), 7.19 (t, J = 7.9 Hz, 1H), 6.91-6.82 (m, 1H), 3.85-3.78 (m, 1H), 3.67-3.58 (m, 2H), 2.34 (s, 3H) | 282[M + H$^+$] |

TABLE 13-continued

| Example Number | Structure | 1H-NMR | MS (ESI, m/z) |
|---|---|---|---|
| 88 | 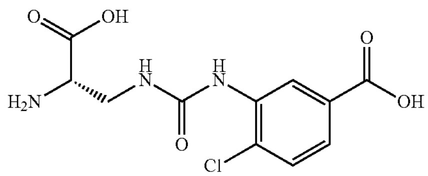 [SMILES: N[C@@H](CNC(=O)Nc1cc(C(=O)O)ccc1Cl)C(=O)O] | | 302[M + H$^+$] |
| 89 | 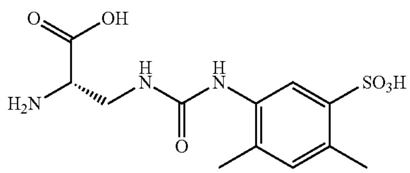 [SMILES: Cc1cc(C)c(S(=O)(=O)O)cc1NC(=O)NC[C@H](N)C(=O)O] | | 332[M + H$^+$] |
| 90 | 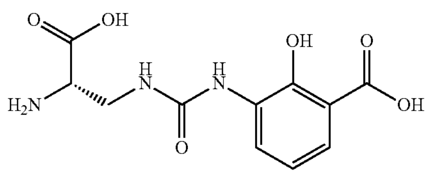 [SMILES: N[C@@H](CNC(=O)Nc1cccc(C(=O)O)c1O)C(=O)O] | 1H NMR(DMSO, 400 MHz): δ: 8.28-8.16 (m, 1H), 7.35 (dd, J = 7.9, 1.2 Hz, 1H), 7.31 (d, J = 5.9 Hz, 1H), 6.76 (t, J = 8.0 Hz, 1H), 4.01 (t, J = 4.9 Hz, 1H), 3.75-3.63 (m, 1H), 3.54-3.38 (m, 1H) | 284[M + H$^+$] |

TABLE 14

| Example Number | Structure | 1H-NMR | MS (ESI, m/z) |
|---|---|---|---|
| 91 | 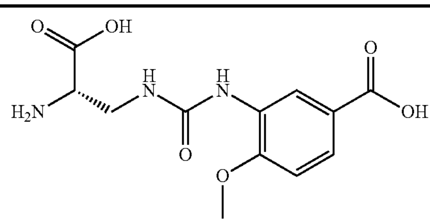 | 1H NMR(DMSO, 400 MHz): δ (ppm) 8.72 (s, 1H), 8.27 (s, 1H), 7.54 (d, J = 8.5 Hz, 1H), 7.25-7.17 (m, 1H), 7.06 (d, J = 8.6 Hz, 1H), 3.90 (s, 3H), 3.85-3.50 (m, 3H) | |
| 92 | 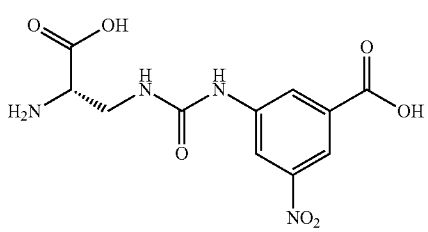 [SMILES: N[C@@H](CNC(=O)Nc1cc(C(=O)O)cc([N+](=O)[O-])c1)C(=O)O] | | 313[M + H$^+$] |
| 93 | 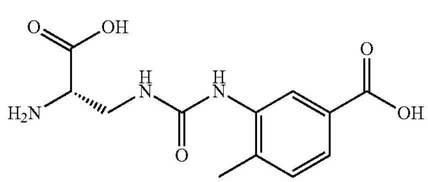 [SMILES: Cc1ccc(C(=O)O)cc1NC(=O)NC[C@H](N)C(=O)O] | 1H NMR (400 MHz, DMSO) δ 2.24 (s, 3H), 3.65-3.40 (m, 3H), 6.91 (s, 1H), 7.24 (d, J = 8.3 Hz, 1H), 7.47 (d, J = 7.9 Hz, 1H), 8.12 (s, 1H), 8.46 (s, 1H). | 282[M + H$^+$] |
| 94 | 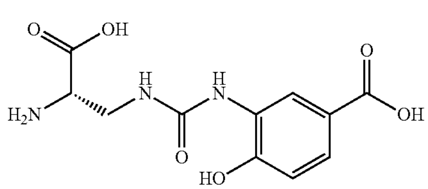 [SMILES: N[C@@H](CNC(=O)Nc1cc(C(=O)O)ccc1O)C(=O)O] | 1H NMR (400 MHz, DMSO) δ 8.61 (s, 1H), 8.23 (s, 1H), 7.41 (d, J = 8.3 Hz, 1H), 7.31-7.09 (m, 1H), 6.85 (d, J = 8.2 Hz, 1H), 3.80-3.72 (m, 1H), 3.68-3.55 (m, 1H), 3.49-3.32 (m, 1H). | |

TABLE 14-continued

| Example Number | Structure | 1H-NMR | MS (ESI, m/z) |
|---|---|---|---|
| 95 | (structure) | 1H NMR (400 MHz, DMSO) δ 3.62-3.45 (m, 2H), 3.77-3.67 (m, 1H), 6.83 (s, 1H), 7.37 (d, J = 8.8 Hz, 1H), 7.53 (dd, J = 8.8, 2.7 Hz, 1H), 7.95 (d, J = 2.7 Hz, 1H), 9.47 (s, 1H). | 302[M + H⁺] |
| 96 | (structure) | 1H NMR (400 MHz, DMSO) δ: 3.44 (m, 2H), 3.82-3.70 (m, 1H), 6.45-6.20 (m, 1H), 6.73 (d, J = 8.8 Hz, 1H), 7.37 (d, J = 8.6 Hz, 1H), 7.80 (s, 1H), 8.61 (br, 1H). | 284[M + H⁺] |
| 97 | (structure) | 1H NMR (400 MHz, DMSO) δ 3.61-3.41 (m, 2H), 3.77 (m, 1H), 6.63-6.34 (m, 1H), 7.01 (d, J = 9.0 Hz, 1H), 7.47 (dd, J = 9.0, 2.7 Hz, 1H), 7.75 (d, J = 2.7 Hz, 1H), 8.97-8.77 (m, 1H). | |

TABLE 15

| Example Number | Structure | 1H-NMR | MS (ESI, m/z) |
|---|---|---|---|
| 98 | (structure) | 1H NMR (400 MHz, DMSO) δ 3.63-3.39 (m, 2H), 3.75(s, 3H), 4.02-3.72 (m, 1H), 6.47 (s, 1H), 7.01 (d, J = 9.0 Hz, 1H), 7.47 (dd, J = 9.0, 2.7 Hz, 1H), 7.75 (d, J = 2.7 Hz, 1H), 8.86 (s, 1H). | 298[M + H⁺] |
| 99 | (structure) | 1H NMR (400 MHz, DMSO) δ: 2.42 (s, 3H), 3.55-3.40 (m, 2H), 3.72-3.57 (m, 1H), 6.53 (s, 1H), 7.14 (d, J = 8.4 Hz, 1H), 7.46 (dd, J = 8.3, 2.2 Hz, 1H), 7.93 (d, J = 2.2 Hz, 1H), 9.03 (s, 1H). | 282[M + H⁺] |
| 100 | (structure) | | 298[M + H⁺] |
| 101 | (structure) | 1H NMR (400 MHz, DMSO) δ 3.62-3.41 (m, 4H), 3.75 (s, 3H), 6.74-6.50 (m, 1H), 7.01 (s, 1H), 7.36 (s, 1H), 7.58 (s, 1H), 9.32-9.13 (m, 1H). | 298[M + H⁺] |

TABLE 15-continued

| Example Number | Structure | 1H-NMR | MS (ESI, m/z) |
|---|---|---|---|
| 102 | (structure) | 1H NMR (400 MHz, DMSO) δ 3.65-3.48 (m, 2H), 3.79 (m, 1H), 6.60-6.45 (m, 1H), 7.21-7.15 (m, 1H), 7.62-7.54 (m, 1H), 7.98 (dd, J = 6.5, 2.9 Hz, 1H), 9.11 (s, 1H). | 286[M + H$^+$] |
| 103 | (structure) | 1H NMR (400 MHz, DMSO) δ 2.12(s, 3H), 2.41(s, 3H), 3.68-3.44 (m, 2H), 3.95-3.77 (m, 1H), 6.61 (br, 1H), 6.89 (s, 1H), 7.88 (s, 1H), 7.96 (s, 1H). | 332[M + H$^+$] |
| 104 | (structure) | 1H NMR (400 MHz, DMSO) δ 3.69-3.45 (m, 2H), 3.90-3.80 (m, 1H), 6.96-6.81 (m, 1H), 7.15-7.03 (m, 1H), 7,22-7.14 (m, 1H), 8.41 (dd, J = 7.9, 2.1 Hz, 1H), 8.55 (s, 1H). | 322[M + H$^+$] |

Test Example I

Assessment of CaSR Agonistic Activity (Preparation of CaSR Gene)

CaSR gene was prepared according to the method described in Example 1 of WO07/55393. The resulting recombinant plasmid was used to generate human CaSR-expressing plasmid hCaSR/pcDNA3.1.

(Method for Assessing CaSR Agonist)

293E cells (EBNA1-expressing HEK293 cells, ATCC No. CRL-10852) were cultured in DMEM (1.0 g/ml Glucose-containing Dulbecco's modified Eagle medium, Nacalai Tesque) containing 10% bovine fetal serum in the presence of 250 μg/ml of G418. The cells were seeded on a 10 cm-diameter petri dish at 1.8×10$^6$ cells/15 ml, and left to stand in a $CO_2$ incubator (5% $CO_2$, 37° C.) for 24 hours. Thereafter, human CaSR expression plasmid hCaSR/pcDNA3.1 was transfected with transfection reagent Mirus Trans IT 293 (Takara Bio). Following static culture in a $CO_2$ incubator for 24 hours, the cells were harvested with 10% bovine fetal serum-containing DMEM and seeded on a poly-D-lysine coat 384 well plate (Falcon) at 15,000 cells/well. Following static culture in a $CO_2$ incubator for 24 hours, the medium was removed and the resultant was added with 50 μl/well of $Ca^{2+}$ fluorescent indicator Calcium 4 Assay Kit (Molecular Devices) dissolved in an assay buffer (146 mM NaCl, 5 mM KCl, 1 mM $MgSO_4$, 1 mg/ml Glucose, 20 mM HEPES (PH 7.2), 1.5 mM $CaCl_2$), and left to stand at 37° C. for an hour and then at room temperature for 30 minutes to allow intake of the indicator. The above-mentioned 384-well plate was transferred to FLIPR (Molecular Devices) and added with 12.5 μl/well of a compound dissolved in a 0.1% BSA-containing assay buffer to measure 3-minute change in the fluorescence intensity.

(Method for Calculating $EC_{50}$)

The difference between maximum and minimum fluorescence intensities before and after compound addition (RFU (Max-Min)) was determined by FLIPR automatic calculation. An activity rate was calculated where RFU (Max-Min) upon addition of a compound at a maximum concentration was defined 100% and RFU (Max-Min) upon addition of DMSO as a substitute for the compound at the same concentration was defined 0%. The rate was subjected to curve fitting using spreadsheet software XLfit to determine $EC_{50}$ value, i.e., a compound concentration upon 50% activity rate. The results are shown in Tables 16 and 17. From these results, the compounds of the present invention appear to have good CaSR agonistic activity and are useful as CaSR agonistic agents.

TABLE 16

| Example Number | EC50(μM) |
|---|---|
| 4 | 0.040 |
| 6 | 0.003 |
| 12 | 1.1 |
| 14 | 0.003 |
| 15 | 0.180 |
| 16 | 0.880 |
| 17 | 0.250 |
| 32 | 1.2 |
| 34 | 0.390 |
| 41 | 0.039 |
| 42 | 13.0 |
| 43 | 7.0 |
| 47 | 0.004 |
| 58 | 3.1 |
| 60 | 3.4 |
| 62 | 2.3 |
| 67 | 0.003 |
| 76 | 1.8 |

TABLE 17

| Example Number | EC50(μM) |
|---|---|
| 77 | 0.018 |
| 79 | 0.313 |

TABLE 17-continued

| Example Number | EC50(μM) |
| --- | --- |
| 81 | 3.7 |
| 82 | 1.0 |
| 83 | 21.1 |
| 85 | 1.6 |
| 88 | 2.3 |
| 89 | 1.1 |
| 90 | 1.0 |
| 92 | 1.8 |
| 93 | 5.0 |
| 99 | 15.0 |
| 100 | 5.8 |
| 101 | 3.6 |
| 104 | 0.490 |

Test Example II

Effect of Decreasing iPTH in Rat by Single Dose of Intravenous Administration (Method) A single dose was given to male SD (IGS) rat under pentobarbital anesthesia from a tail vein to examine the transition of serum iPTH and serum Ca concentration. Blood was taken before the administration and 5, 15, 30 and 60 minutes after the administration.

Compound No. 1 (the compound described in Example 6) was dissolved in physiological saline. Meanwhile, cinacalcet as a control substance was dissolved in PEG400: Saline=1:1 solution.

Figure 2:
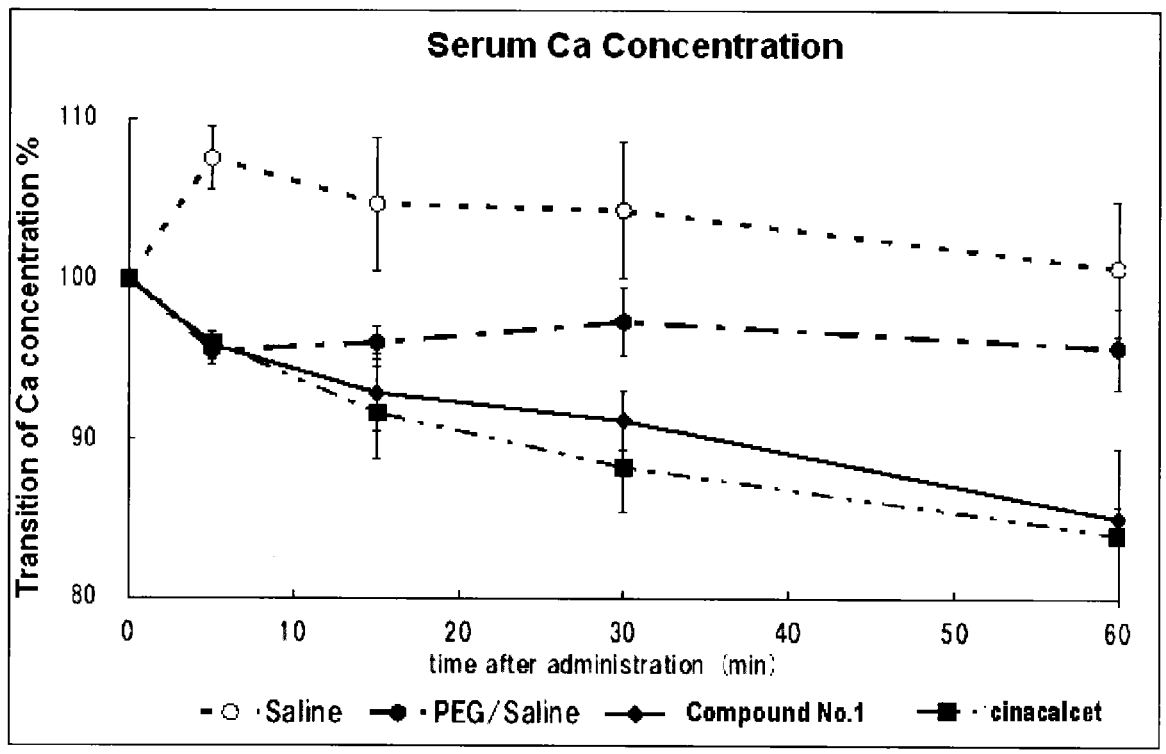
FIG. 2 A graph comparing the effects of Compound No. 1 and cinacalcet with respect to serum Ca concentration.

The results are shown in FIGS. 1 and 2. Compound No. 1 in Table 1 showed almost the same effect as cinacalcet at 0.1 mg/kg in decreasing serum iPTH and serum Ca. Accordingly, the compound of the present invention has an effect of decreasing iPTH, and thus suggested to be useful as a prophylactic or therapeutic agent for hyperparathyroidism.

Test Example III

Effect Against Non-Steroidal Anti-Inflammatory Drug (NSAID)-Induced Small Intestine Inflammation (Method) To a non-fasting rat, Compound No. 1 or 2 (the compound described in Example 14) (10 mg/kg) or Compound No. 3 (the compound described in Example 48) (3, 10 or 30 mg/kg) was orally administered. After 30 minutes, loxoprofen (60 mg/kg) was orally administered and the rat was left for 24 hours. Thirty minutes before the autopsy, 1 ml of 1% (w/w) Evansblue dye was intravenously administered to the rat. The small intestine (from duodenum to ileum) of the animal euthanized under deep ether anesthesia was isolated and immersed in 2% formalin for 10 minutes to fix the small intestine from the serosa side. The small intestine was dissected from the opposite side of the mesentery to measure the injury area ($mm^2$) thereof under a 10× dissecting microscope. T-test or Dunnett's test was employed as the statistical test where $p<0.05$ was considered to indicate significant difference.

Figure 3:
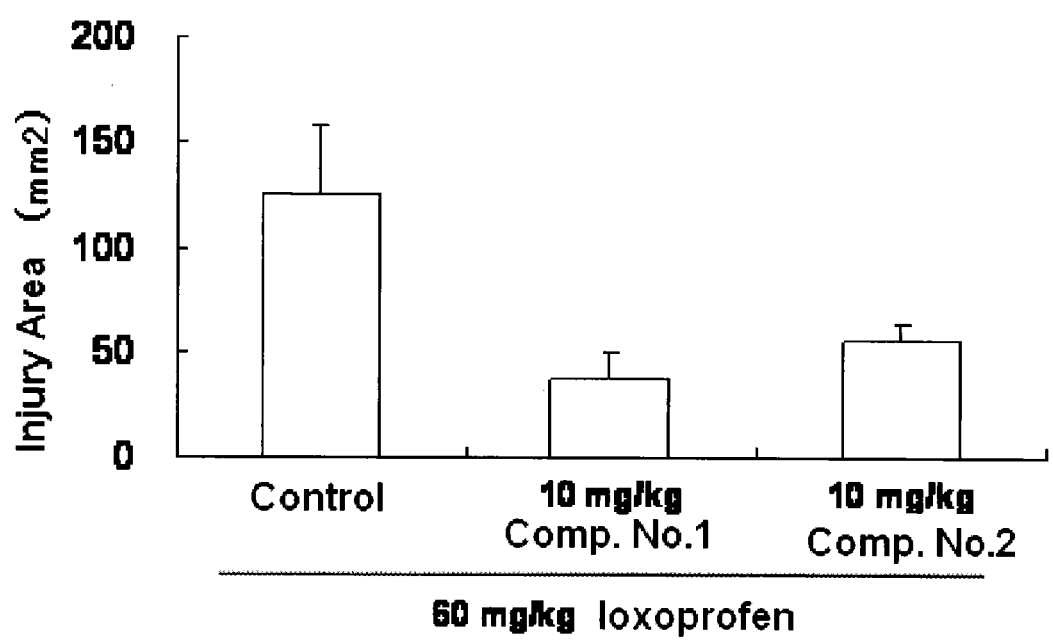
FIG. 3 A graph showing the effects of Compounds Nos. 1 and 2 on NSAID-induced small intestine inflammation. (*P<0.05)
Figure 4:
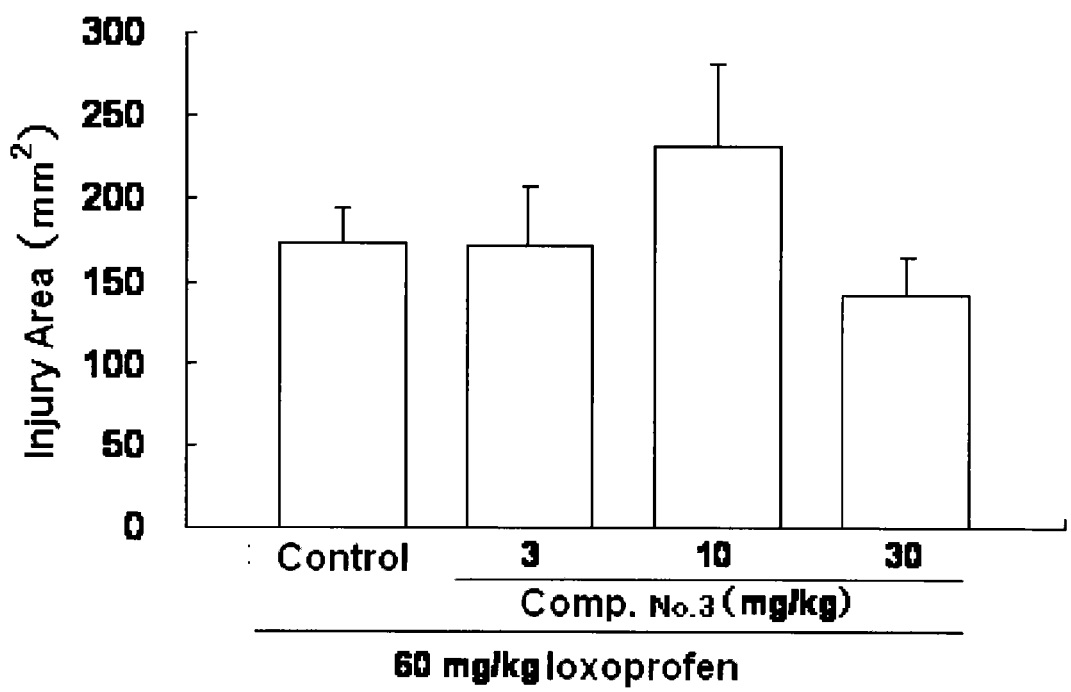
FIG. 4 A graph showing the effect of Compound No. 3 on NSAID-induced small intestine inflammation.
Figure 5:
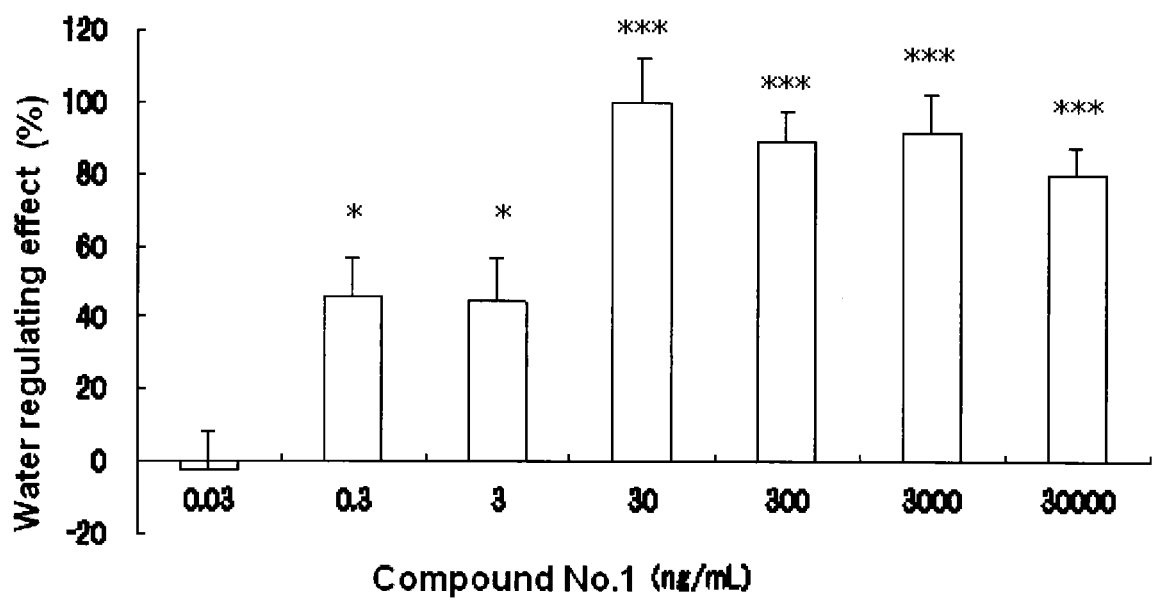
FIG. 5 A graph showing the effect of Compound No. 1 with respect to water absorption action using a colon loop technique.
Figure 6:
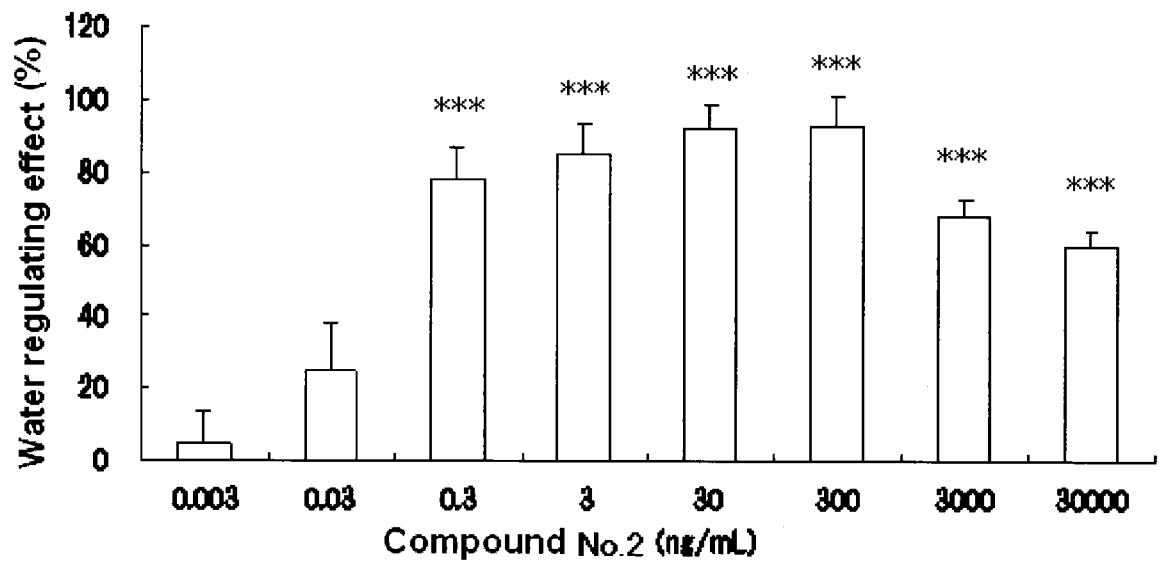
FIG. 6 A graph showing the effect of Compound No. 2 with respect to water absorption action using a colon loop technique.
Figure 7:
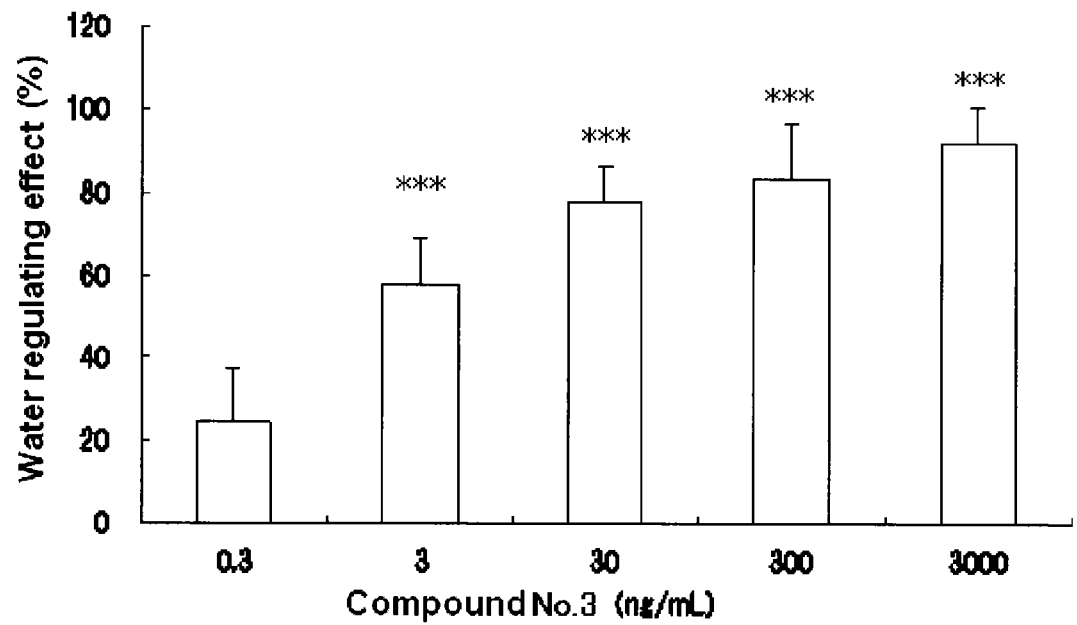
FIG. 7 A graph showing the effect of Compound No. 3 with respect to water absorption action using a colon loop technique.
Figure 8:
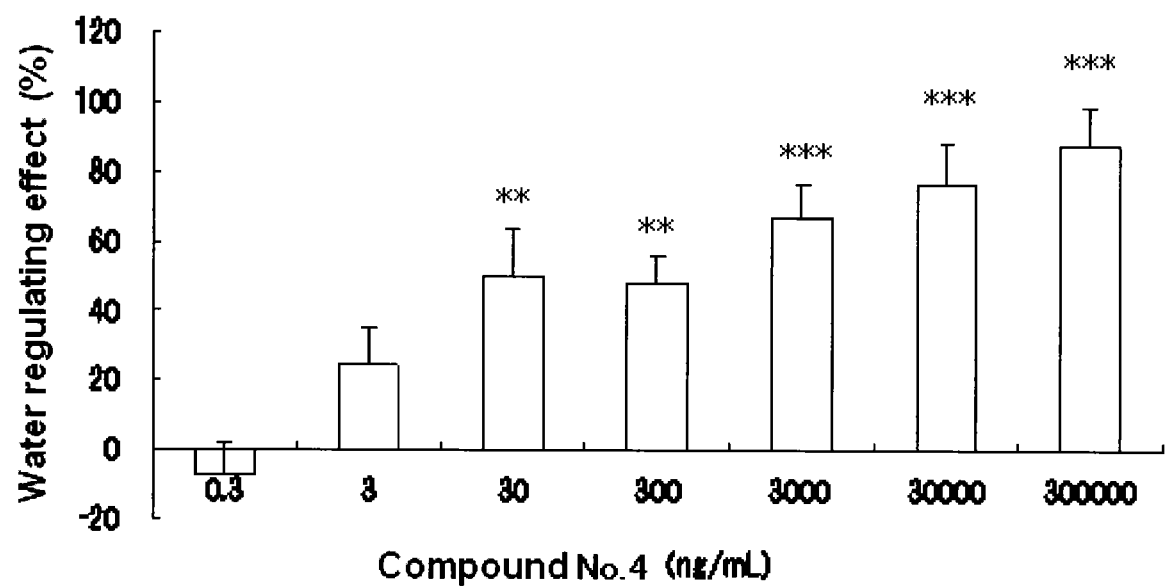
FIG. 8 A graph showing the effect of Compound No. 4 with respect to water absorption action using a colon loop technique.

The results are shown in FIGS. 3 and 4. Compound No. 1 significantly improved the injury area. In addition, Compounds Nos. 2 and 3 showed a tendency to improve the injury area. Therefore, compounds of the present invention were shown to be useful as a prophylactic or therapeutic agent for peptic ulcer.

Test Example IV

Effect of CaSR Agonist Against Water Absorption Action Using Rat Colon Loop Technique (Method) Appendix and large intestine were isolated from a male SD (IGS) rat under pentobarbital anesthesia, which were ligated 5 cm below the appendix to prepare a large intestine loop. Immediately after loop preparation, PGE2 (4 μg/ml/kg, SIGMA) was intraperitoneally administered. Thirty minutes later, 2 ml of Tyrode's solution (NaCl 136.9 mM, KCl 2.7 mM, $CaCl_2.2H_2O$ 1.8 mM, $MgCl_2.6H_2O$ 1.04 mM, $NaH_2PO_4.2H_2O$ 0.04 mM, $NaH_2PO_4.2H_2O$ 0.04 mM, Glucose 5.55 mM, $NaHCO_3$ 11.9 mM) was injected into the prepared loop. An hour later, weight of the loop, weight of the loop after removing the fluid therefrom and the loop area were measured to calculate the weight of liquid remaining in the loop per unit area.

The above-described Compounds Nos. 1-3 and Compound No. 4 (the compound described in Example 47) were used as the test compounds while the agents were dissolved in Tyrode's solution.

Remaining liquid measure per unit area ($g/cm^2$)= (weight of loop−weight of loop after removing fluid therefrom)/loop area.

Water absorption was assessed by calculating water regulating effect (%) according to the following formula.

Water regulating effect (%)=100−(remaining liquid measure per unit area obtained with agent−average remaining liquid measure per base unit area)/ (remaining liquid measure per unit area obtained with vehicle−average remaining liquid measure per base unit area)×100.

The results are shown in FIGS. 5-8. Compounds Nos. 1, 2, 3 and 4 promoted water absorption in a dose-depending manner. Accordingly, the compound of the present invention were shown to be useful as a prophylactic or therapeutic agent for diarrhea.

INDUSTRIAL APPLICABILITY

A compound of the present invention or a salt thereof, and a pharmaceutical agent thereof show a superior CaSR agonistic effect, and useful as a prophylactic or therapeutic agent for a disease that is ameliorated through CaSR activation, in particular, hyperparathyroidism, diarrhea, peptic ulcer or the like. In addition, a compound of the present invention or a salt thereof can also be used as seasonings that imparts kokumi.

This application is a continuation of International Patent Application No. PCT/JP2011/055033, filed on Mar. 4, 2011, and claims priority to Japanese Patent Application No. 2010-048310, filed on Mar. 4, 2010, both of which are incorporated herein by reference in their entireties.

The invention claimed is:
1. A compound of Formula (I) or a salt thereof:

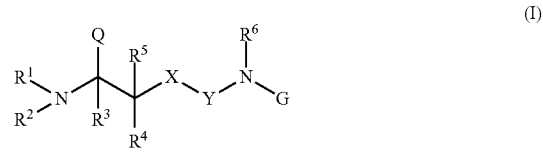

wherein $R^1$ and $R^2$, each independently, represent a hydrogen atom, or unsubstituted $C_{1-6}$ alkyl;

$R^3$ represents a hydrogen atom;

$R^4$ and $R^5$, each independently, represent a hydrogen atom, substituted or unsubstituted $C_{1-6}$ alkyl;

X represents $CH_2$, an oxygen atom, NH, or a sulfur atom;

Y represents C=O, SO, $SO_2$, or C=S;

$R^6$ represents a hydrogen atom;

G represents $R^7$-substituted phenyl or $R^7$-substituted pyridyl, where the $R^7$-substituted phenyl or the $R^7$-substituted pyridyl may further be substituted with one or two $R^8$;

$R^7$ represents sulfo or carboxyl;

$R^8$ represents substituted or unsubstituted $C_{1-6}$ alkyl, halogeno, hydroxy, substituted or unsubstituted $C_{1-6}$ alkoxy, sulfo, or $C_{1-3}$ alkylcarbonylamino, where they may be different when more than one $R^8$ exist;

Q represents a hydrogen atom, substituted or unsubstituted $C_{1-6}$ alkyl, carboxyl, $CONR^eR^f$, $CONHNHR^g$, $COR^h$, phenyl, or substituted or unsubstituted oxadiazolyl;

$R^e$ and $R^f$, each independently, represent a hydrogen atom, substituted or unsubstituted $C_{1-6}$ alkyl, substituted or unsubstituted $C_{1-6}$ alkylsulfonyl, phenylsulfonyl, substituted or unsubstituted $C_{3-8}$ cycloalkyl, or hydroxy, or alternatively, $R^e$ and $R^f$ may integrally form morpholino;

$R^g$ represents substituted or unsubstituted $C_{1-6}$ alkylcarbonyl; and $R^h$ represents substituted or unsubstituted $C_{1-6}$ alkoxy, provided that when X is methylene or an oxygen atom, Y is C=O, all of $R^1$-$R^5$ are hydrogen atoms, and G is $R^7$-substituted phenyl optionally substituted with one or two $R^8$, then, Q is a group other than carboxyl or $COR^h$.

2. The compound according to claim 1, or a salt thereof, wherein $R^8$ represents substituted or unsubstituted $C_{1-6}$ alkyl, halogeno, hydroxy, substituted or unsubstituted $C_{1-6}$ alkoxy, nitro, or sulfo, Q represents a hydrogen atom, substituted or unsubstituted $C_{1-6}$ alkyl (wherein the substituent on said substituted $C_{1-6}$ alkyl is selected from the group consisting of phenyl, carbamoyl, and cyano), carboxyl, $CONR^eR^f$, $CONHNHR^g$, $COR^h$, phenyl, or substituted or unsubstituted oxadiazolyl (wherein the substituent on said substituted oxadiazolyl is selected from the group consisting of $C_{1-6}$ alkyl, $C_{1-6}$ alkyl substituted with phenyl, phenyl substituted with halogen, phenyl substituted with $C_{1-6}$ alkyl, and thiazolyl);

$R^e$ and $R^f$, each independently, represent a hydrogen atom, substituted or unsubstituted $C_{1-6}$ alkyl (wherein the substituent on said substituted $C_{1-6}$ alkyl is selected from the group consisting of phenyl, phenyl substituted with $C_{1-6}$ alkyl, phenyl substituted with halogen, and imidazolyl), $C_{1-6}$ alkylsulfonyl, phenylsulfonyl, substituted or unsubstituted $C_{3-8}$ cycloalkyl, or hydroxy, or alternatively, $R^e$ and $R^f$ may integrally form morpholino;

$R^g$ represents substituted or unsubstituted $C_{1-6}$ alkylcarbonyl; and $R^h$ represents substituted or unsubstituted $C_{1-6}$ alkoxy, provided that when X is methylene or an oxygen atom, Y is C=O, all of $R^1$-$R^5$ are hydrogen atoms, and G is $R^7$-substituted phenyl optionally substituted with one or two $R^8$, then, Q is a group other than carboxyl or $COR^h$.

3. A pharmaceutical composition, comprising:

the compound or a pharmaceutically acceptable salt thereof according to claim 1 or 2 as an active ingredient; and a pharmaceutically acceptable excipient.

4. The compound according to claim 1, wherein G represents $R^7$-substituted phenyl or $R^7$-substituted pyridyl, where the $R^7$-substituted phenyl or the $R^7$-substituted pyridyl is not further substituted with one or two $R^8$.

5. The pharmaceutical composition according to claim 3, wherein G represents $R^7$-substituted phenyl or $R^7$-substituted pyridyl, where the $R^7$-substituted phenyl or the $R^7$-substituted pyridyl is not further substituted with one or two $R^8$.

6. The compound according to claim 1, wherein

X represents NH,

Y represents C=O or C=S,

G represents $R^7$-substituted phenyl, which may further be substituted with one or two $R^8$, $R^7$ represents sulfo or carboxyl, $R^8$ represents $C_{1-6}$ alkyl, halogen, hydroxy, $C_{1-3}$ alkylcarbonylamino or sulfo, where they may be different when more than one $R^8$ exist, and Q represents carboxyl, $CONR^eR^f$, $CONHNHR^g$ or $COR^h$.

7. The compound according to claim 1, wherein G is phenyl, X is NH, Y is CO, and Q is COOH.

8. The compound according to claim 2, wherein

X represents NH,

Y represents C=O or C=S,

G represents $R^7$-substituted phenyl, which may further be substituted with one or two $R^8$, $R^7$ represents sulfo or carboxyl, $R^8$ represents $C_{1-6}$ alkyl, halogeno, hydroxy, $C_{1-3}$ alkylcarbonylamino or sulfo, where they may be different when more than one $R^8$ exist, and Q represents carboxyl, $CONR^eR^f$, $CONHNHR^g$ or $COR^h$.

9. The compound according to claim 2, wherein G is phenyl, X is NH, Y is CO, and Q is COOH.

* * * * *

UNITED STATES PATENT AND TRADEMARK OFFICE
CERTIFICATE OF CORRECTION

PATENT NO. : 9,253,997 B2
APPLICATION NO. : 13/600977
DATED : February 9, 2016
INVENTOR(S) : Sugiki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
Sixth Day of June, 2017

Michelle K. Lee
*Director of the United States Patent and Trademark Office*

UNITED STATES PATENT AND TRADEMARK OFFICE
CERTIFICATE OF CORRECTION

PATENT NO. : 9,253,997 B2  
APPLICATION NO. : 13/600977  
DATED : February 9, 2016  
INVENTOR(S) : Masayuki Sugiki et al.

Page 1 of 1

It is certified that error appears in the above-identified patent and that said Letters Patent is hereby corrected as shown below:

In the Claims

In Column 97, Claim 1, Line 13-14, "alkoxy, sulfo," should read -- alkoxy, nitro, sulfo, --.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*